US008583609B2

(12) United States Patent
Sewall

(10) Patent No.: US 8,583,609 B2
(45) Date of Patent: Nov. 12, 2013

(54) METHOD AND SYSTEM FOR CREATING AN INDUSTRY-SPECIFIC COMPUTER DICTIONARY AND METADATA APPARATUS FOR COMPUTER MANAGEMENT APPLICATIONS USING A MULTI-LEVEL DATABASE OF TERMS AND DEFINITIONS

(76) Inventor: Barry Sewall, Excelsior, MN (US)

( * ) Notice: Subject to any disclaimer, the term of this patent is extended or adjusted under 35 U.S.C. 154(b) by 0 days.

(21) Appl. No.: 13/367,522

(22) Filed: Feb. 7, 2012

(65) Prior Publication Data

US 2012/0226719 A1    Sep. 6, 2012

Related U.S. Application Data

(60) Provisional application No. 61/440,467, filed on Feb. 8, 2011.

(51) Int. Cl.
*G06F 17/30* (2006.01)

(52) U.S. Cl.
USPC ........................................... 707/693; 707/802

(58) Field of Classification Search
USPC .................. 707/692–693, 696, 792, 802–803
See application file for complete search history.

(56) References Cited

U.S. PATENT DOCUMENTS 5,257,365 A * 10/1993 Powers et al. ..................... 1/1

* cited by examiner

*Primary Examiner* — Jacob F Bétit
*Assistant Examiner* — Amanda Willis
(74) *Attorney, Agent, or Firm* — Gerald E. Helget; Nelson R. Capes; Briggs and Morgan, P.A.

(57) ABSTRACT

A method and system for generating and storing definitions from a multi-level database of unique industry-specific terms, organizing the words, phrases and their exhaustive numerical definitions in a digital dictionary, and providing the architecture to create new files and label existing files with metadata from the dictionary so as to provide a common, secure platform to better manage elements in and related to the industry. An example of an industry in which the method and system may be used is the healthcare industry. The system addresses every facet of the industry including quality control, performance, reimbursement, licensing and credentials, managing organizations and patient's health records. The unique digital language, deep definitions and consistent terminology also form the basis for many novel product concepts designed to improve efficiency and quality. A practice management product for radiology is also described.

21 Claims, 85 Drawing Sheets

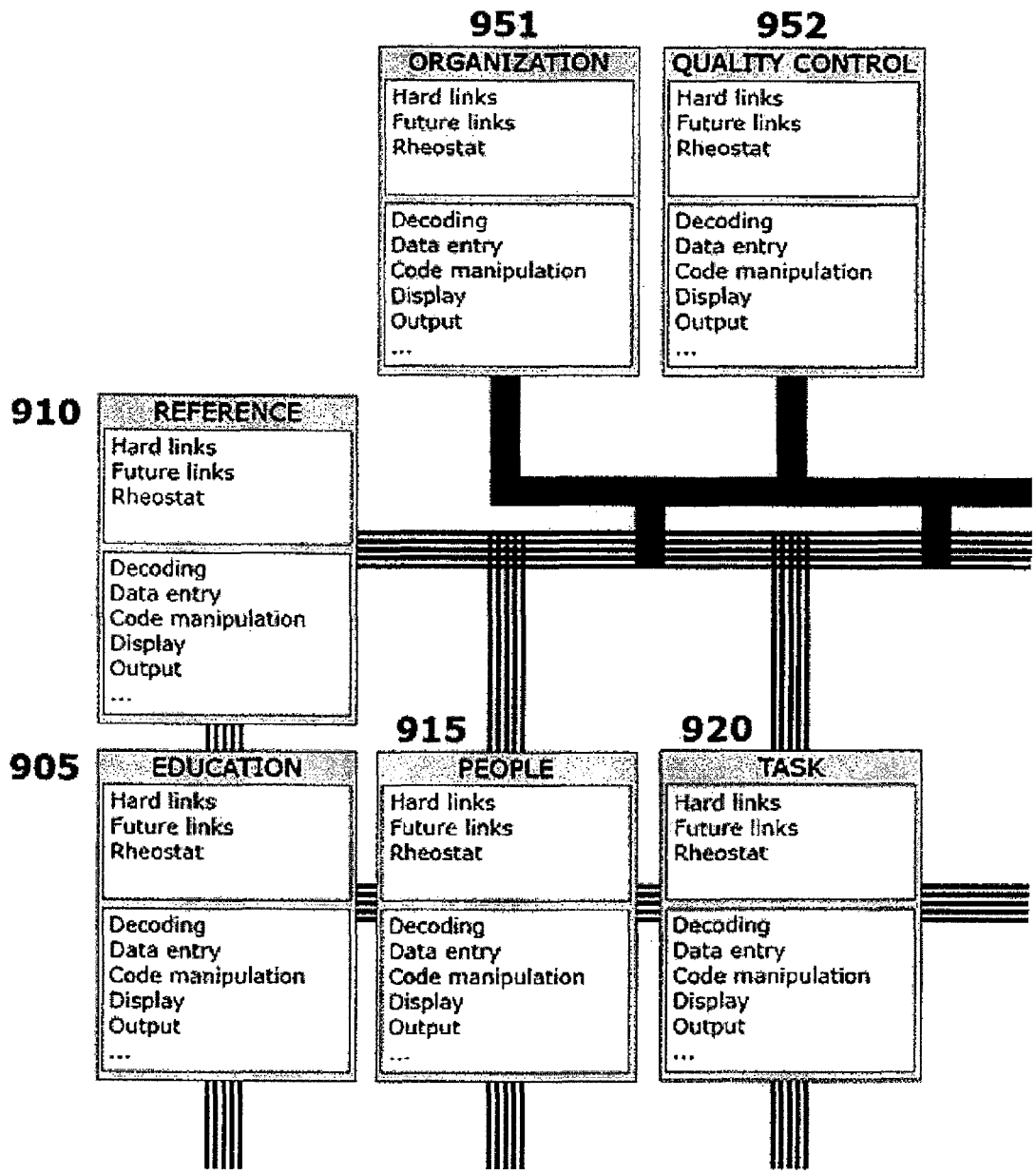
FIG. 4.1

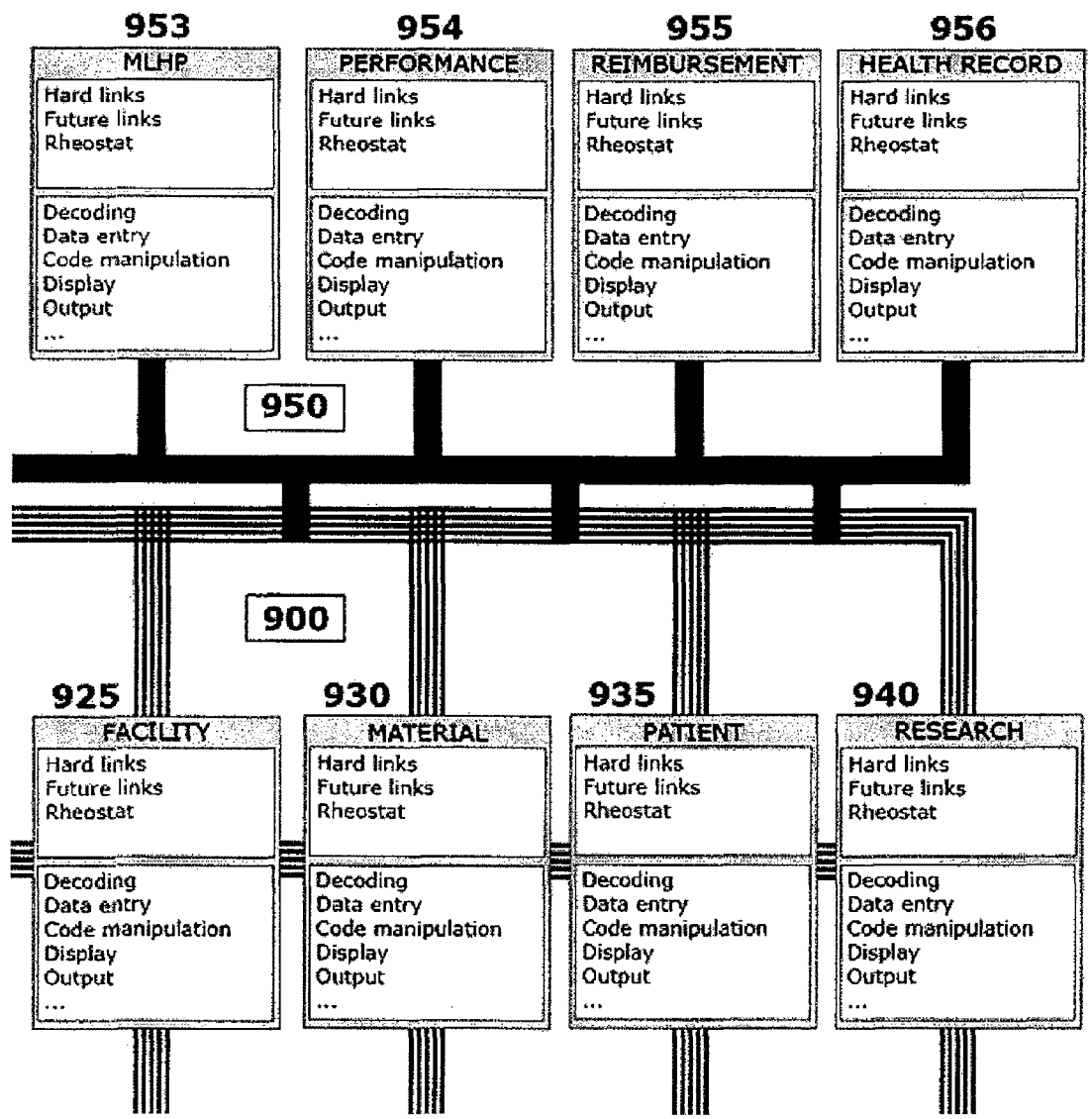
FIG. 4.2

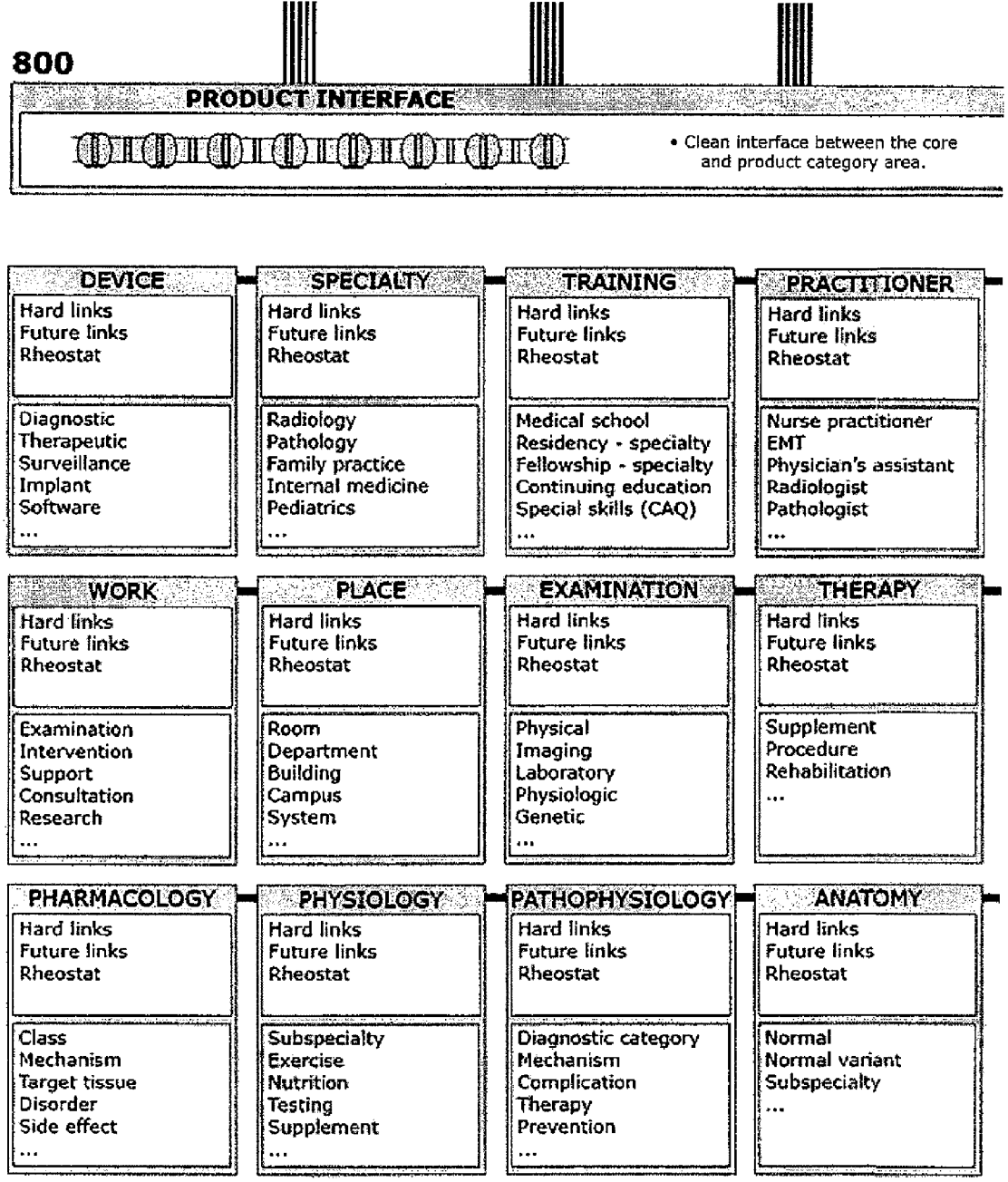
FIG. 4.3

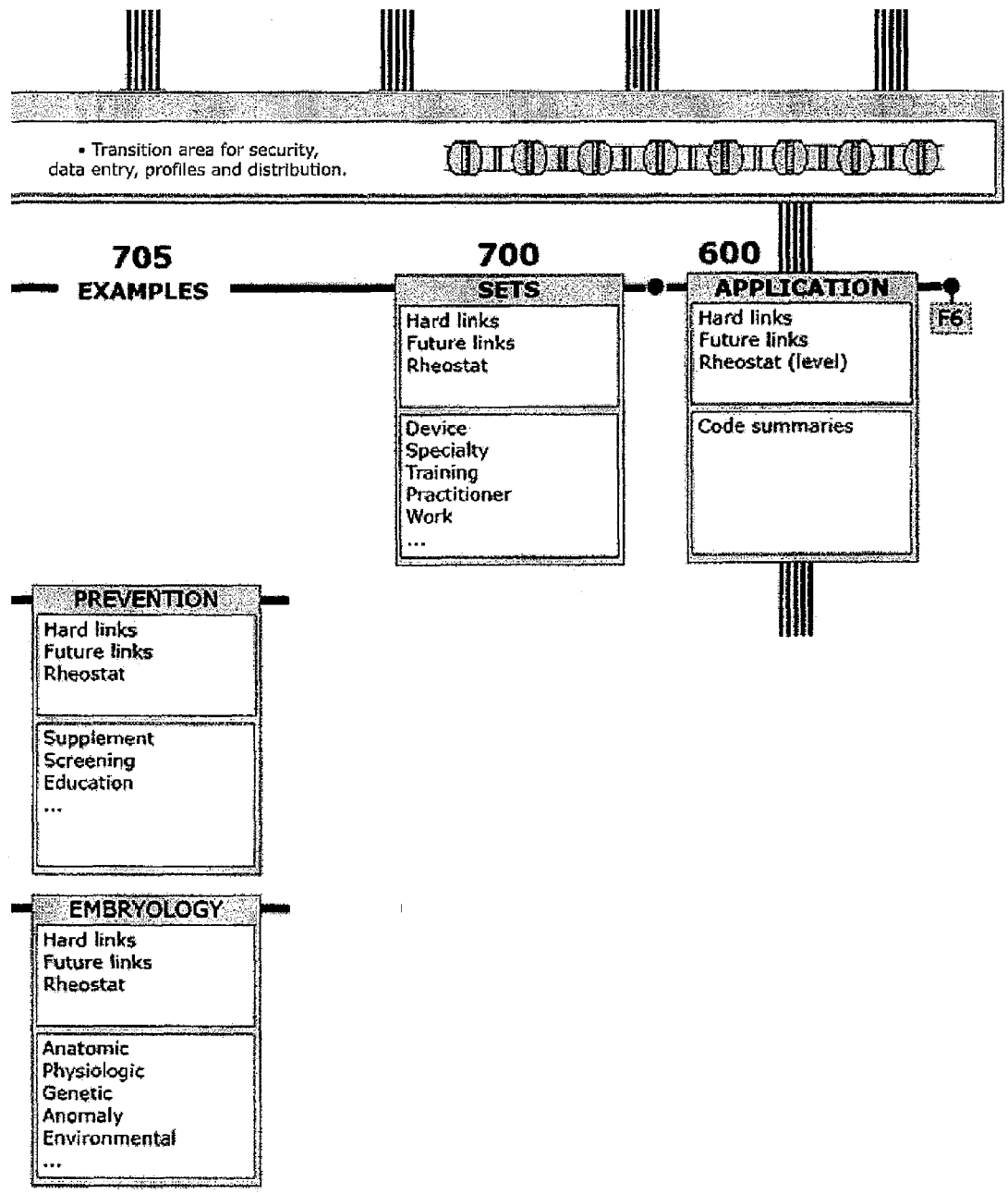
FIG. 4.4

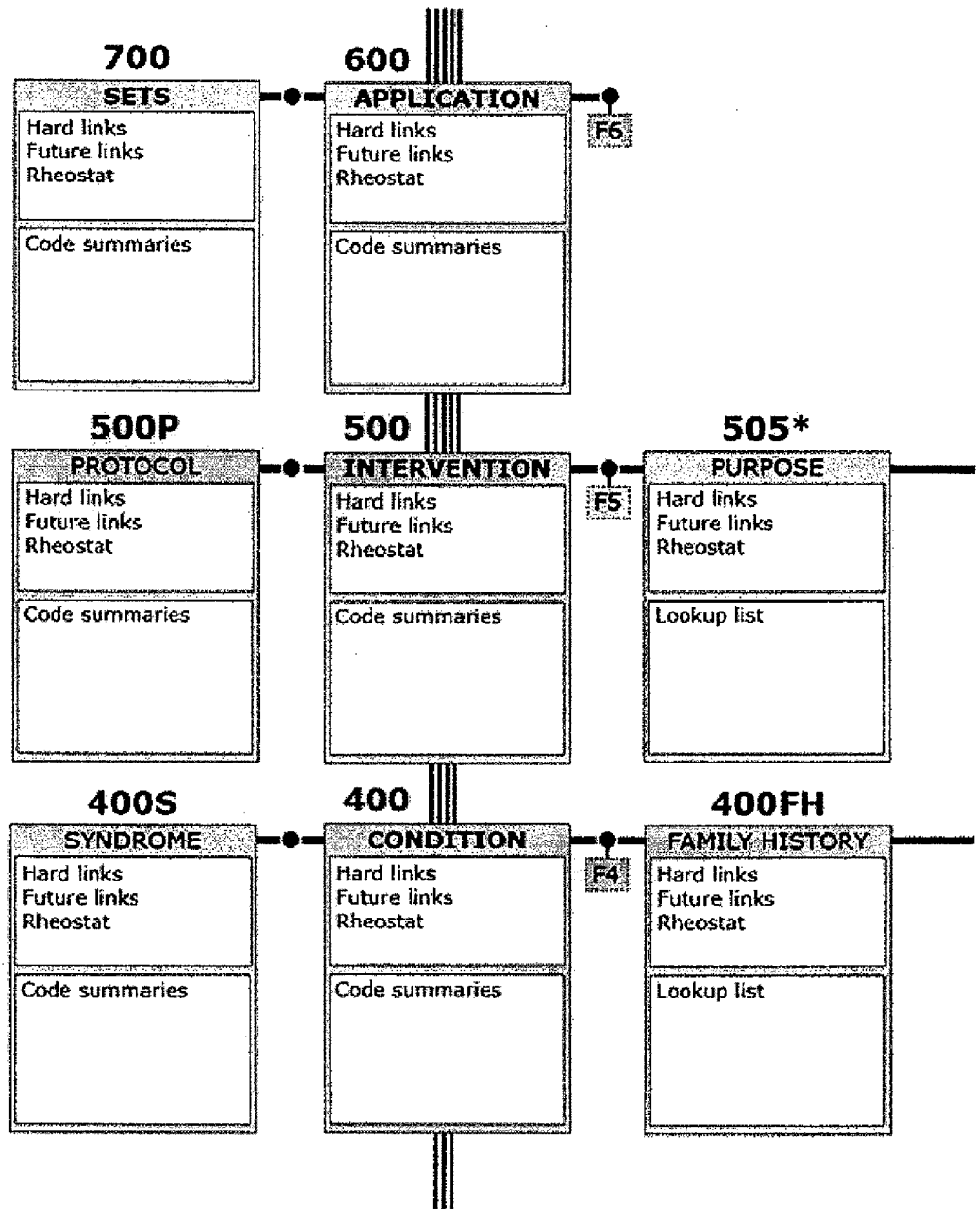
FIG. 5.1

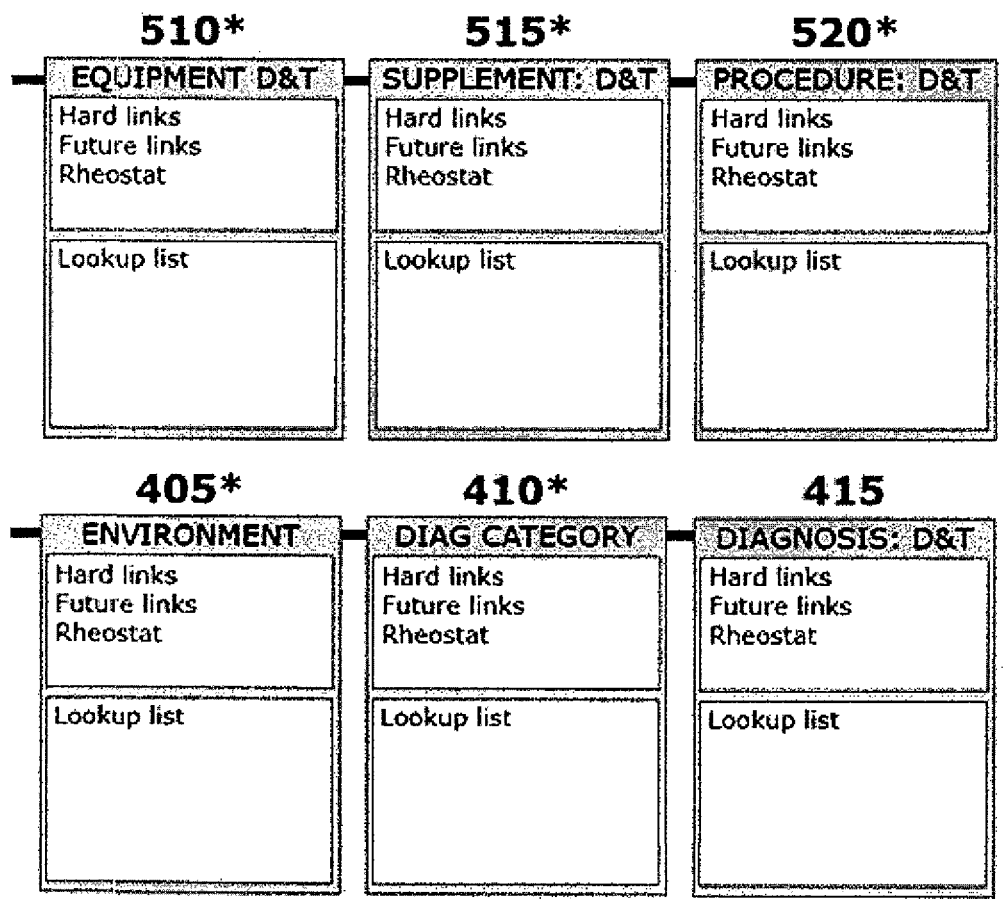
FIG. 5.2

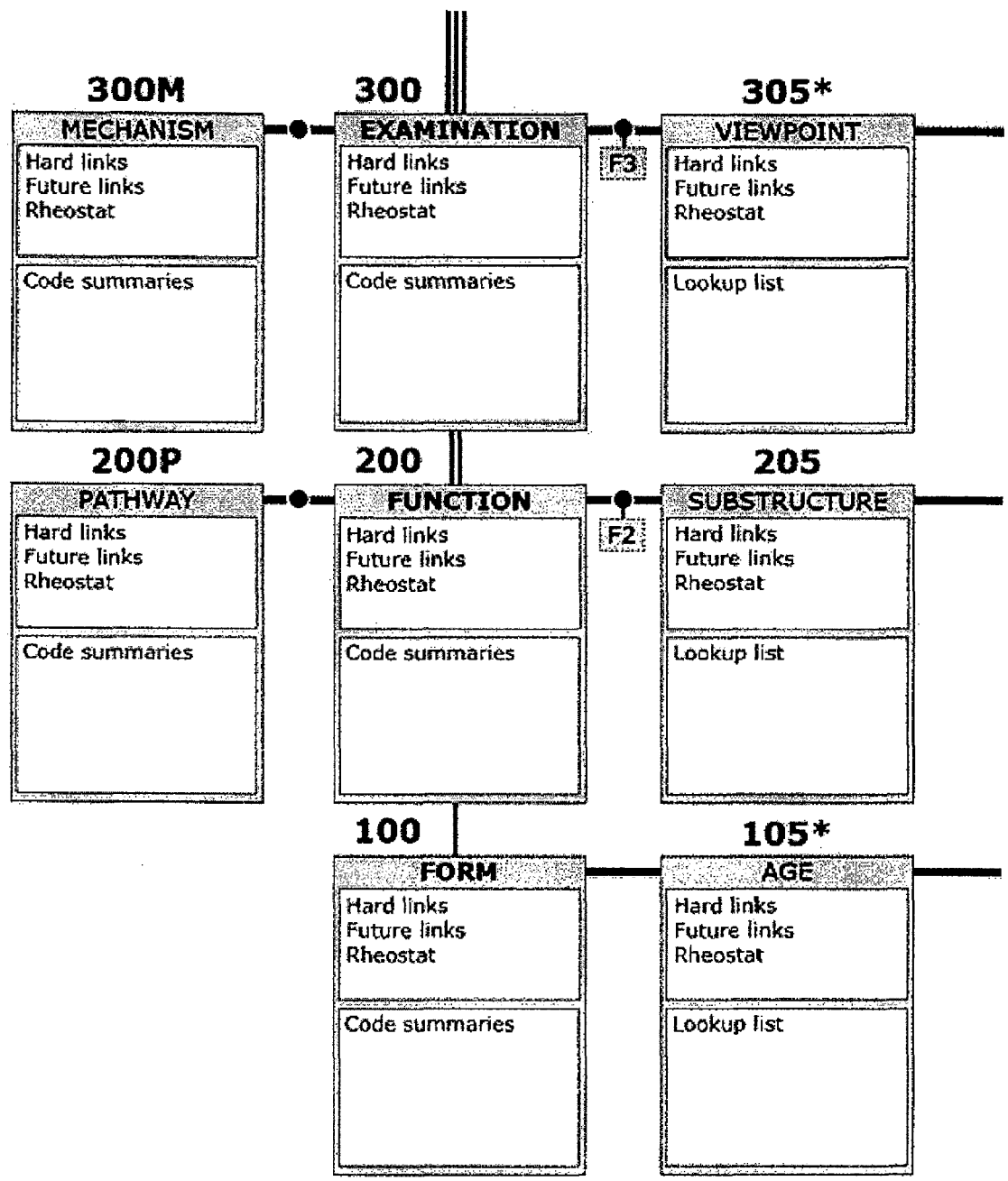
FIG. 5.3

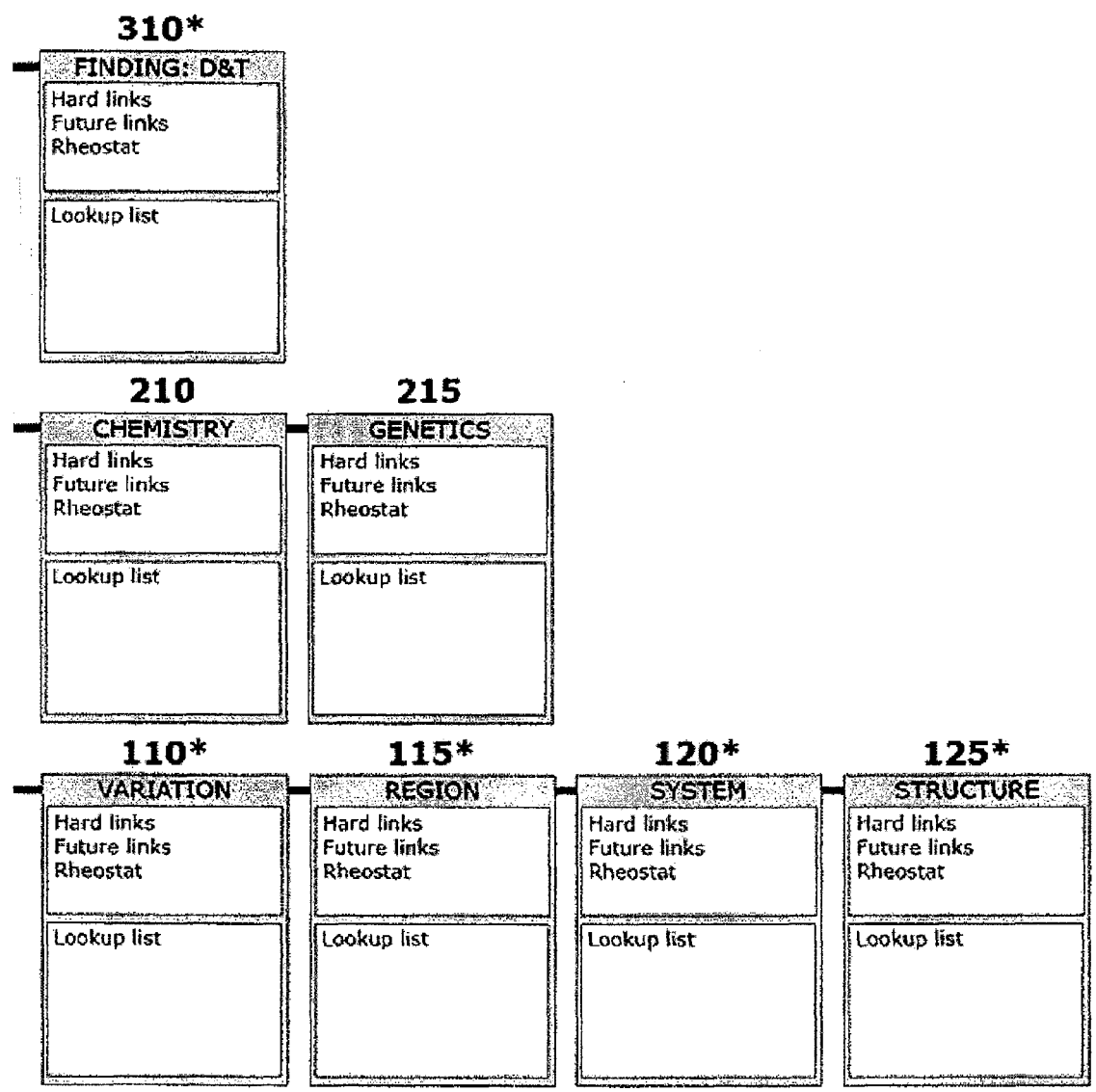
FIG. 5.4

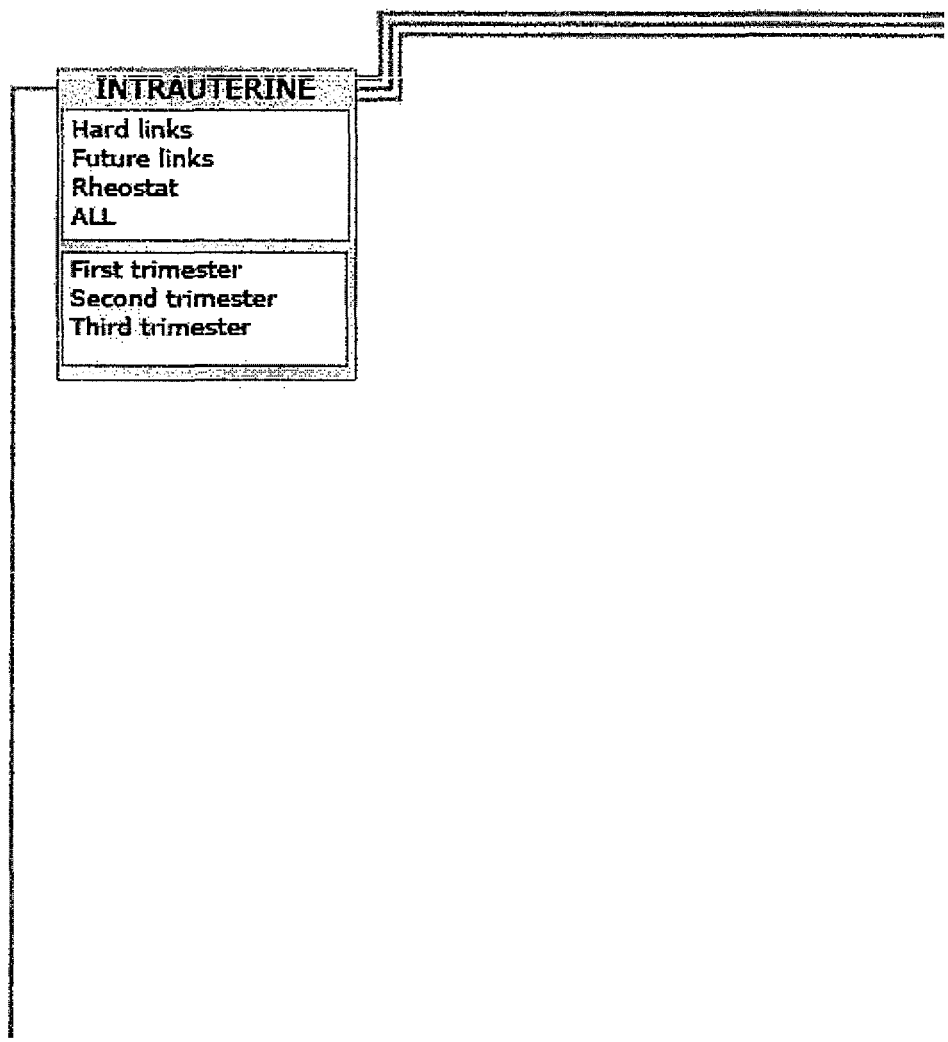
FIG. 6.1

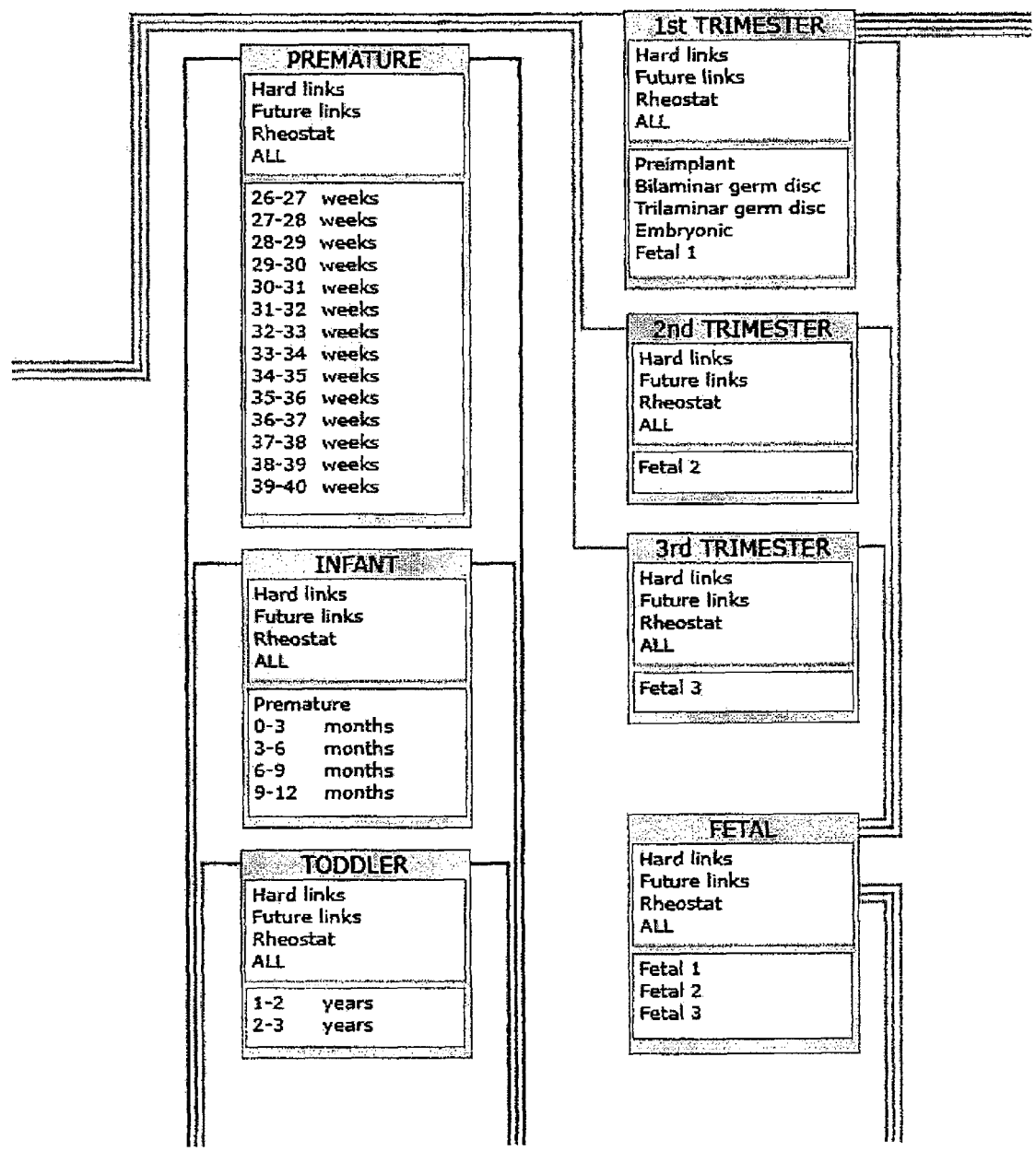
FIG. 6.2

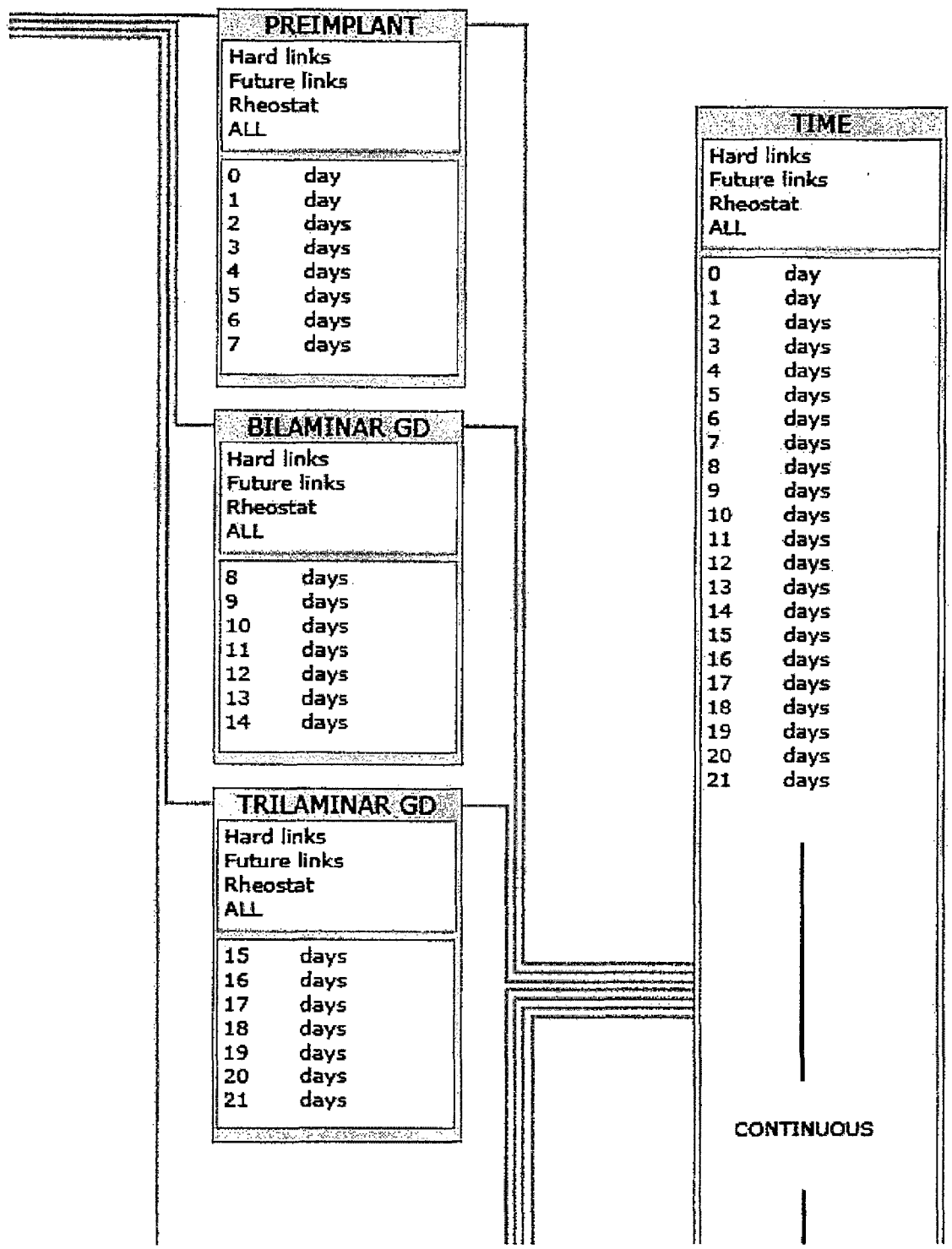
FIG. 6.3

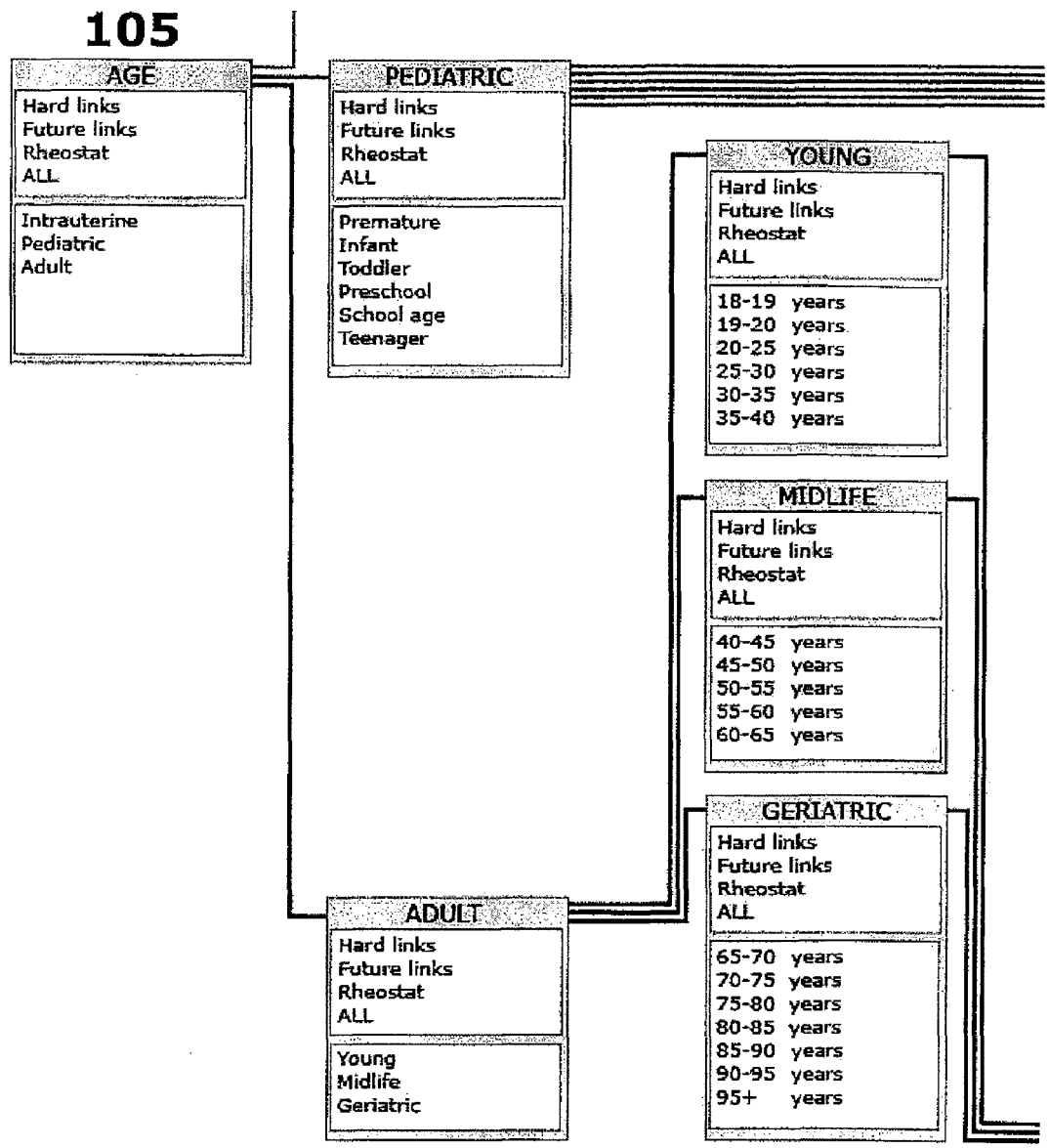
FIG. 6.4

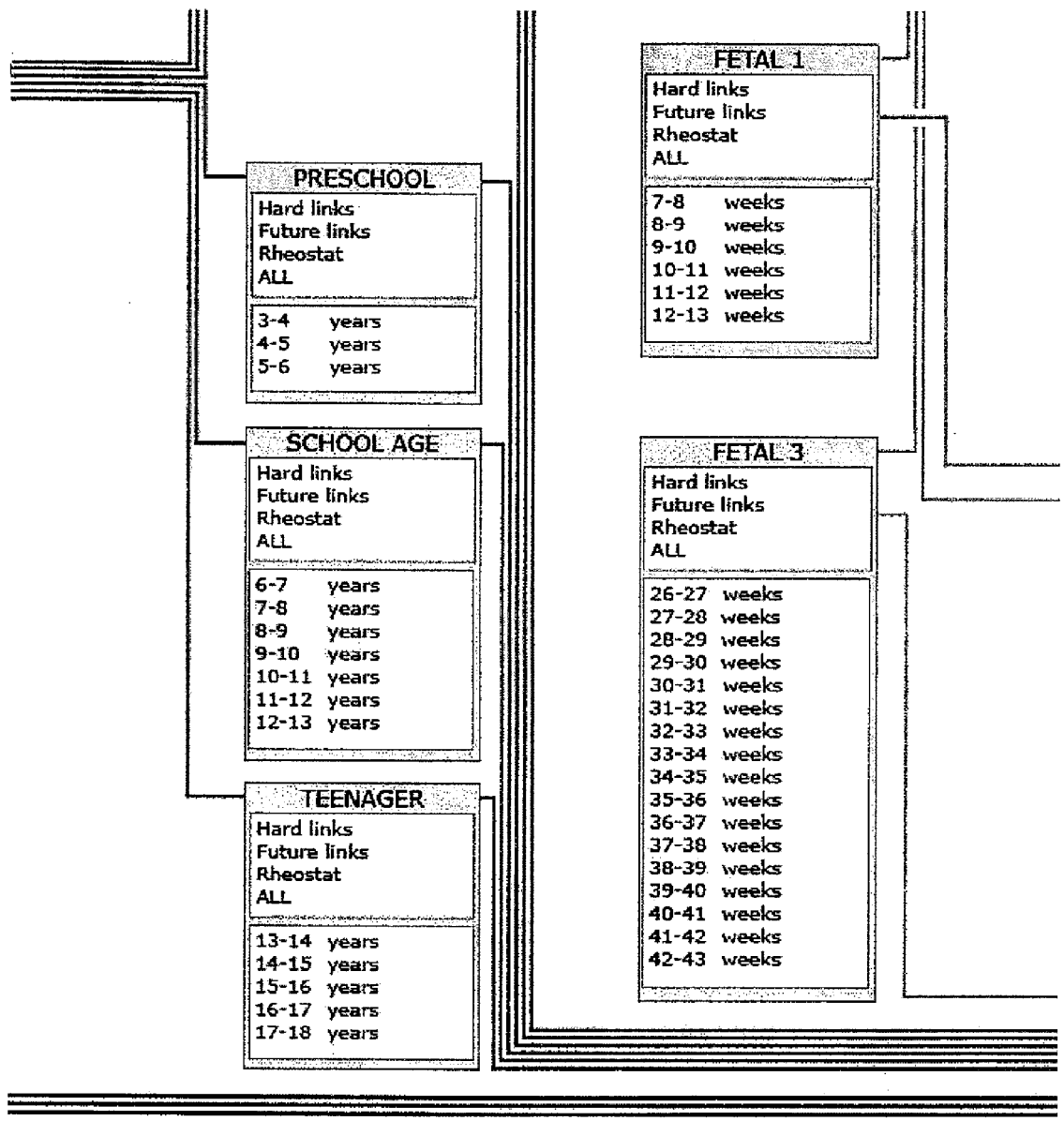
FIG. 6.5

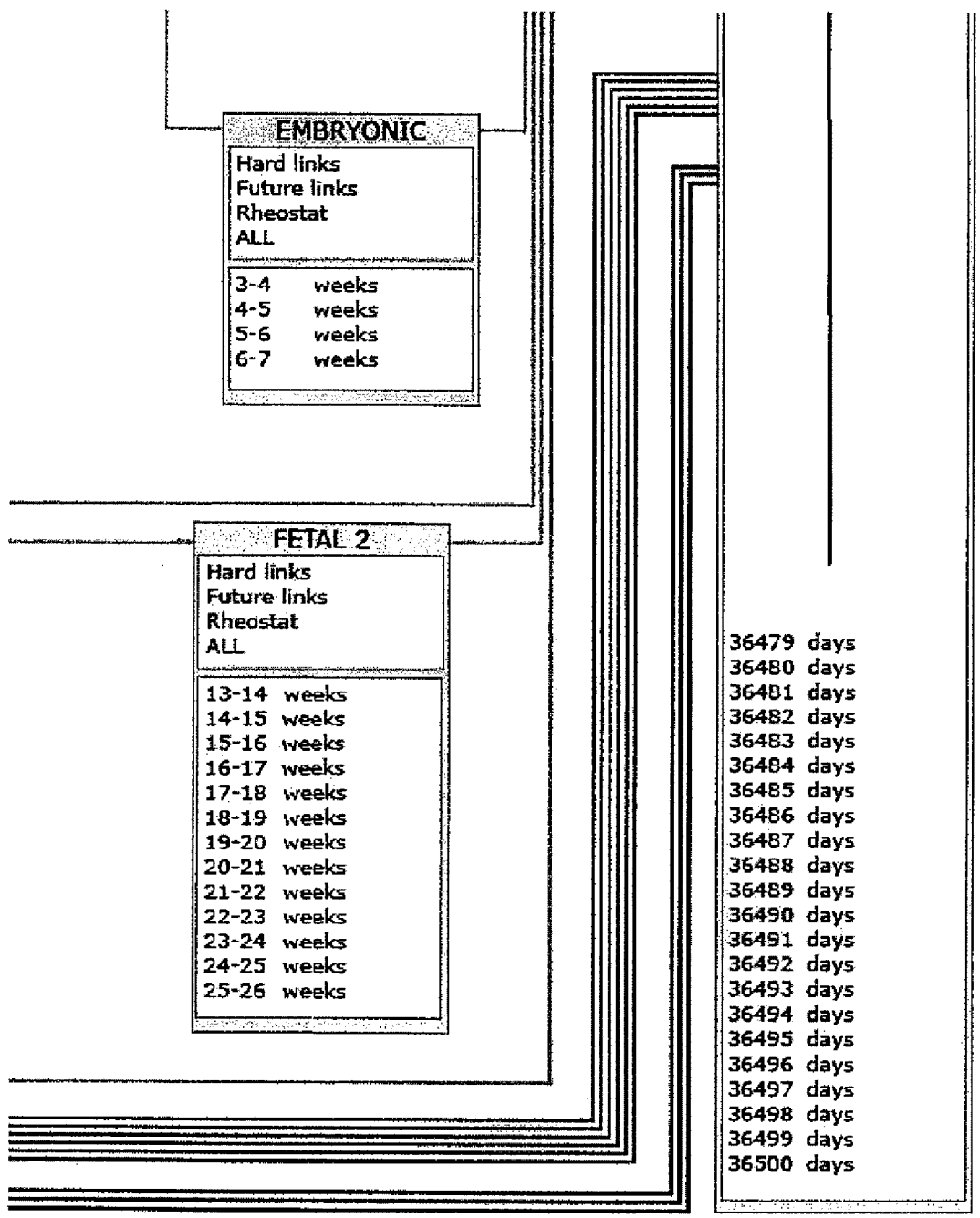
FIG. 6.6

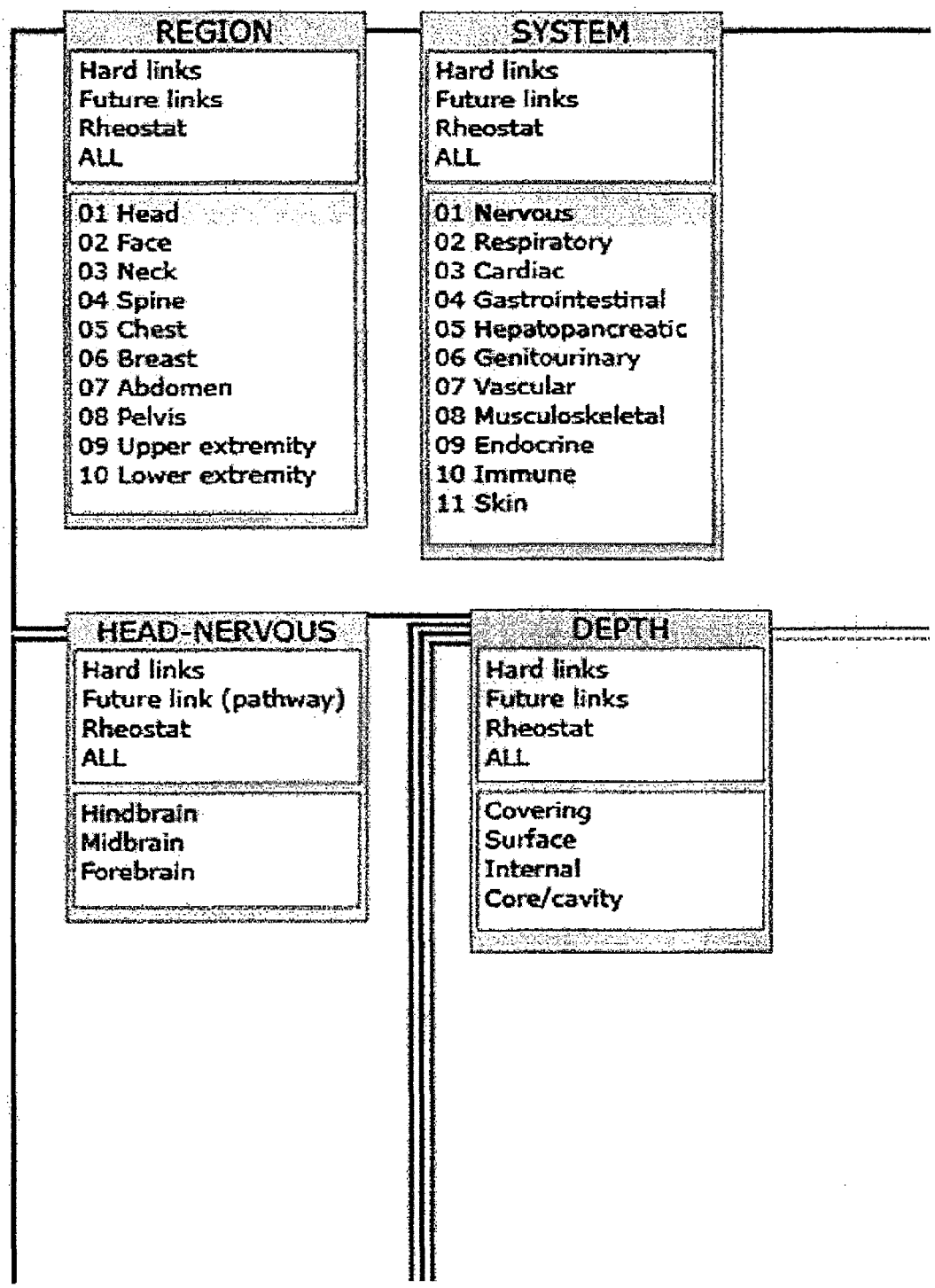
FIG. 7.1

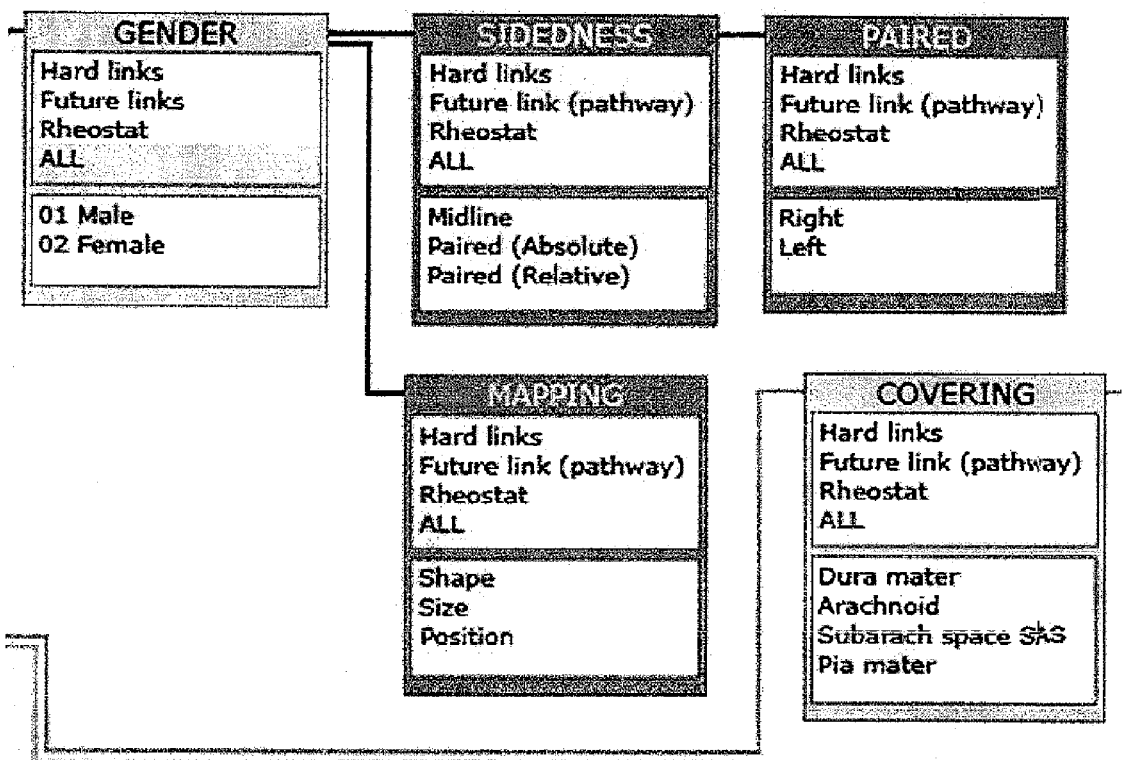
FIG. 7.2

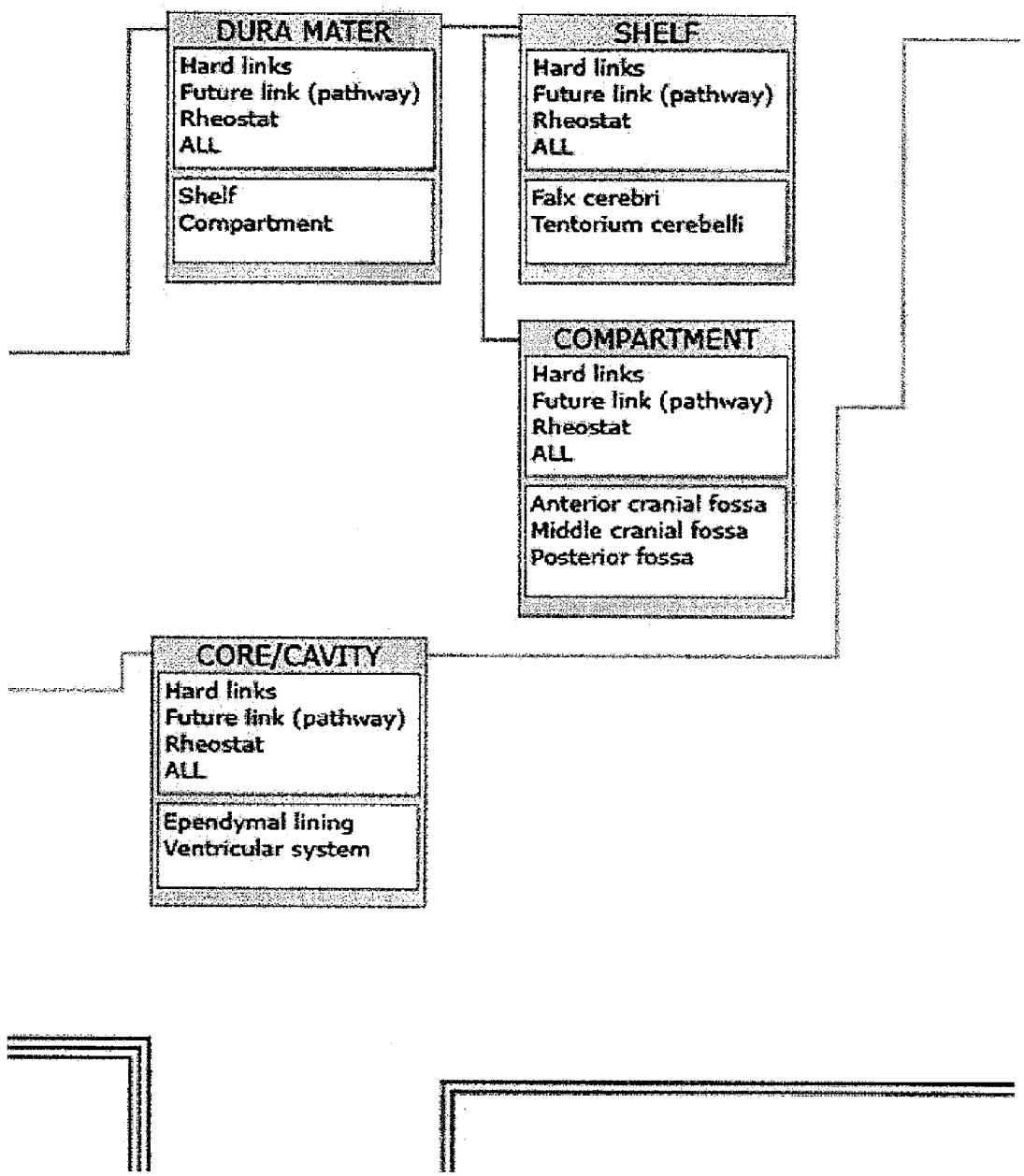
FIG. 7.3

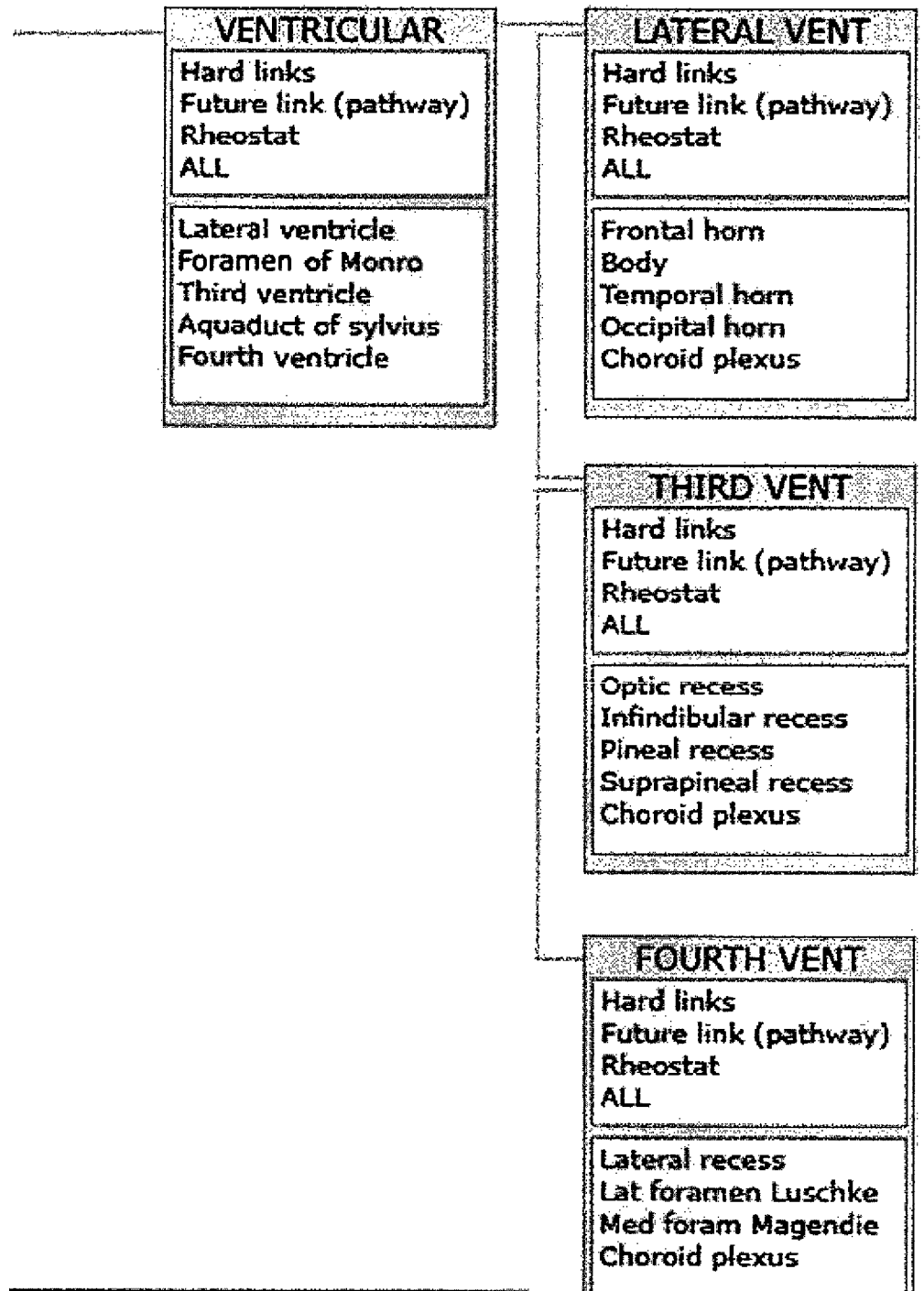
FIG. 7.4

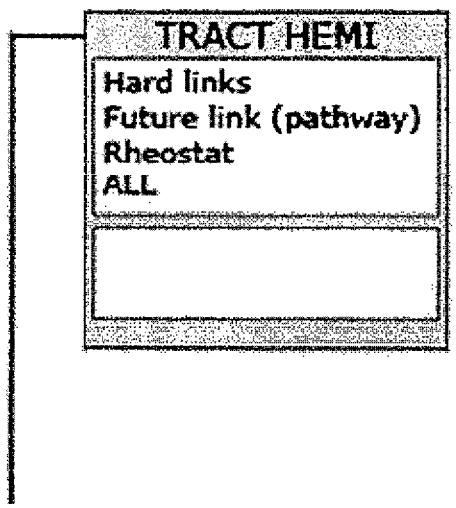
FIG. 7.5

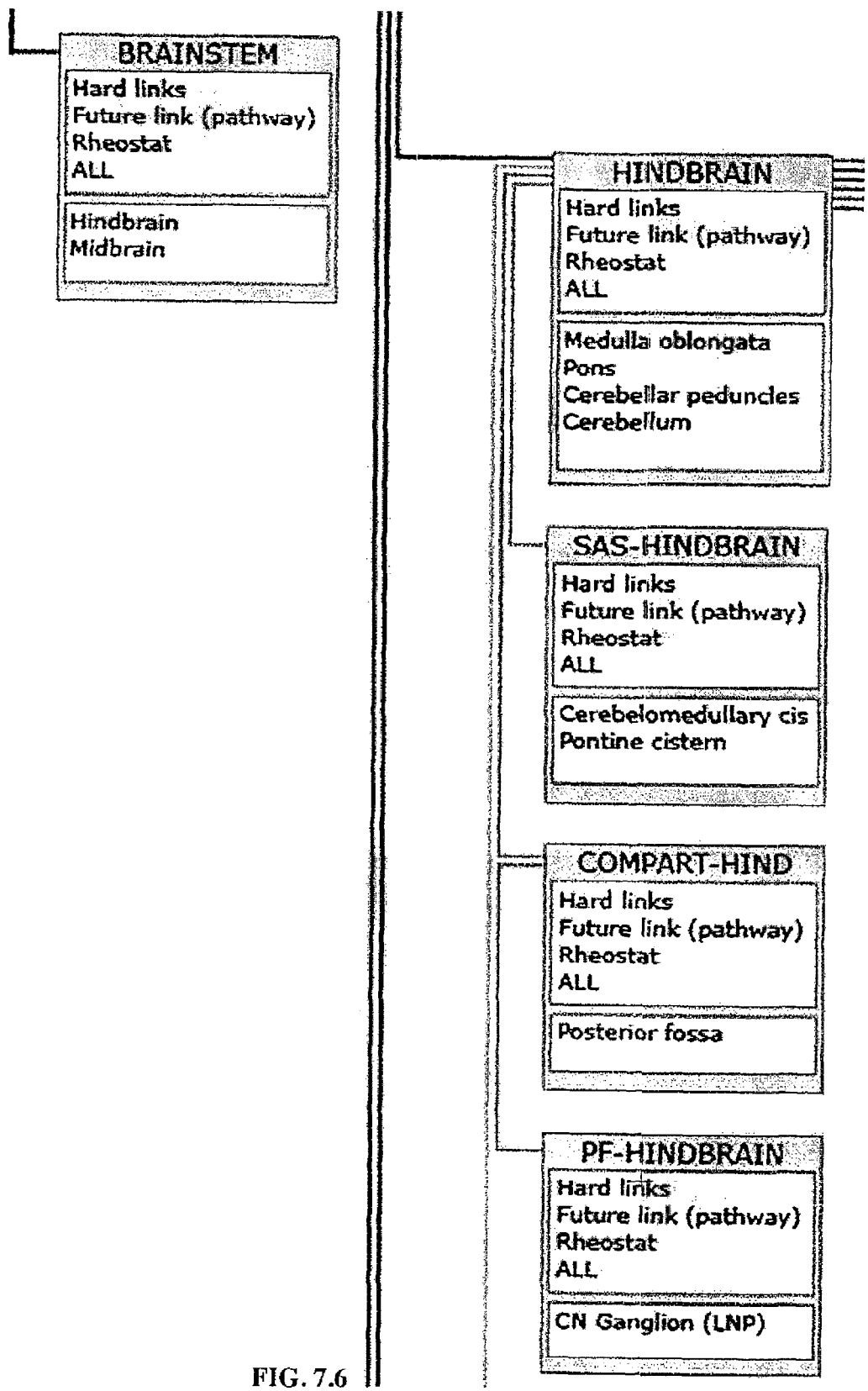
FIG. 7.6

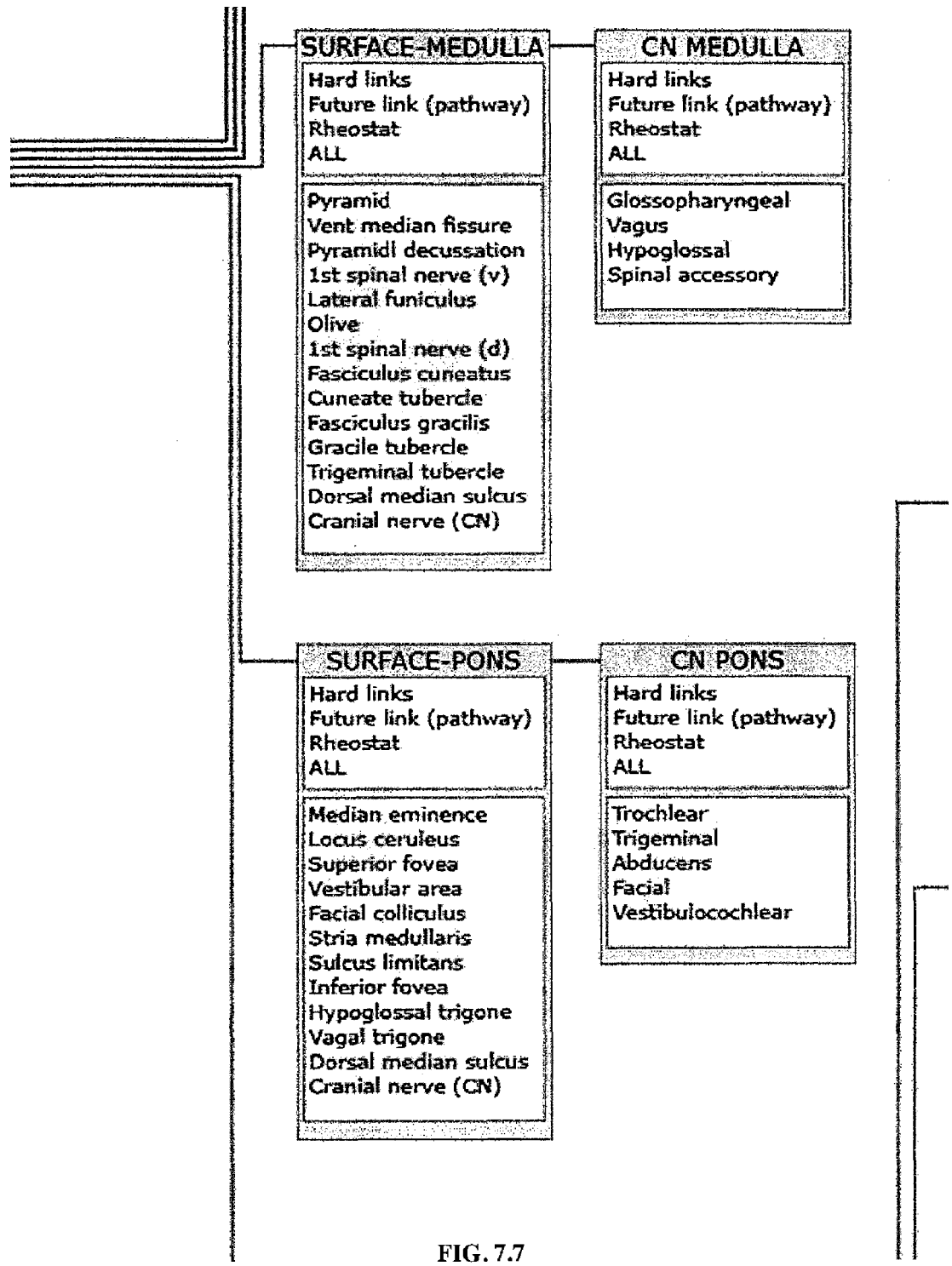
FIG. 7.7

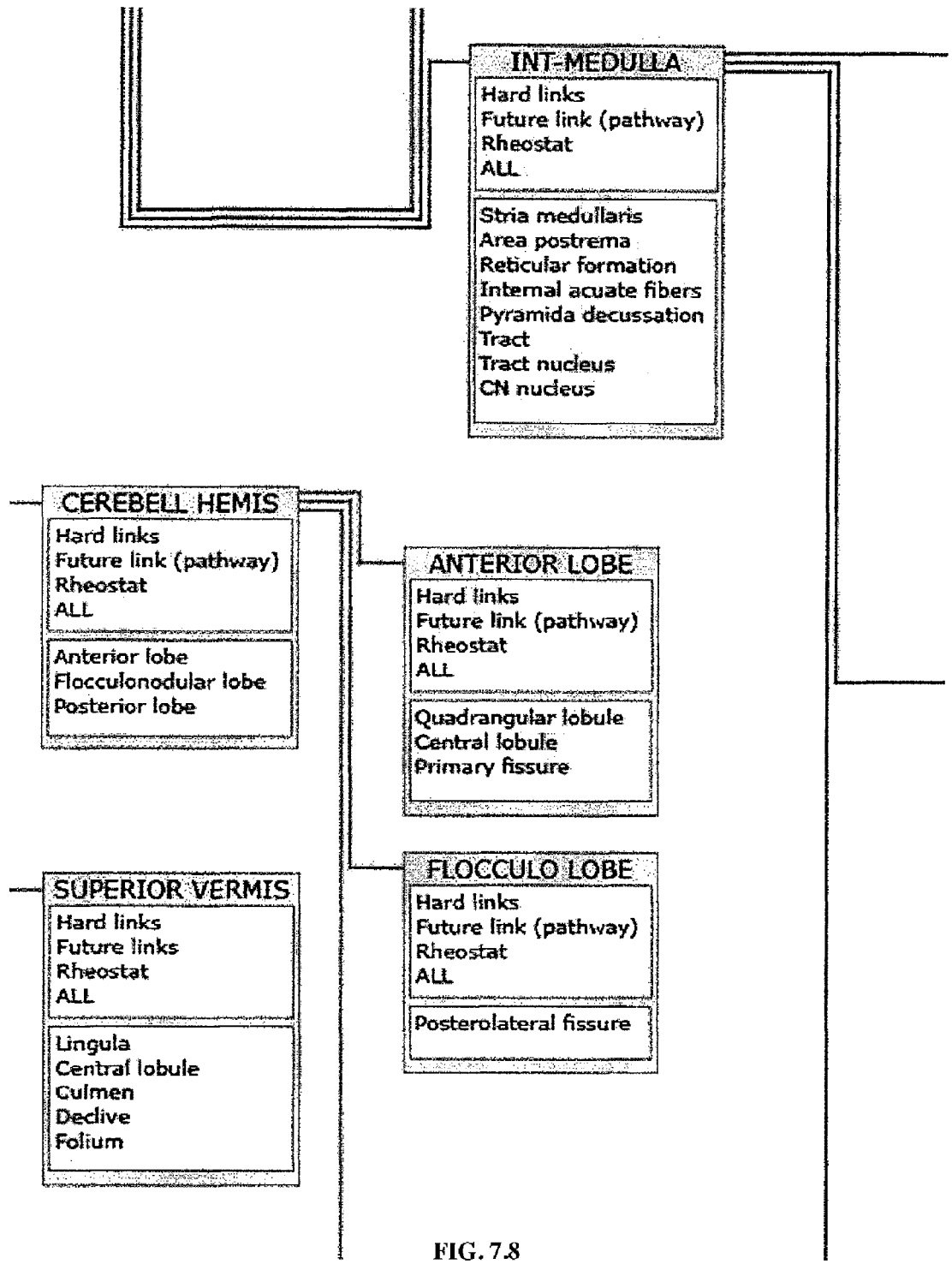
FIG. 7.8

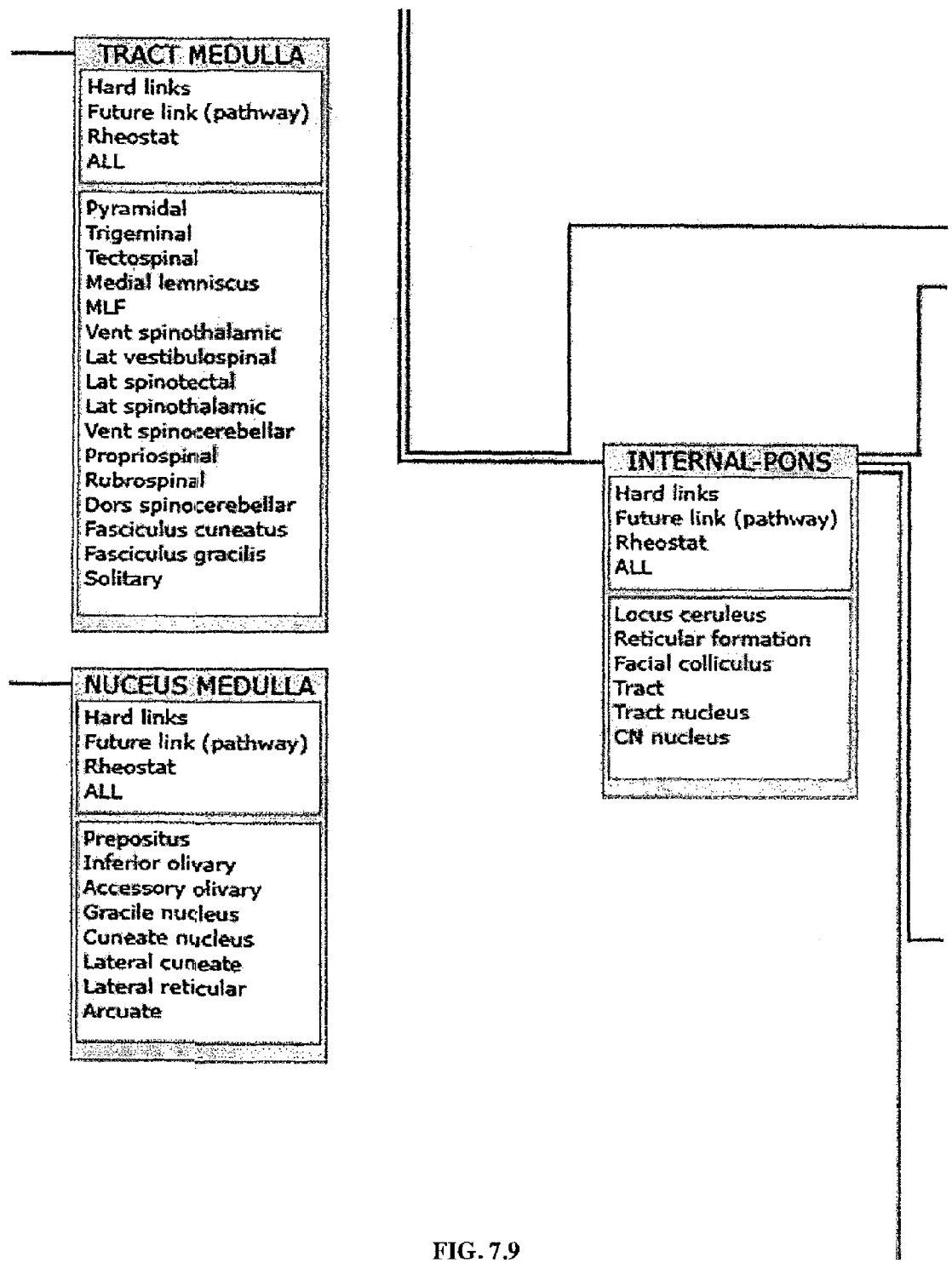
FIG. 7.9

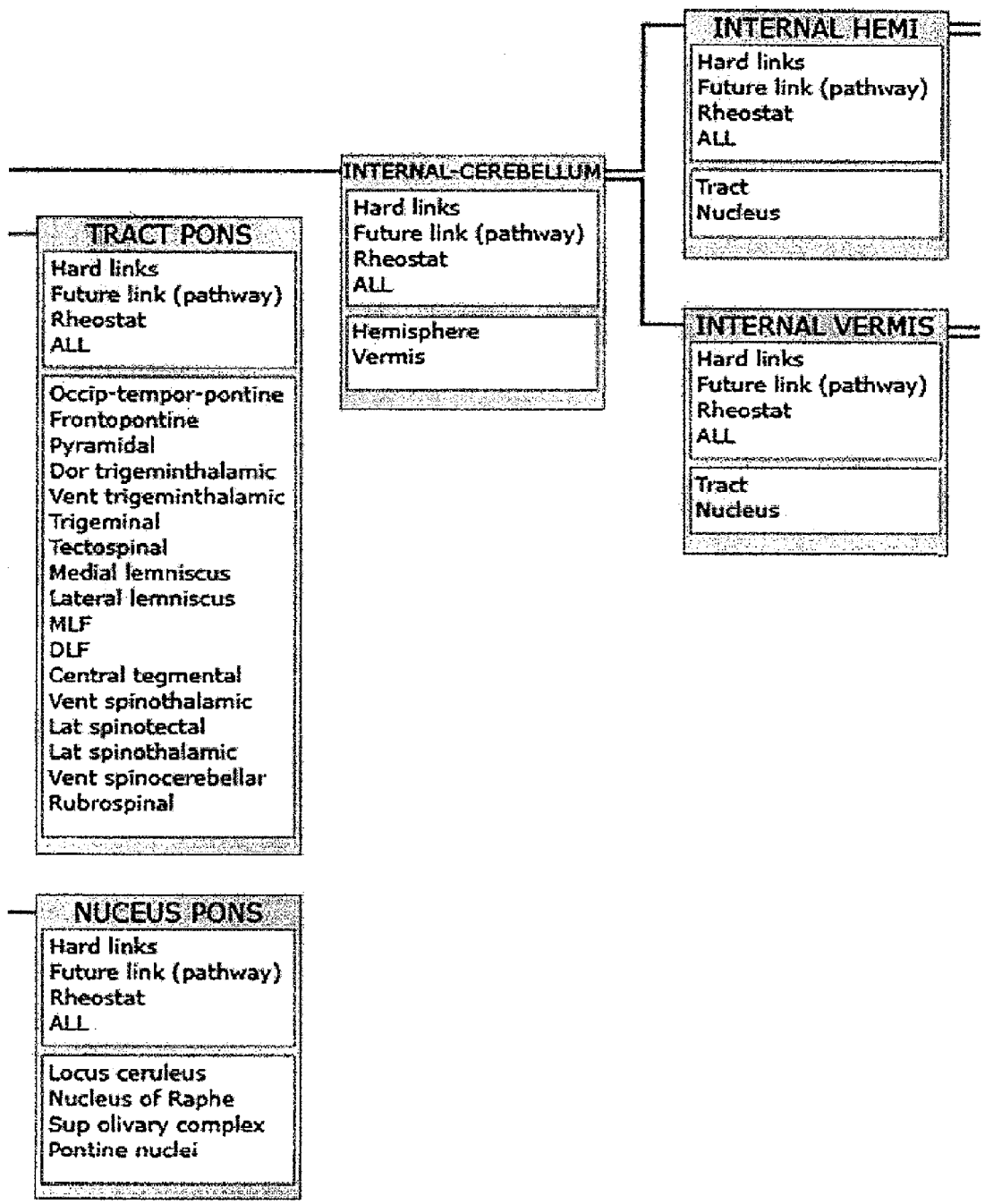
FIG. 7.10

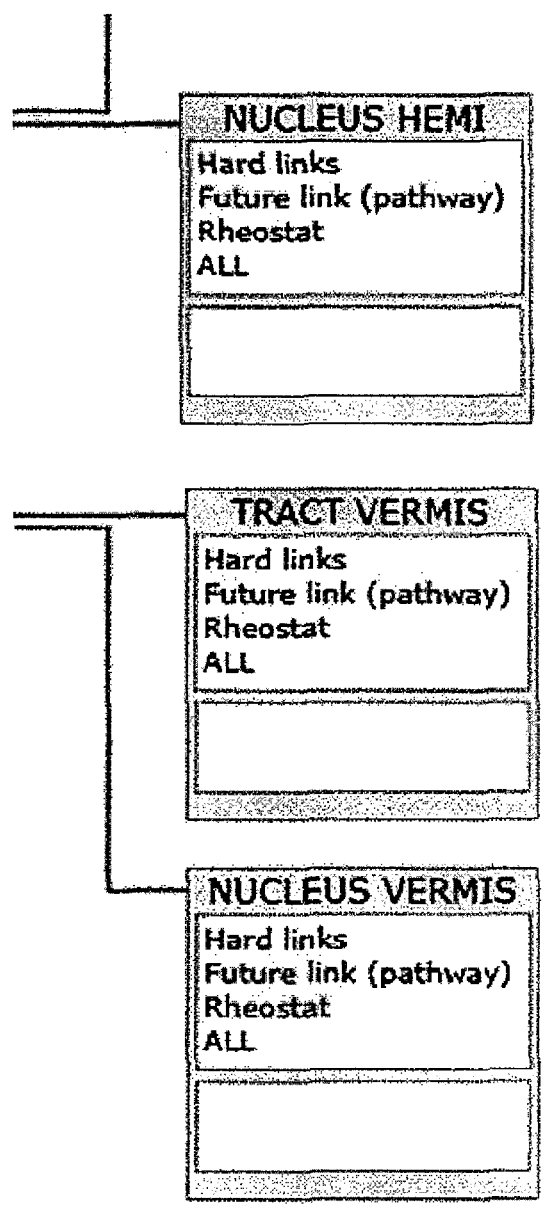
FIG. 7.11

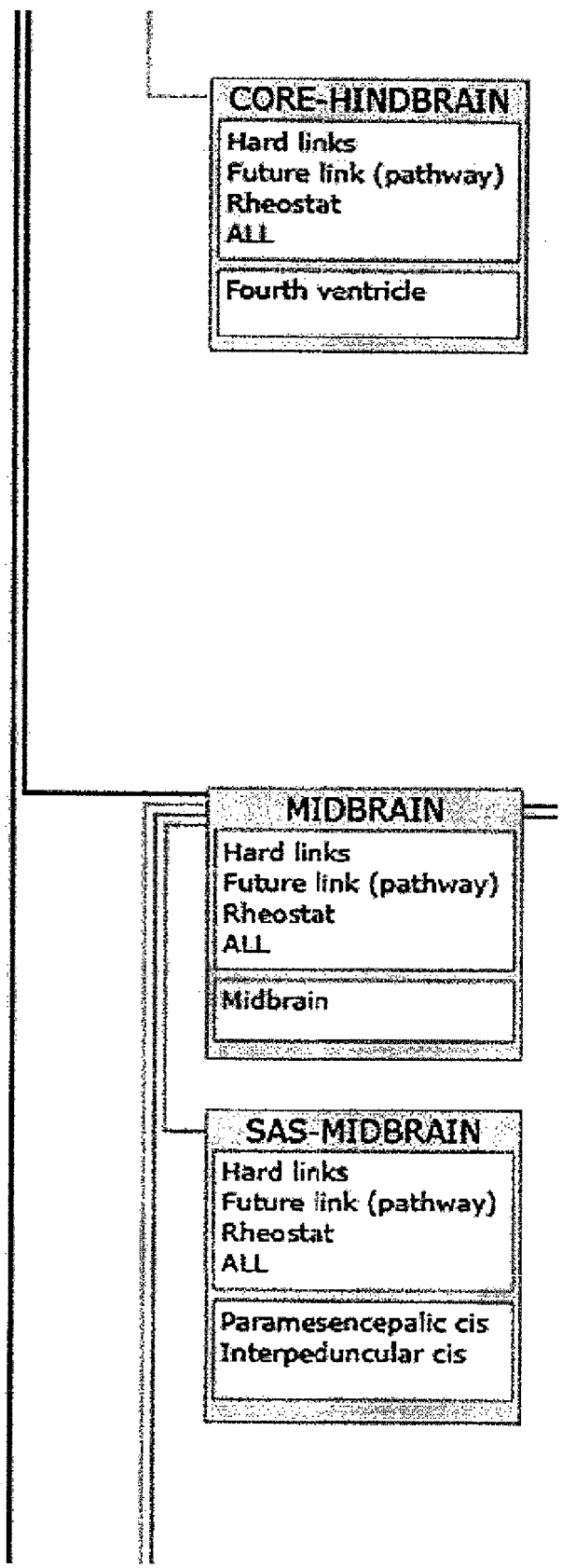
FIG. 7.12

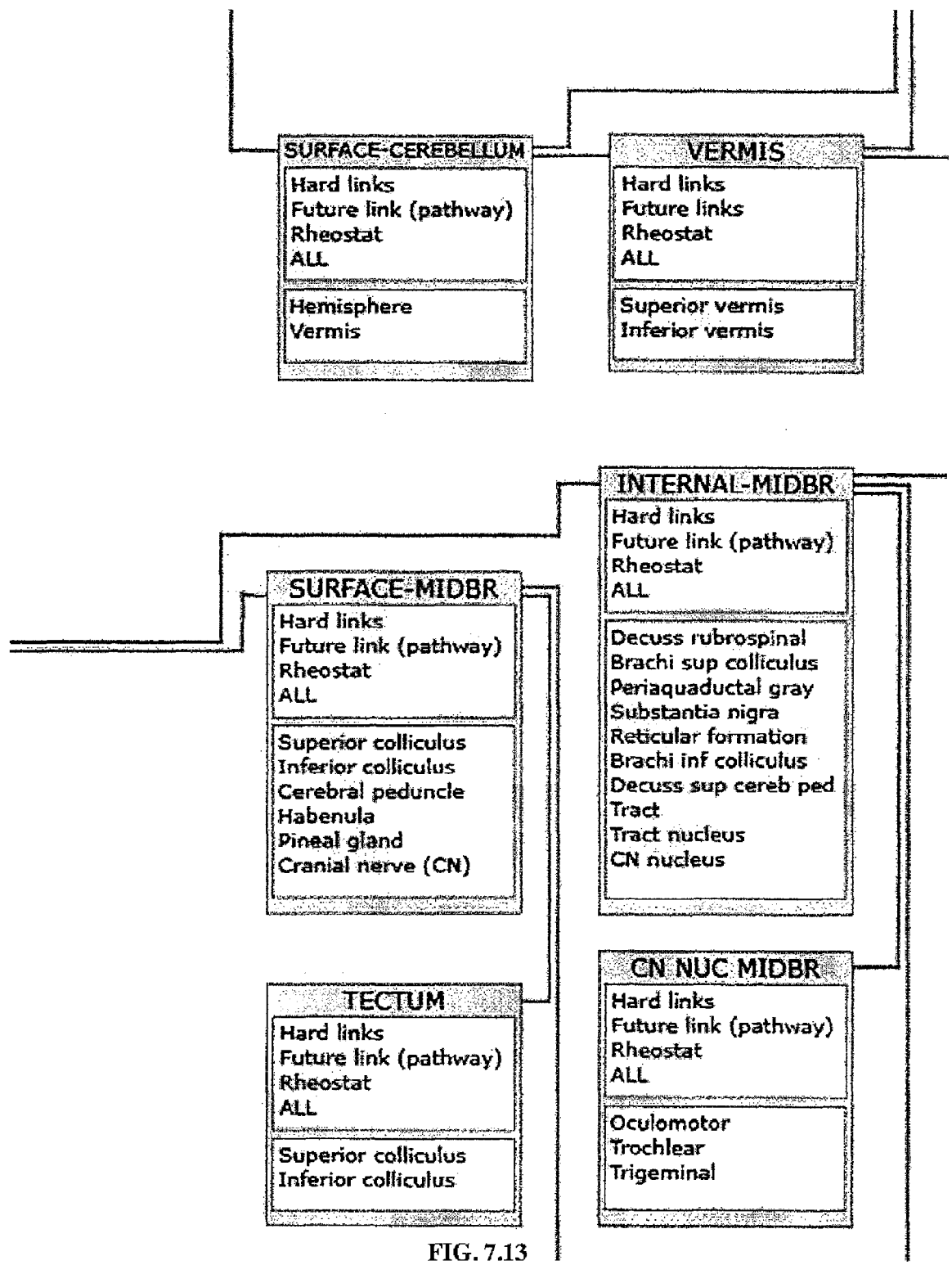
FIG. 7.13

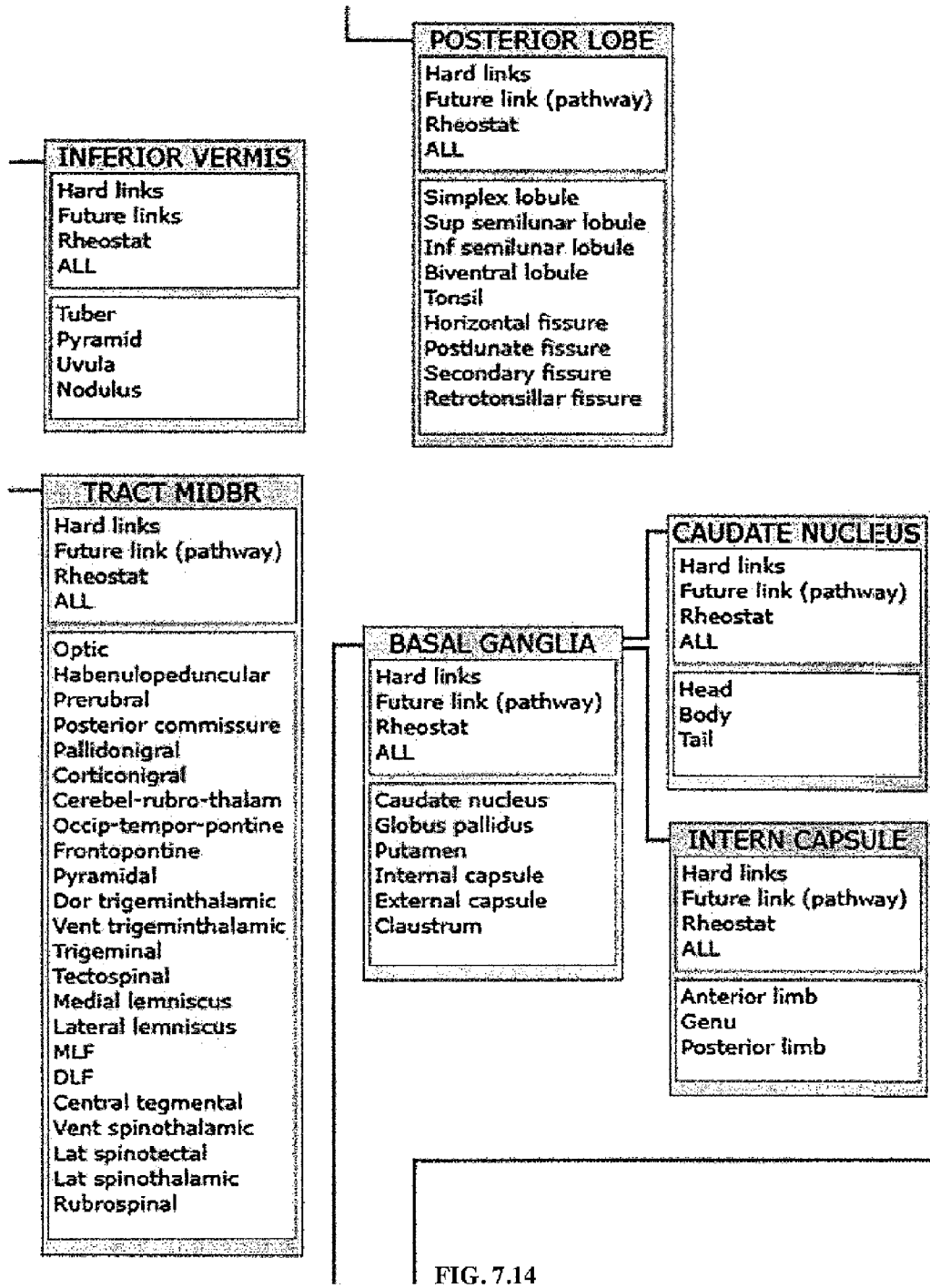
FIG. 7.14

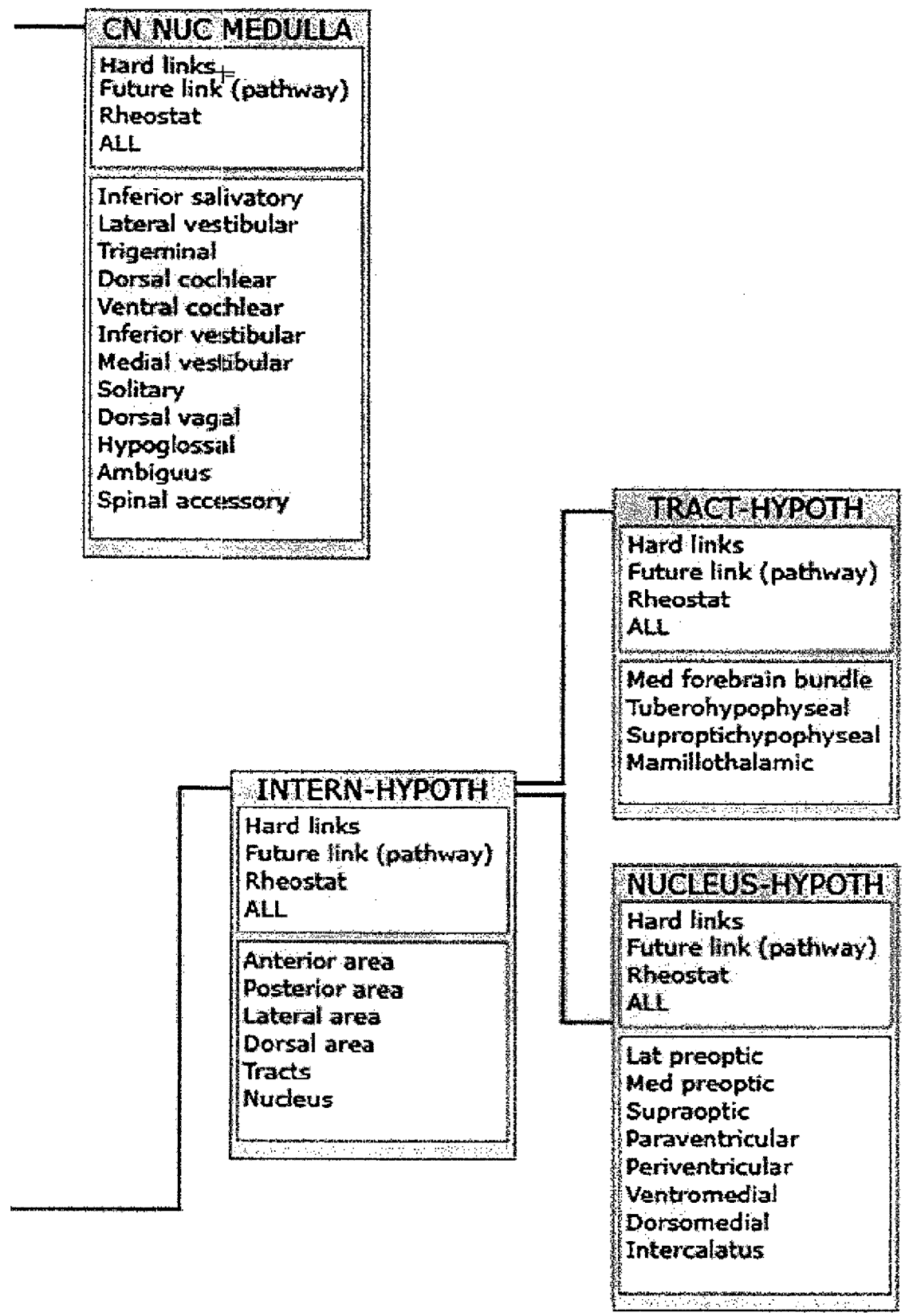
FIG. 7.15

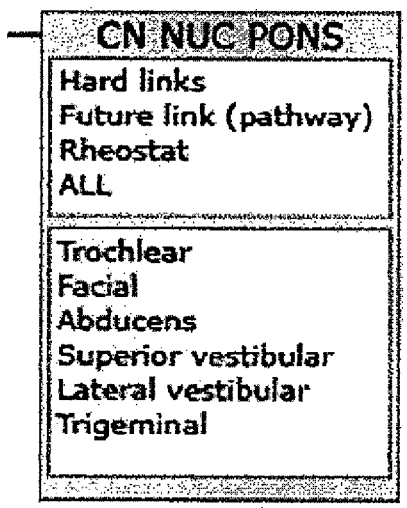
FIG. 7.16

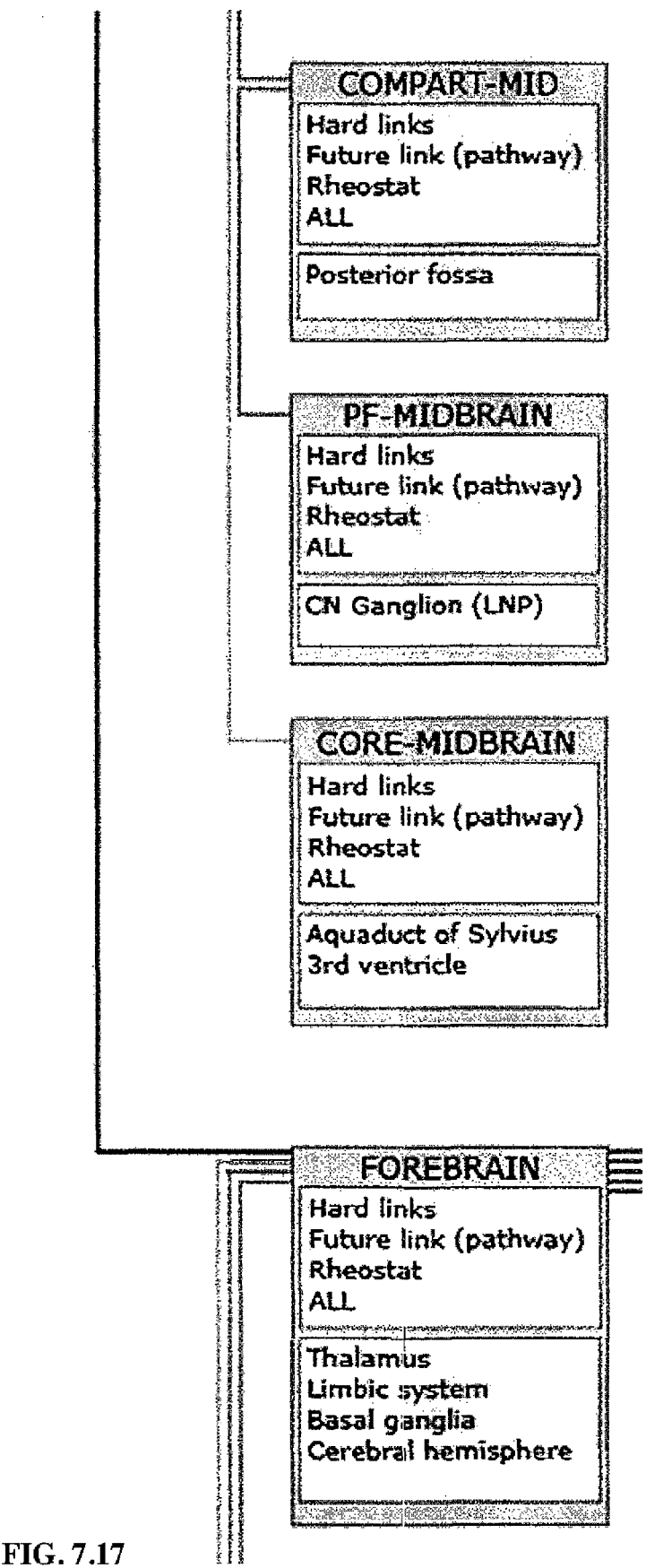
FIG. 7.17

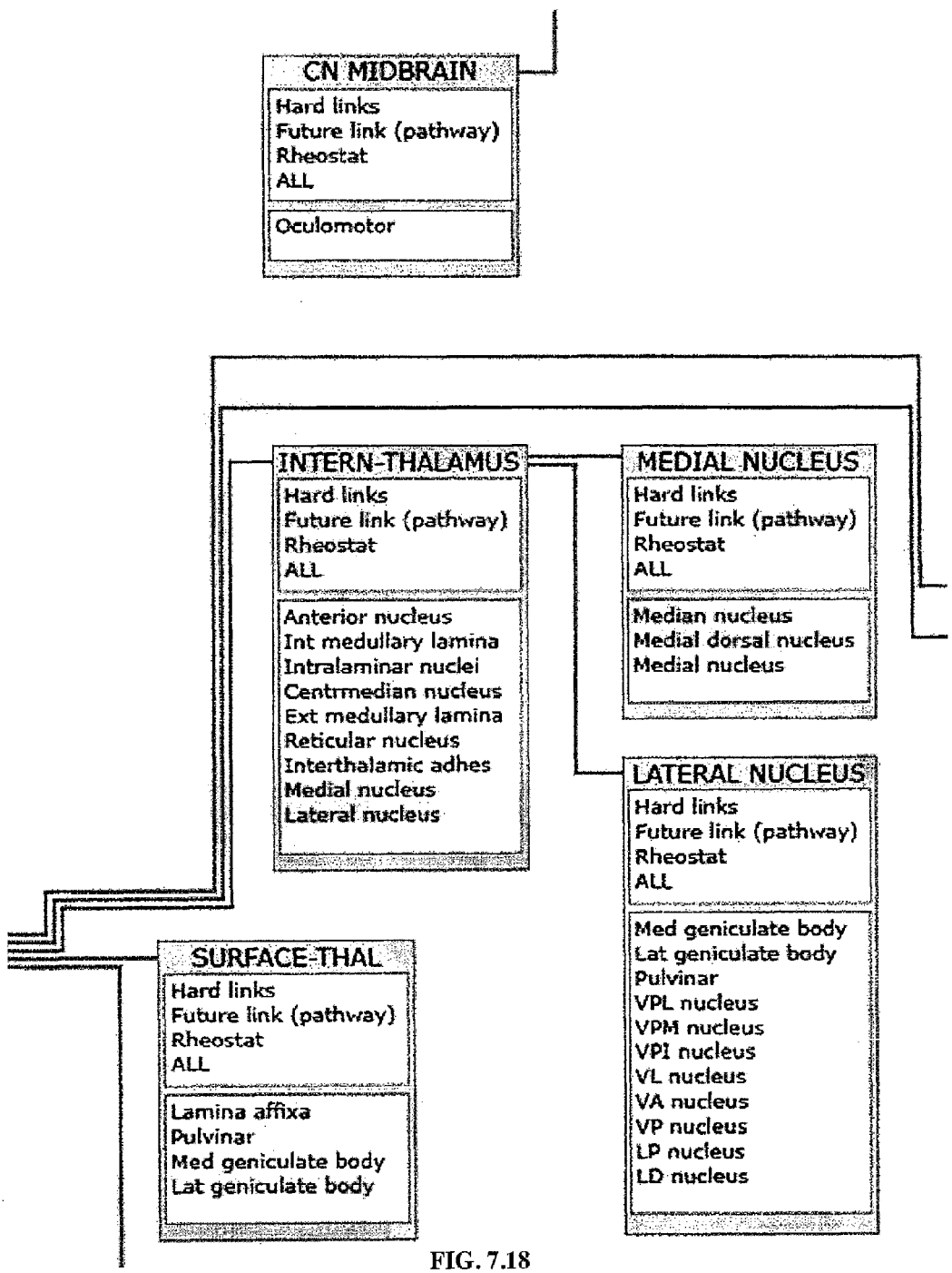
FIG. 7.18

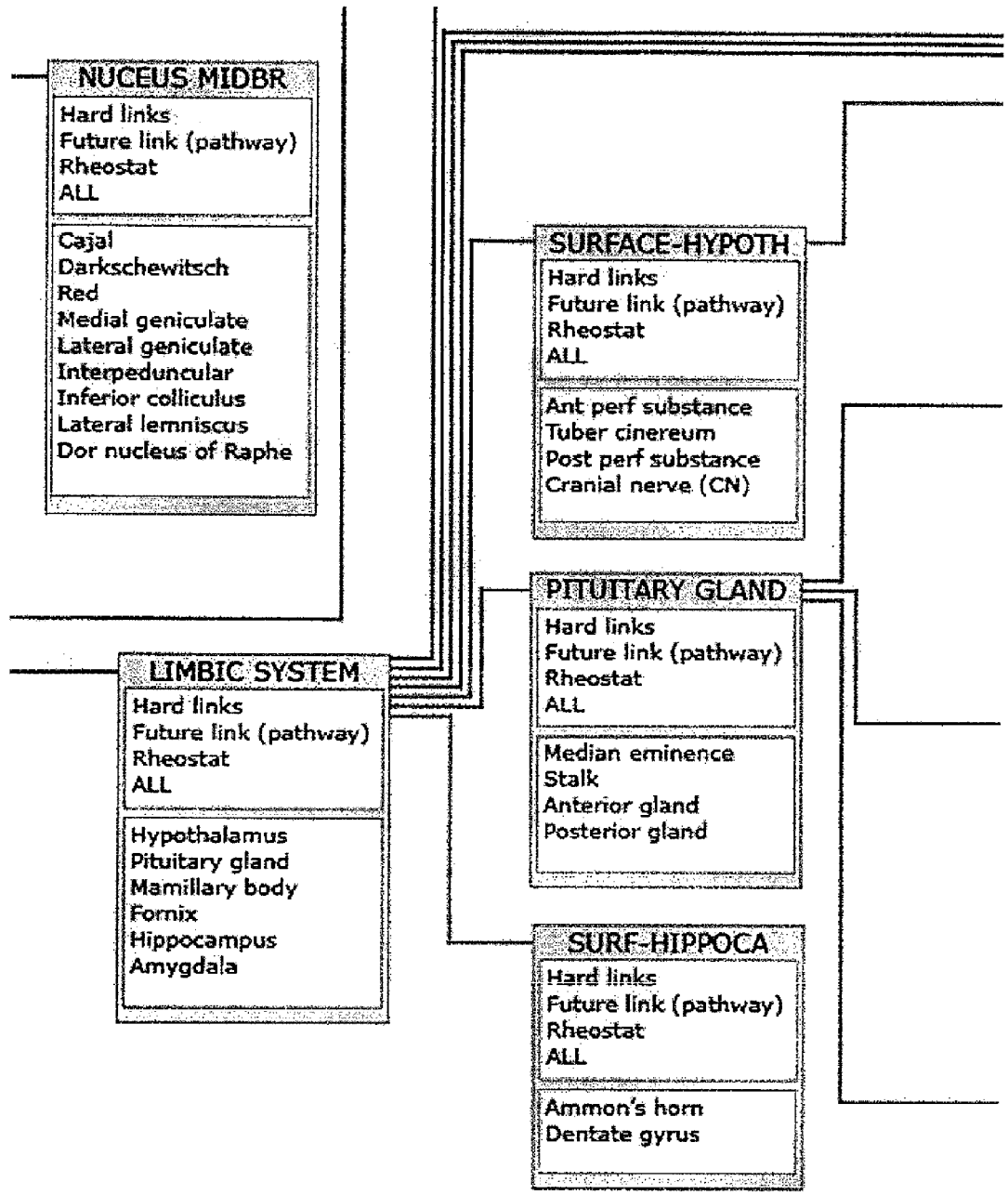
FIG. 7.19

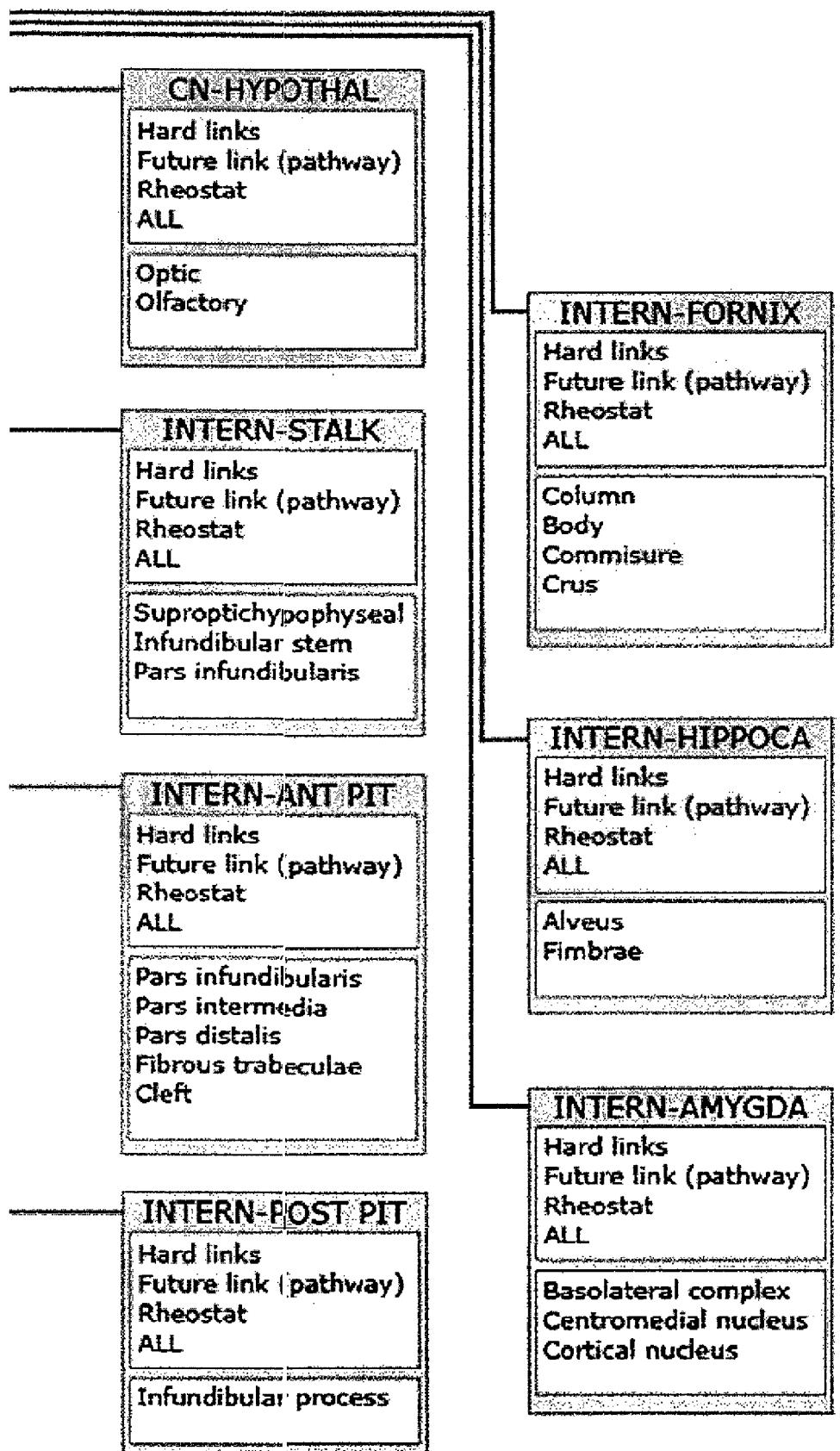
FIG. 7.20

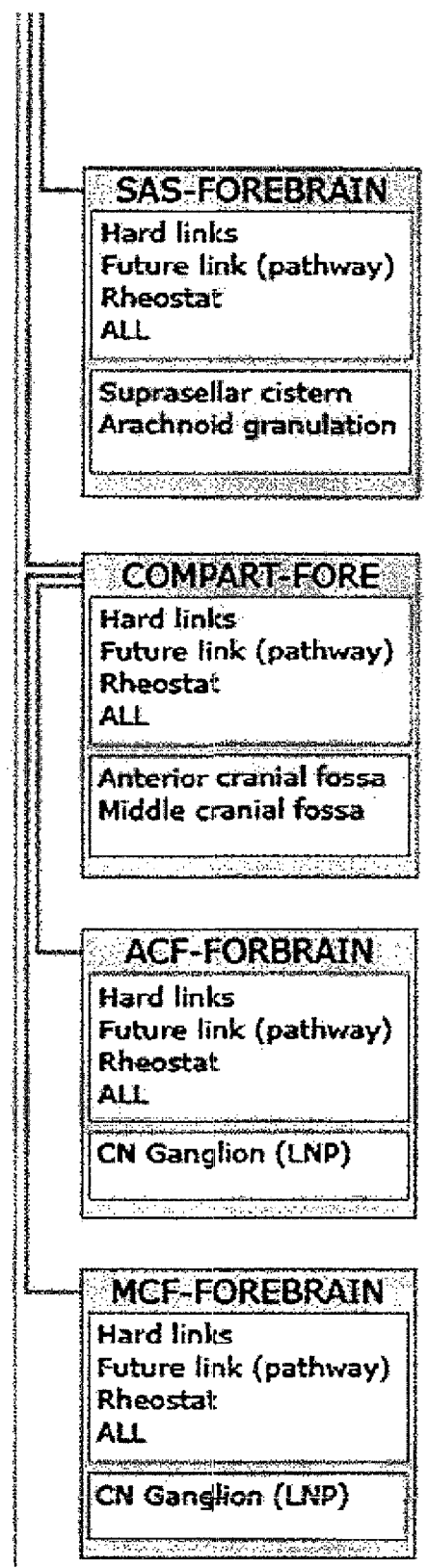
FIG. 7.21

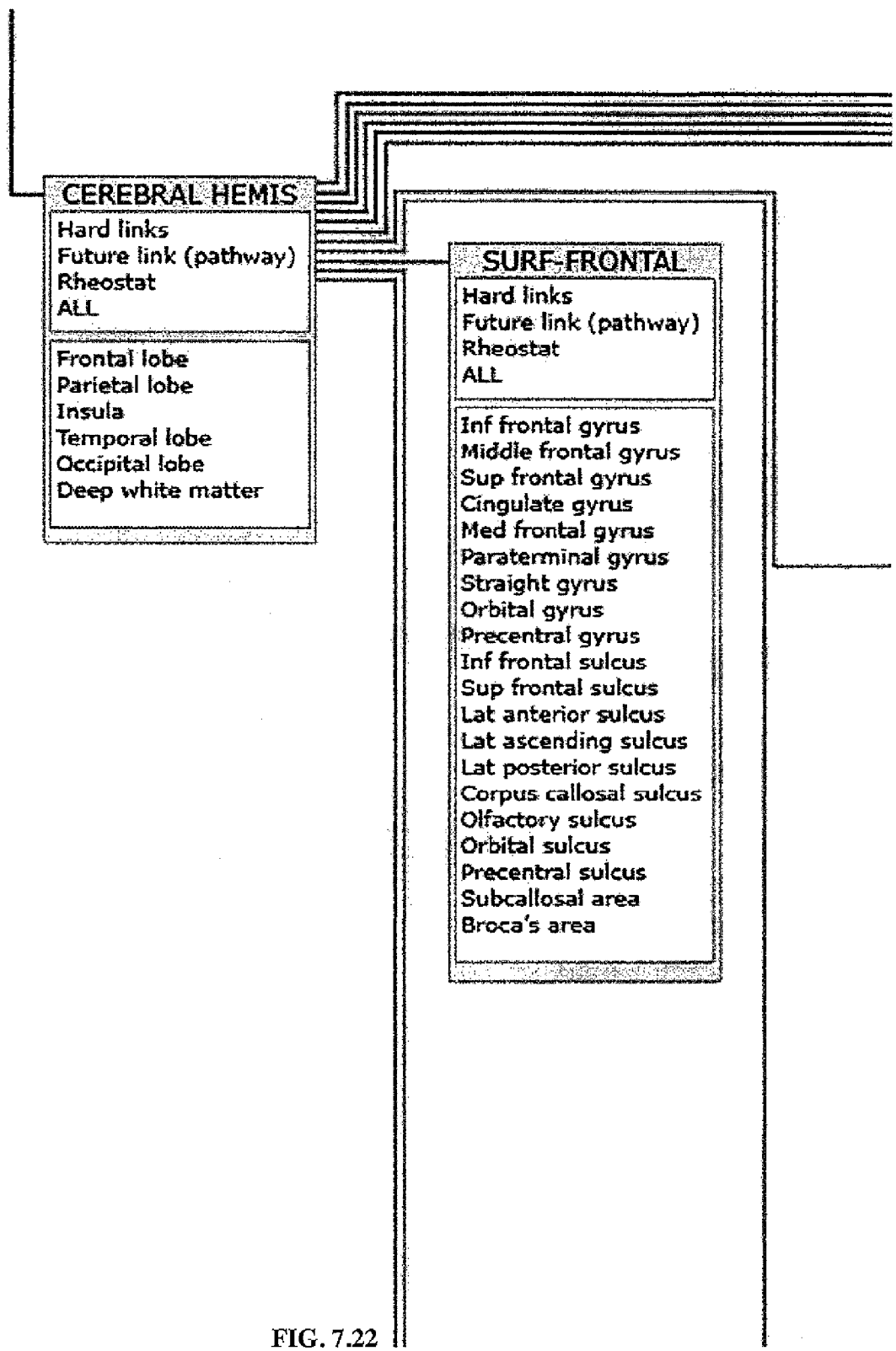
FIG. 7.22

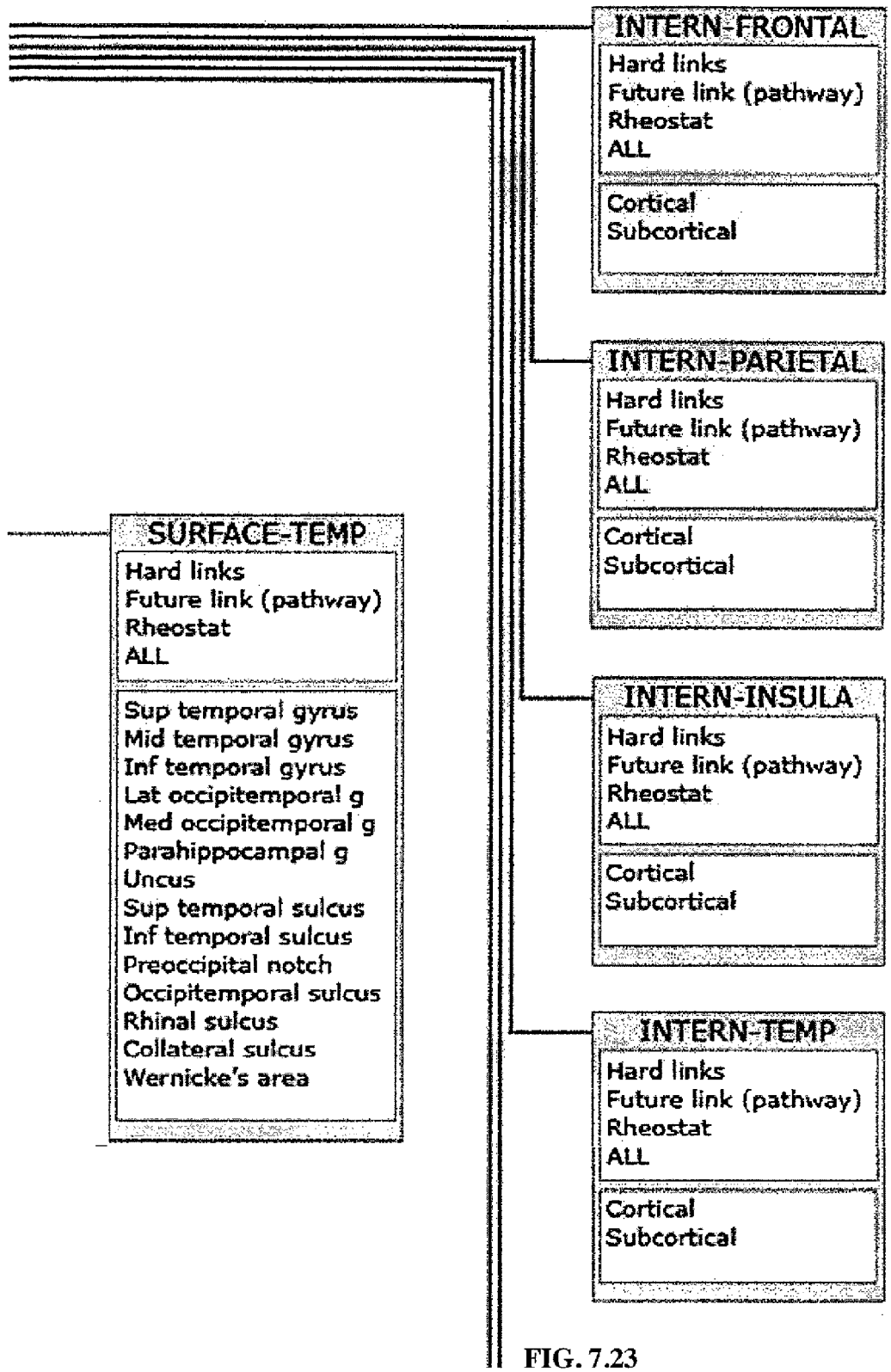
FIG. 7.23

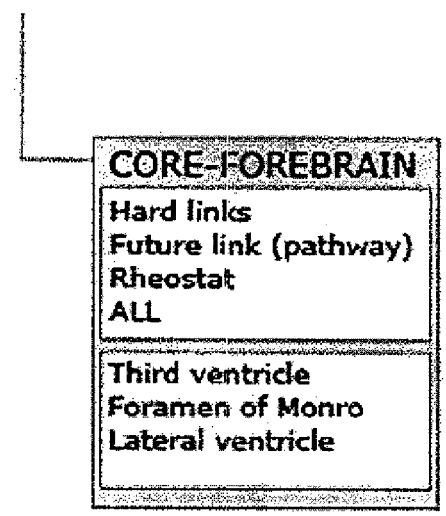
FIG. 7.24

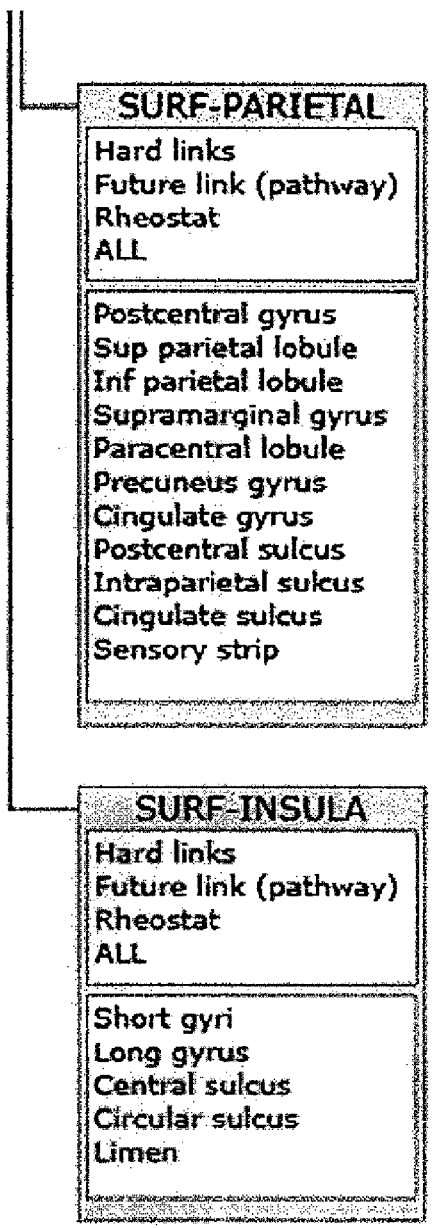
FIG. 7.25

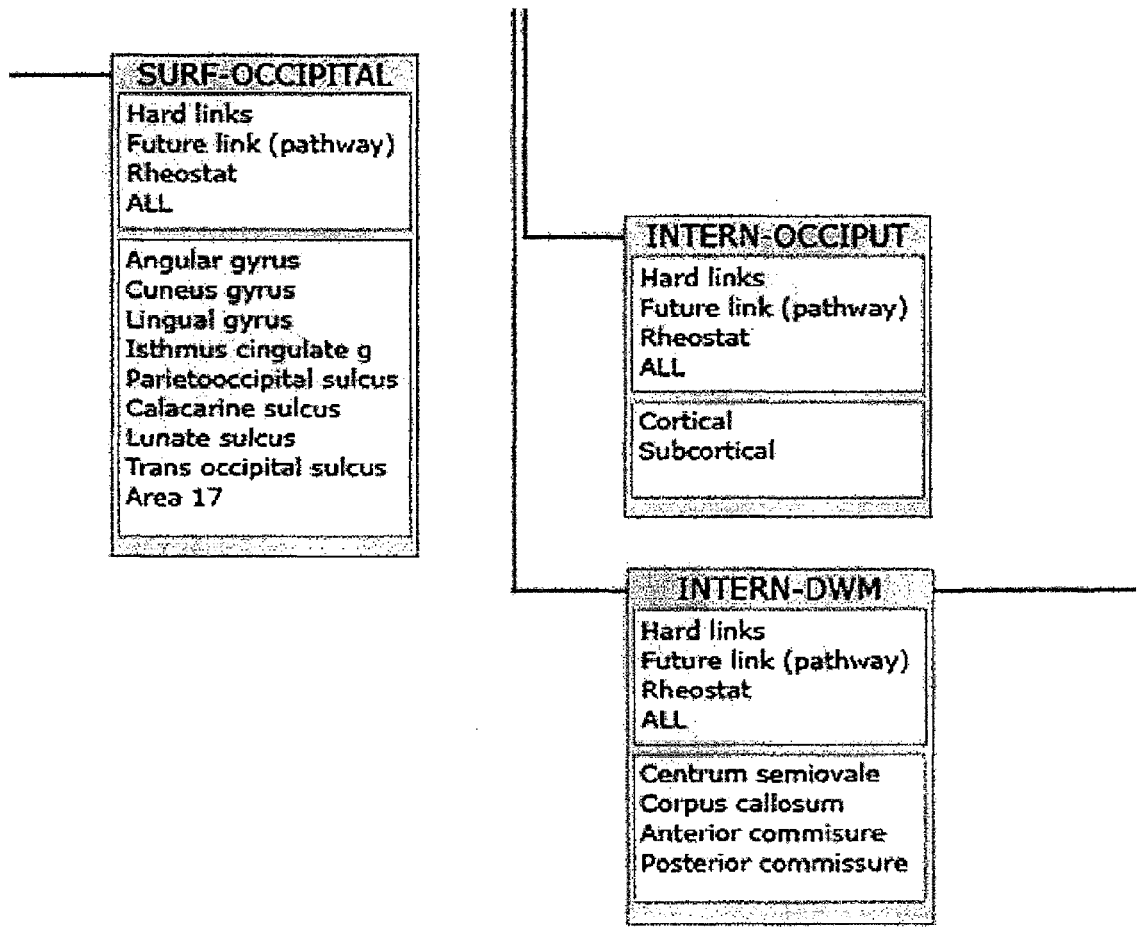
FIG. 7.26

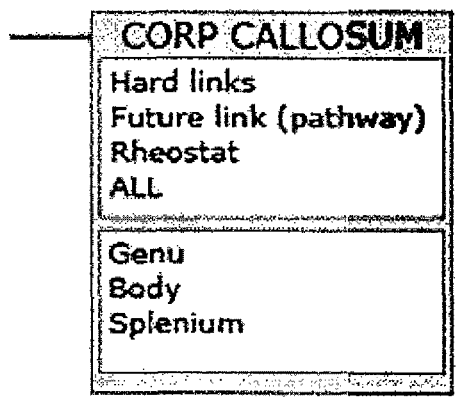
FIG. 7.27

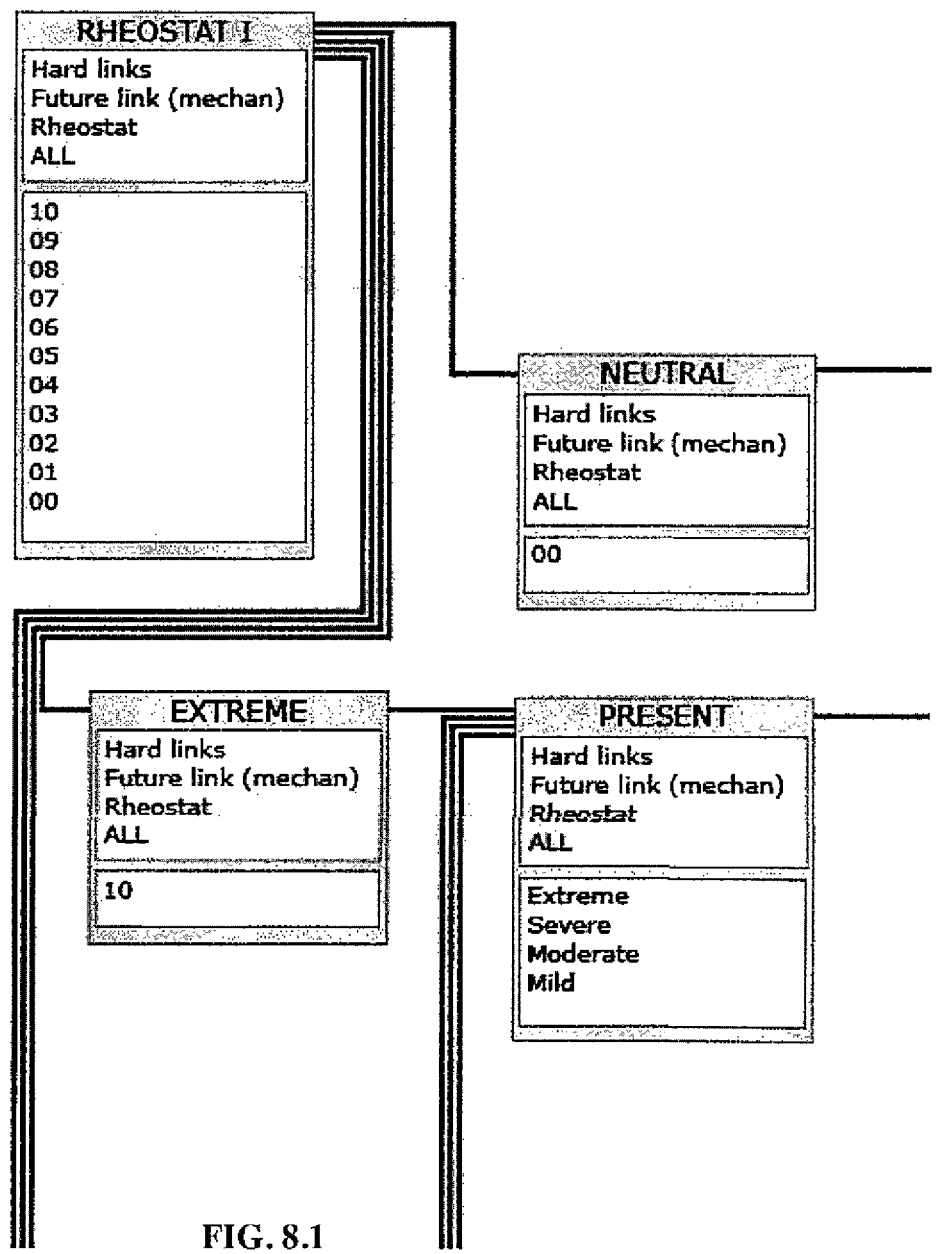
FIG. 8.1

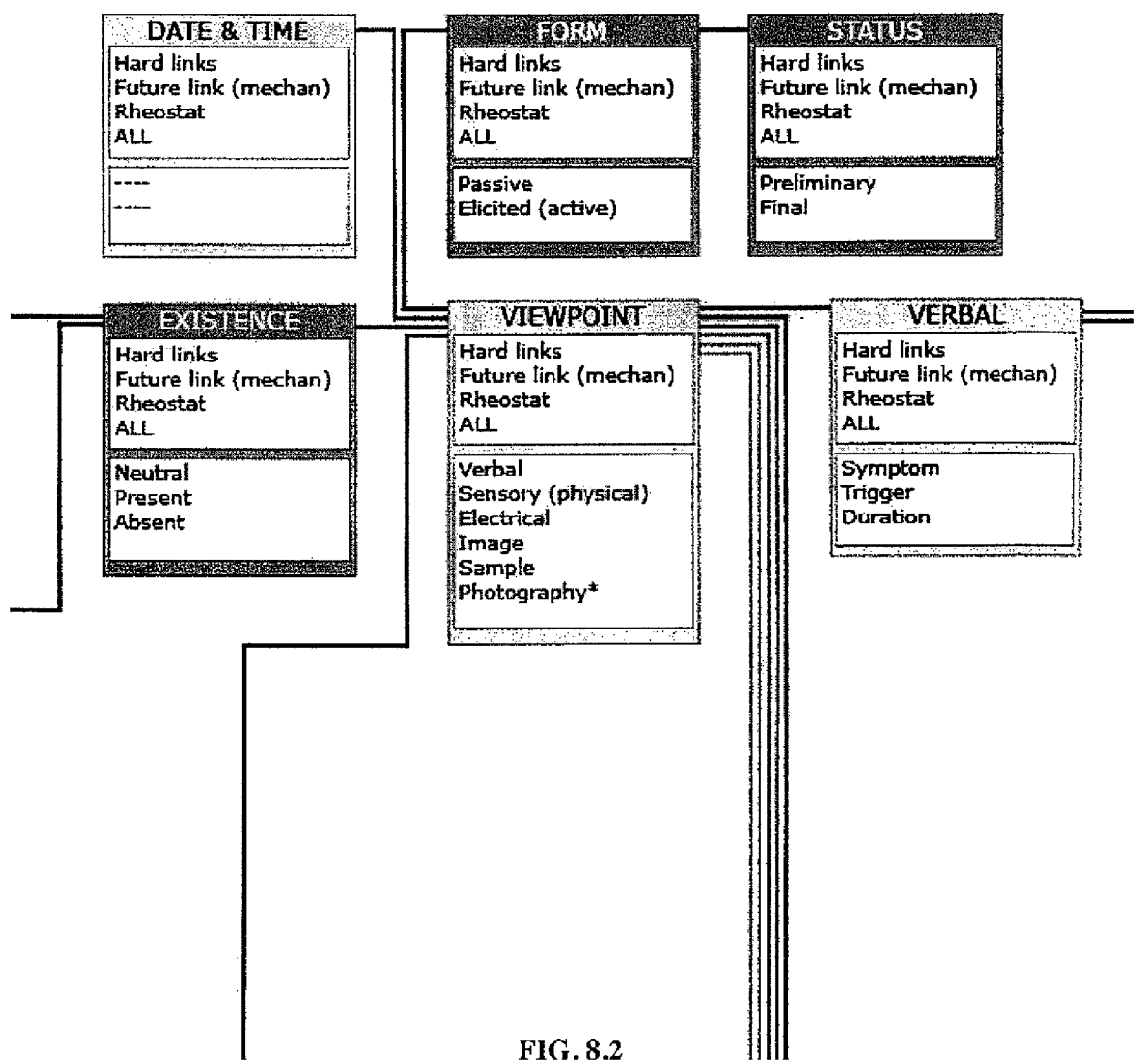
FIG. 8.2

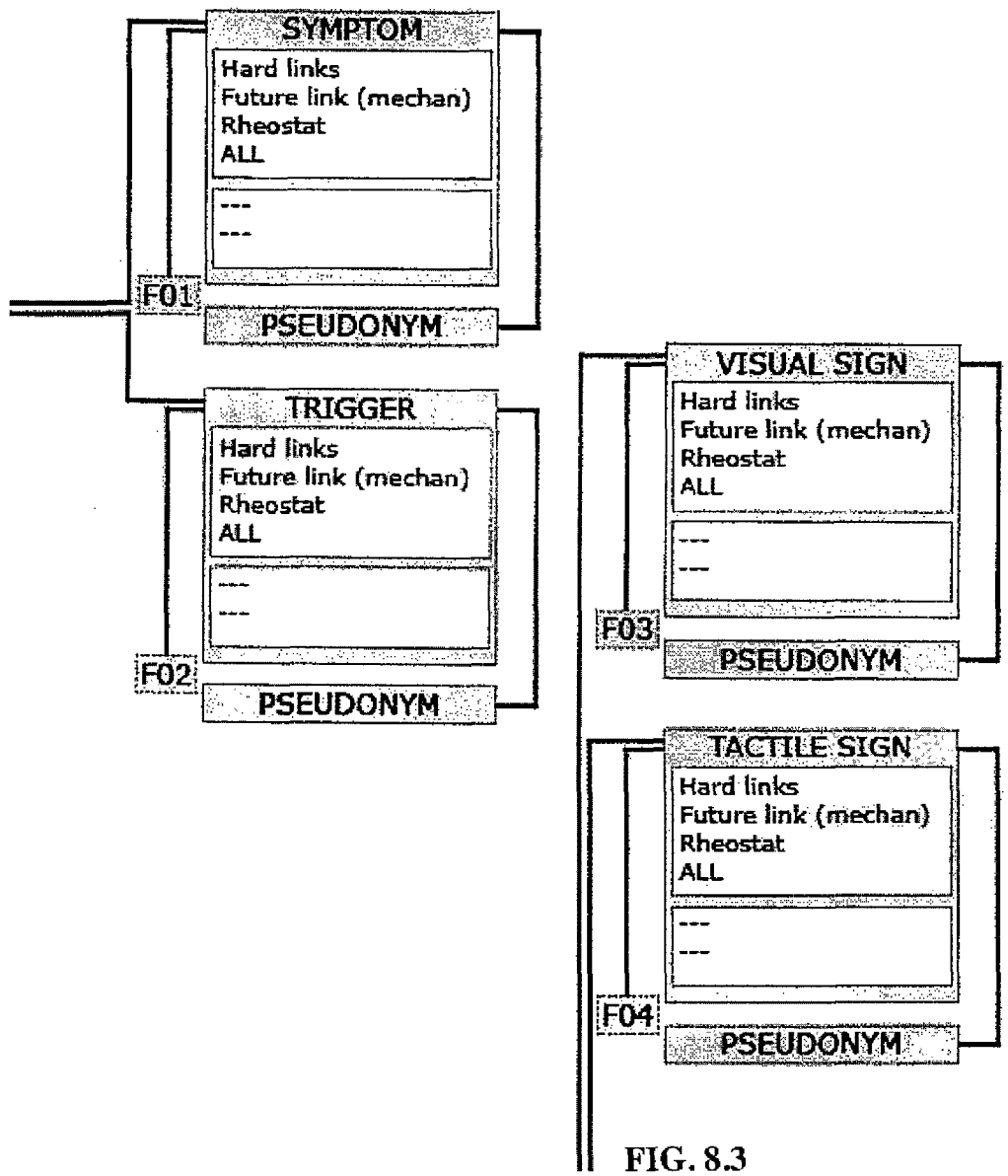
FIG. 8.3

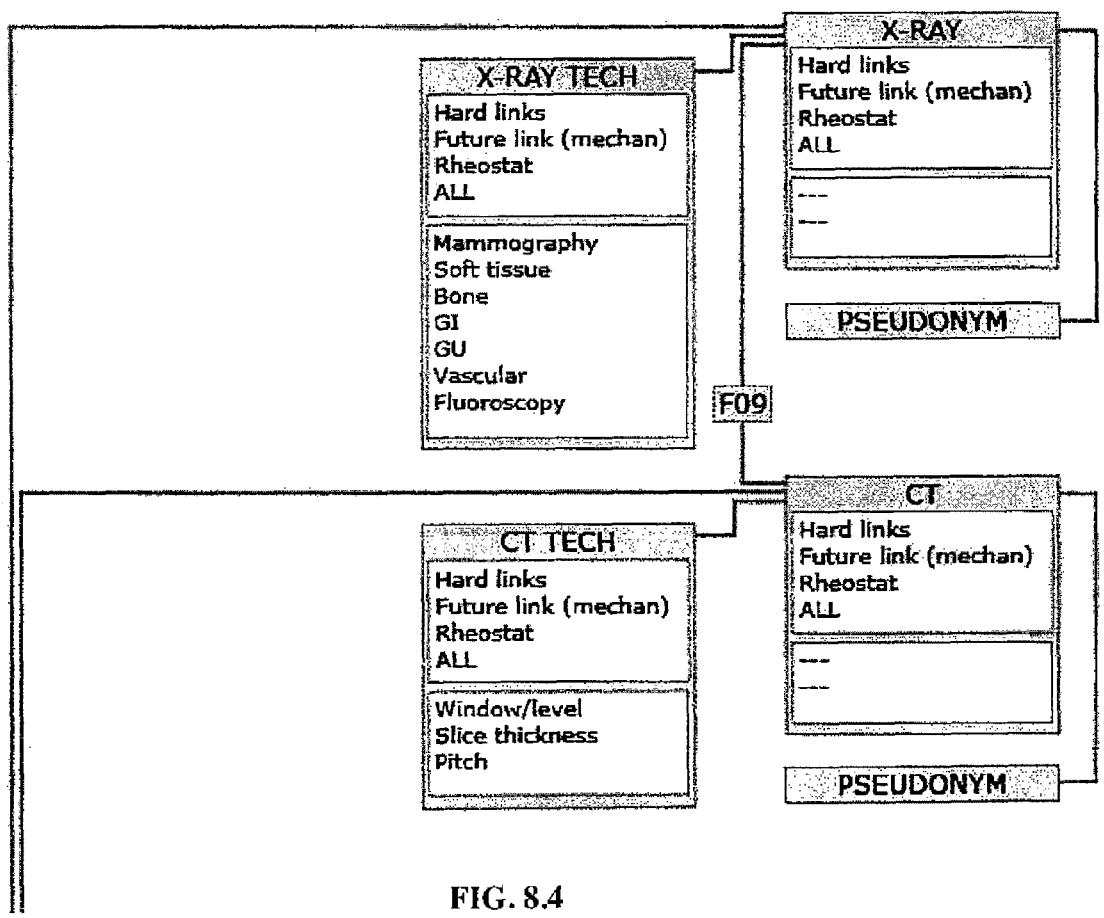
FIG. 8.4

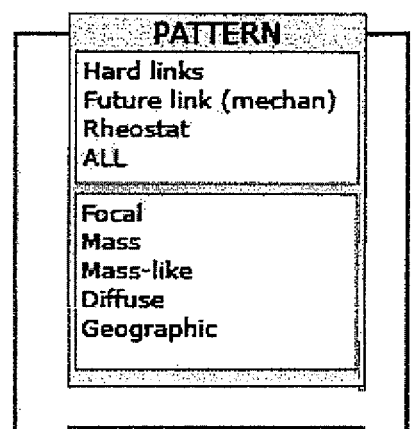
FIG. 8.5

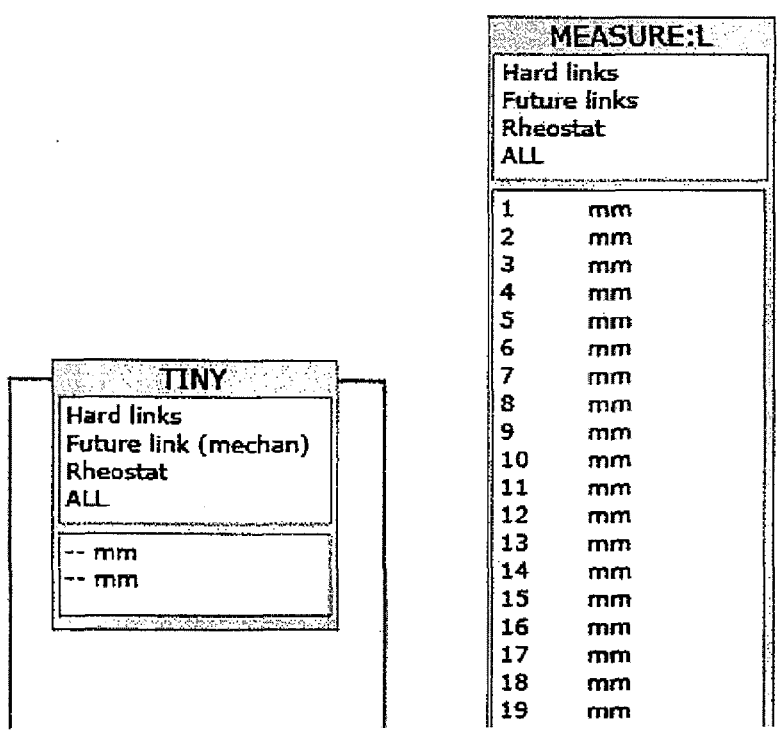
FIG. 8.6

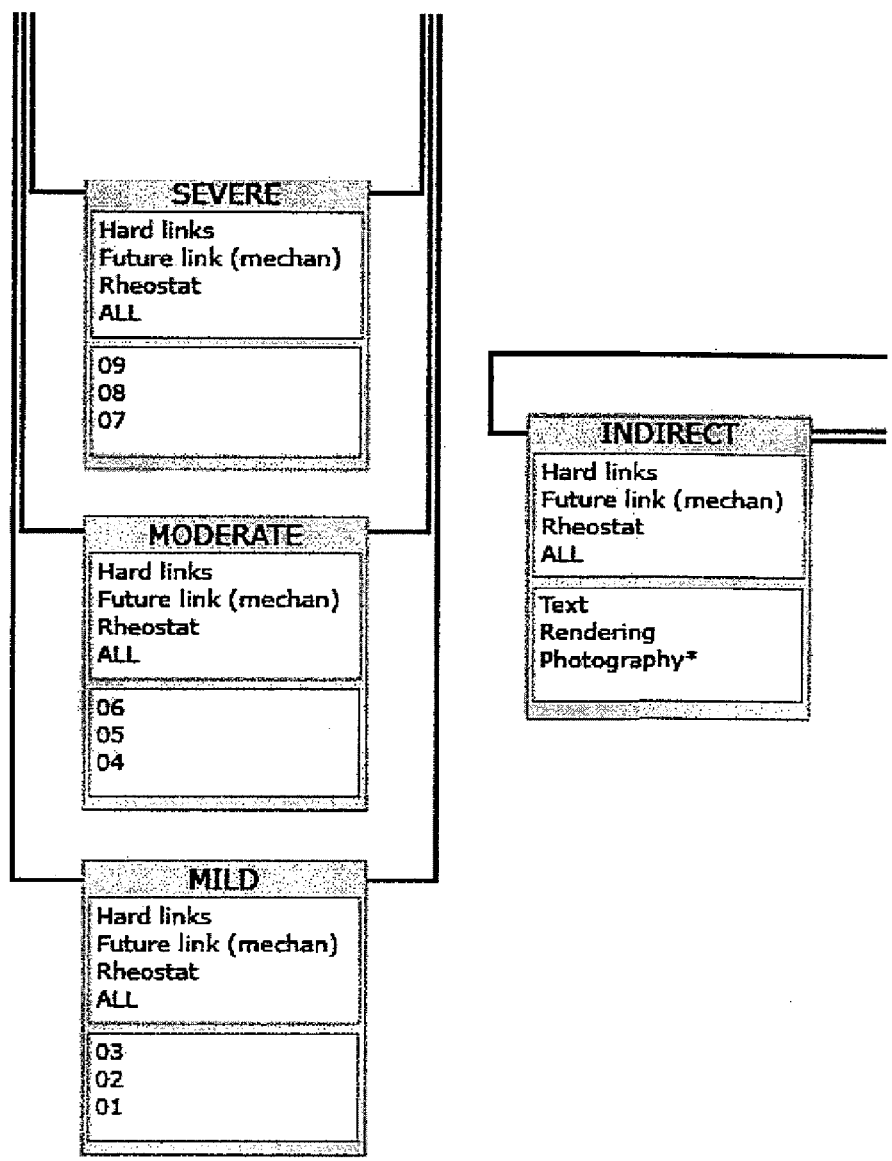
FIG. 8.7

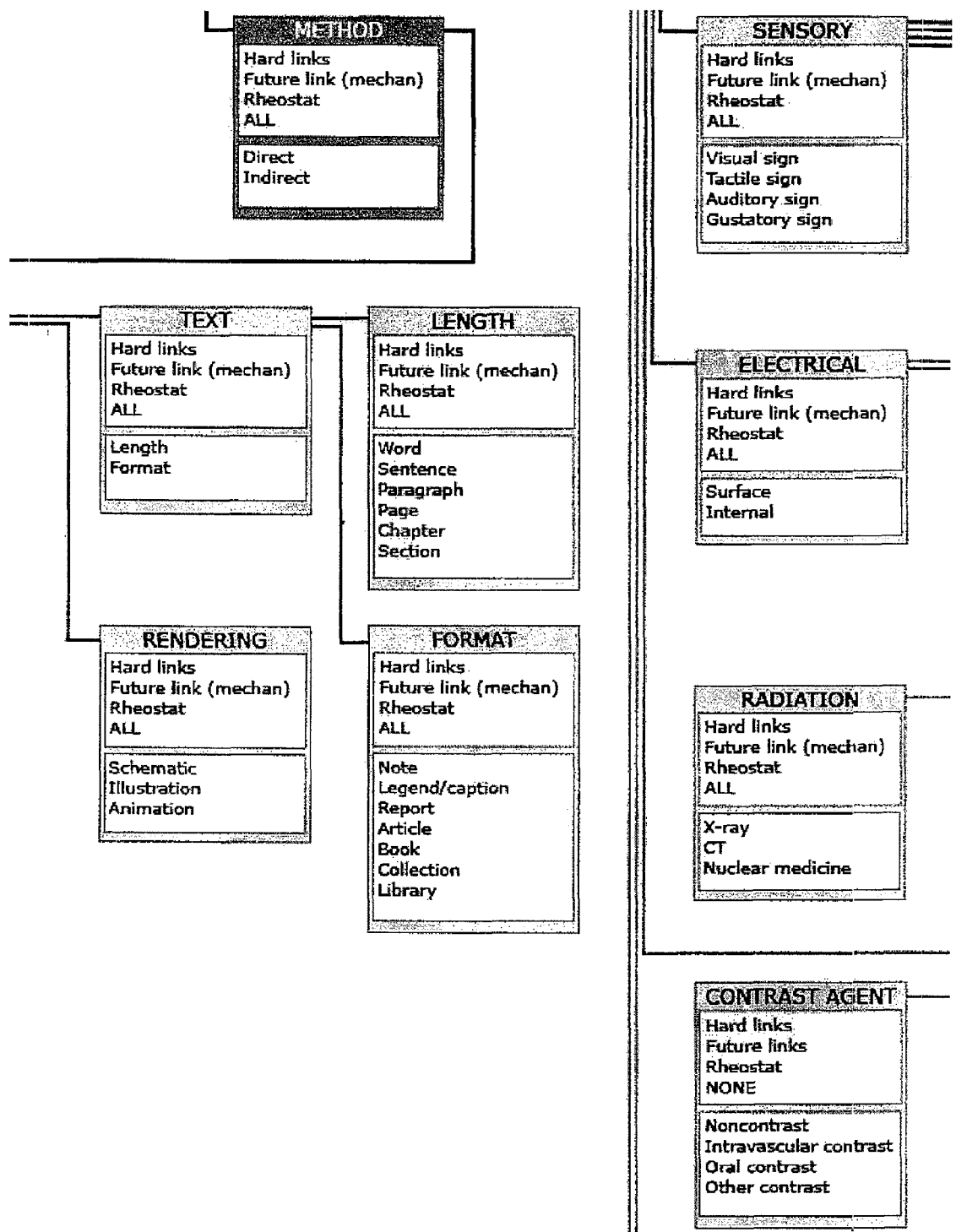
FIG. 8.8

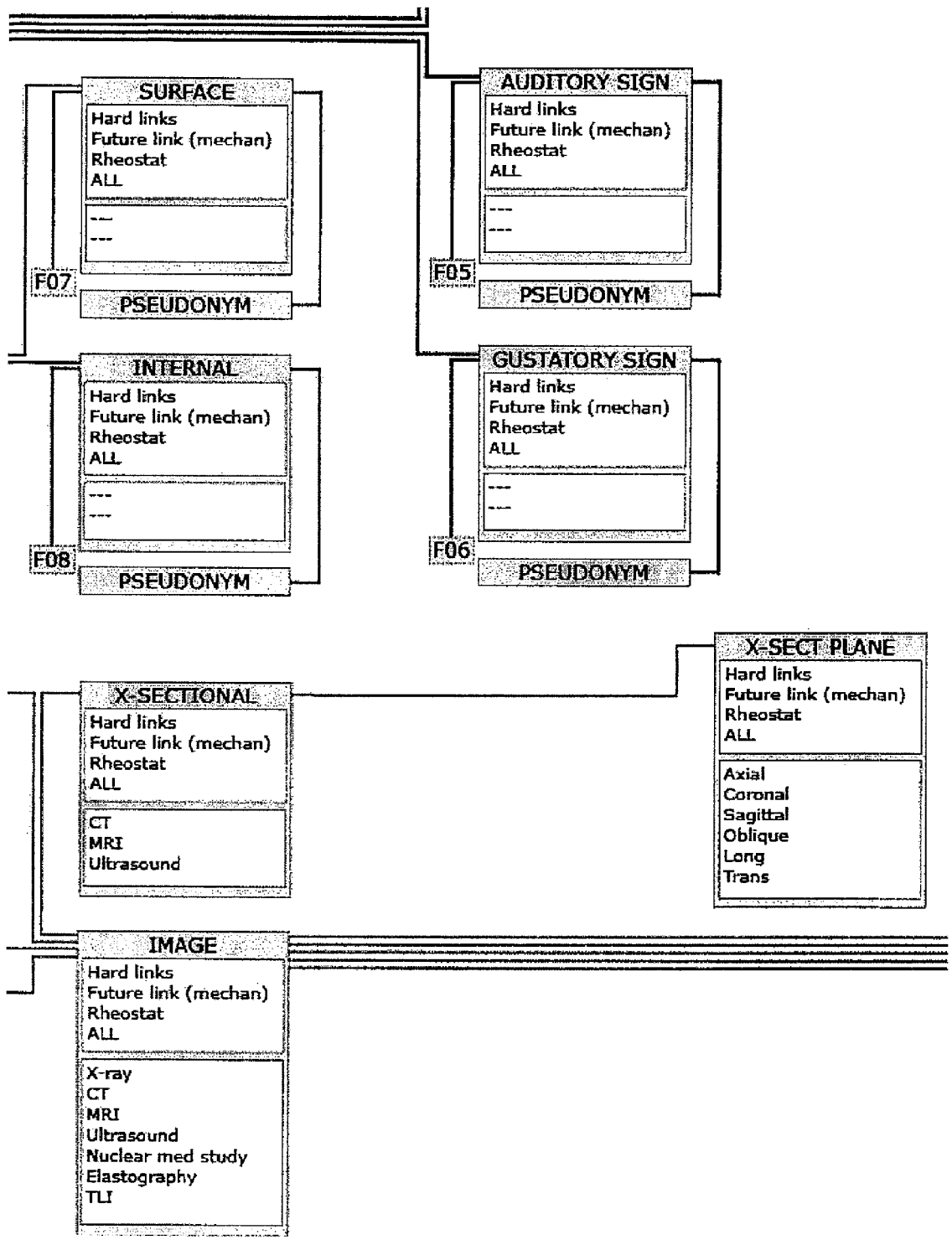
FIG. 8.9

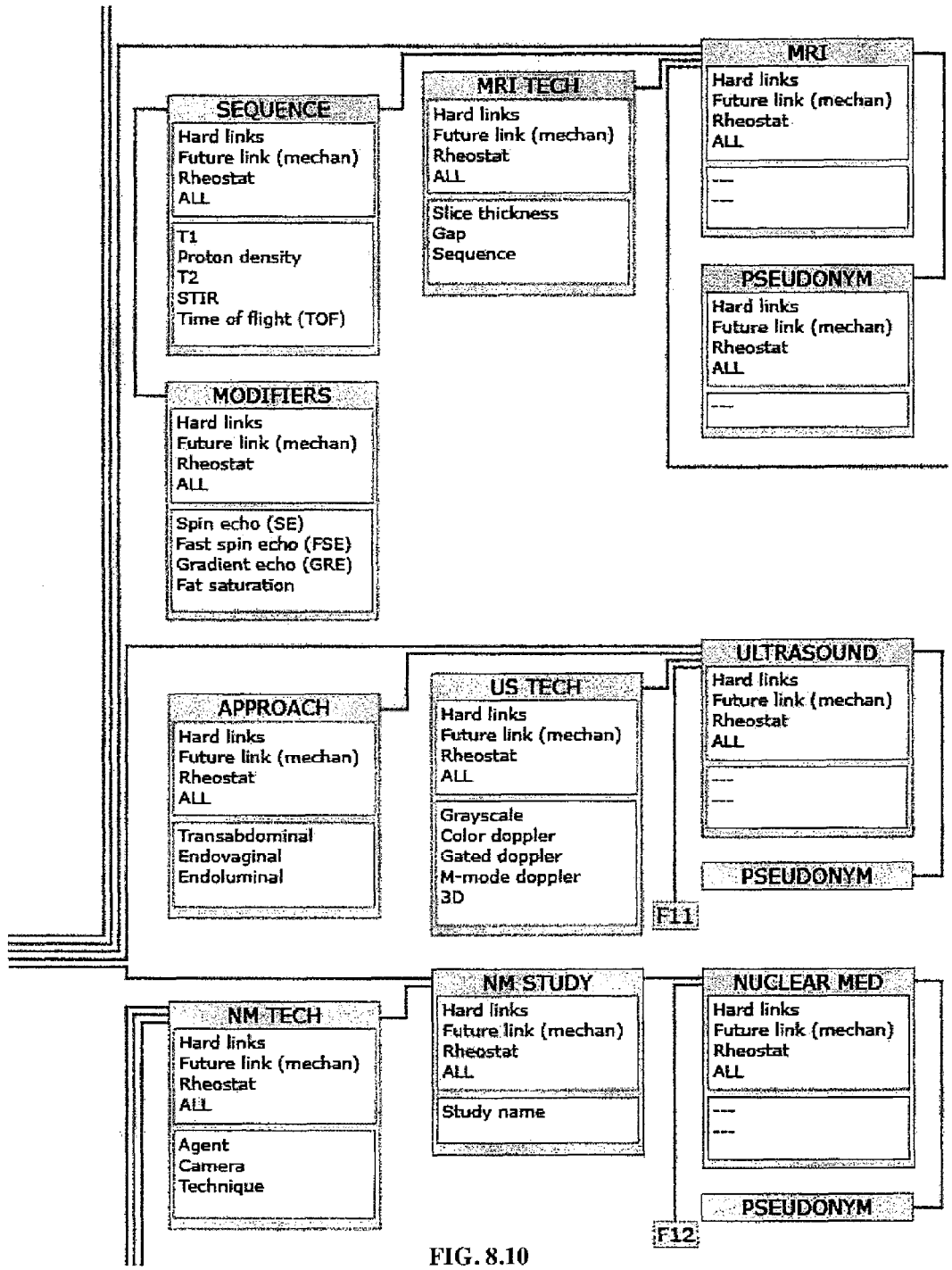
FIG. 8.10

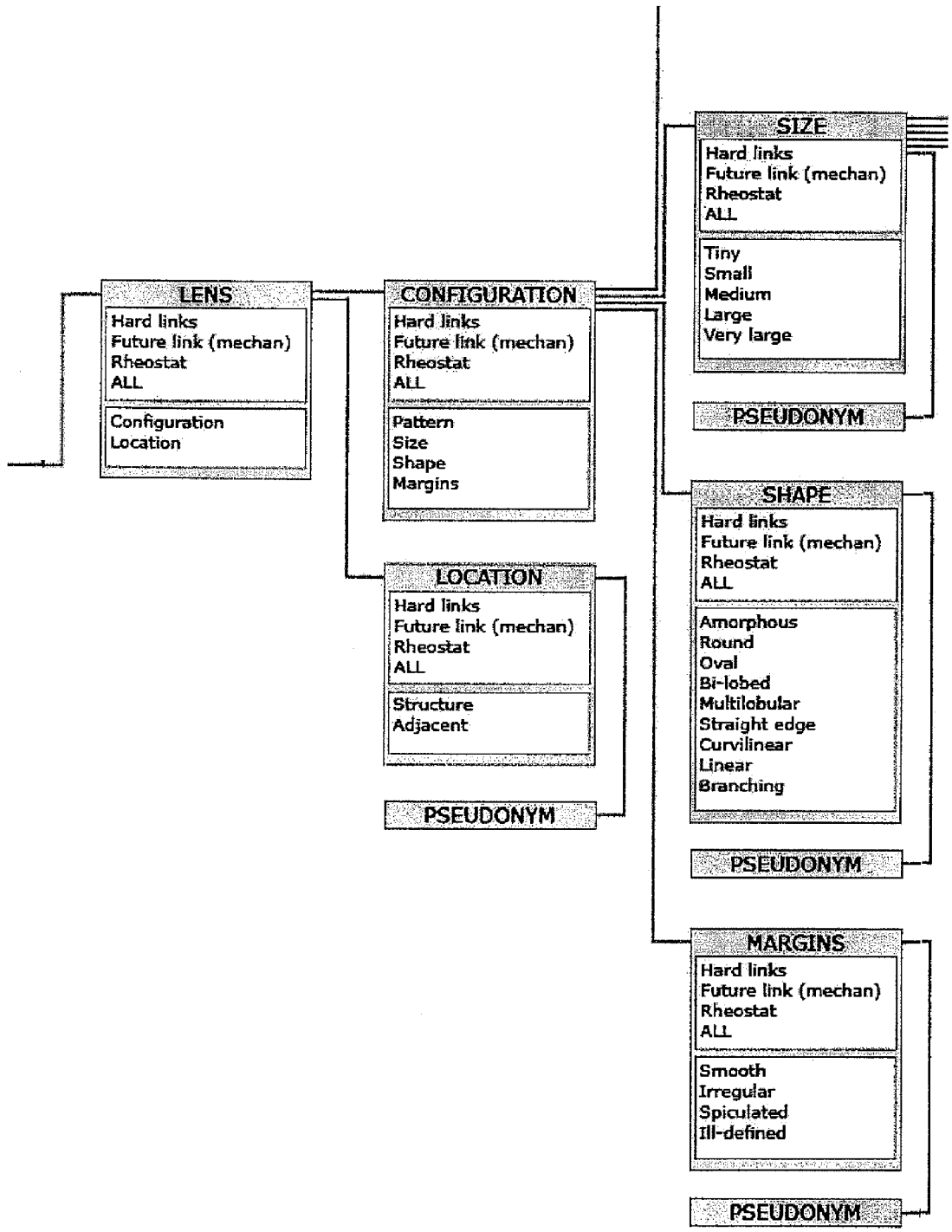
FIG. 8.11

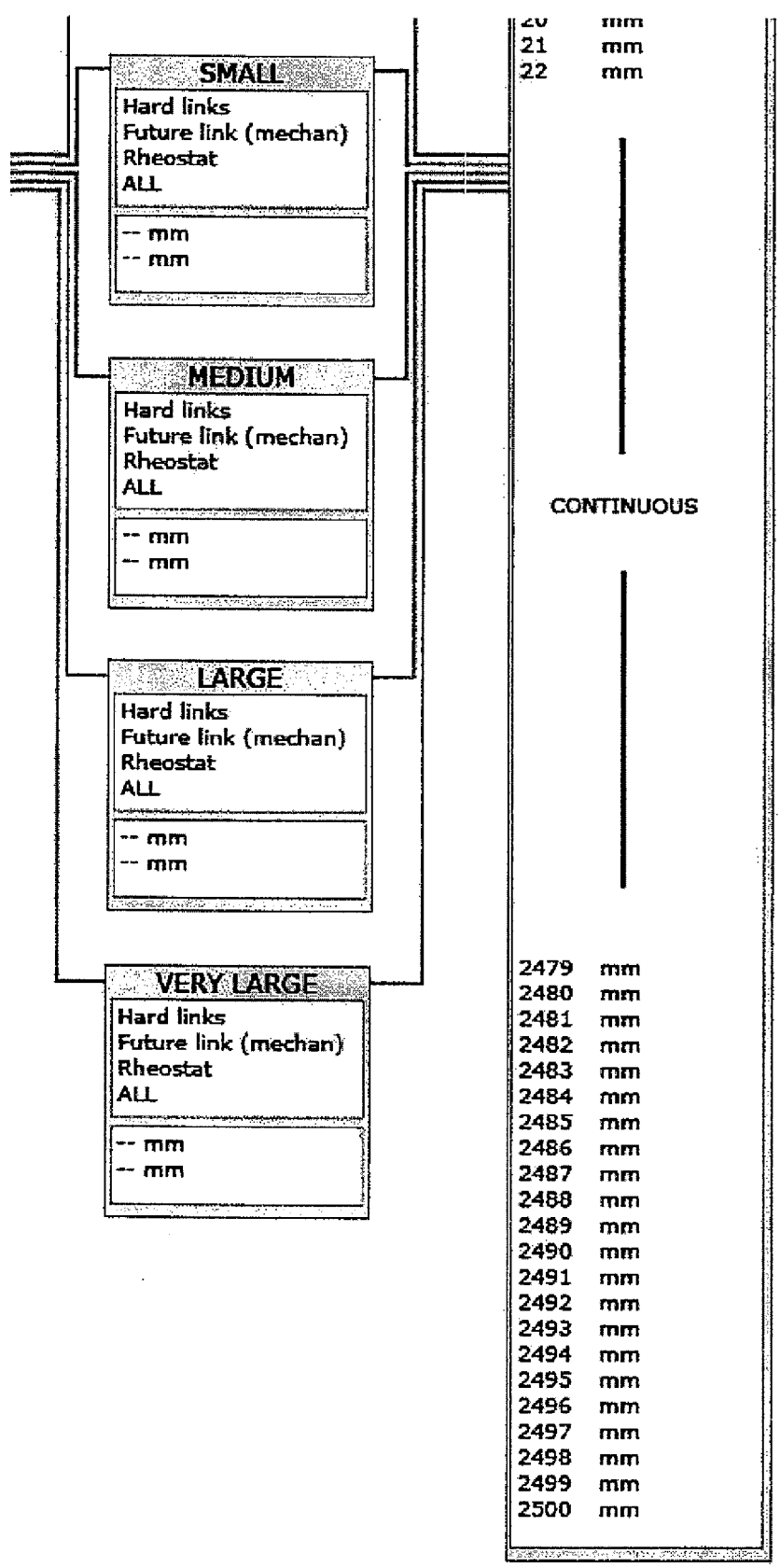
FIG. 8.12

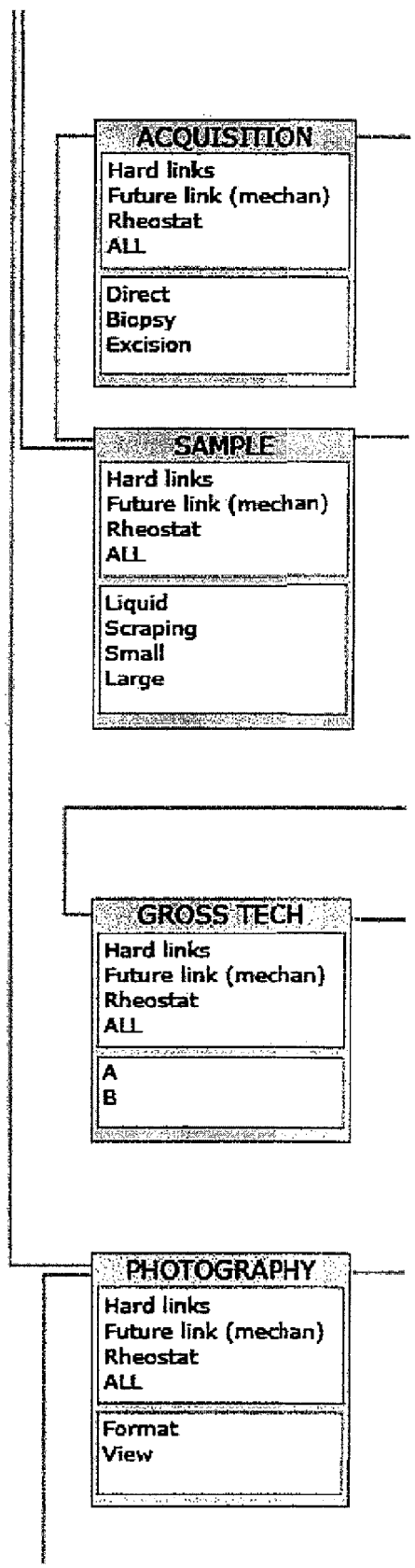
FIG. 8.13

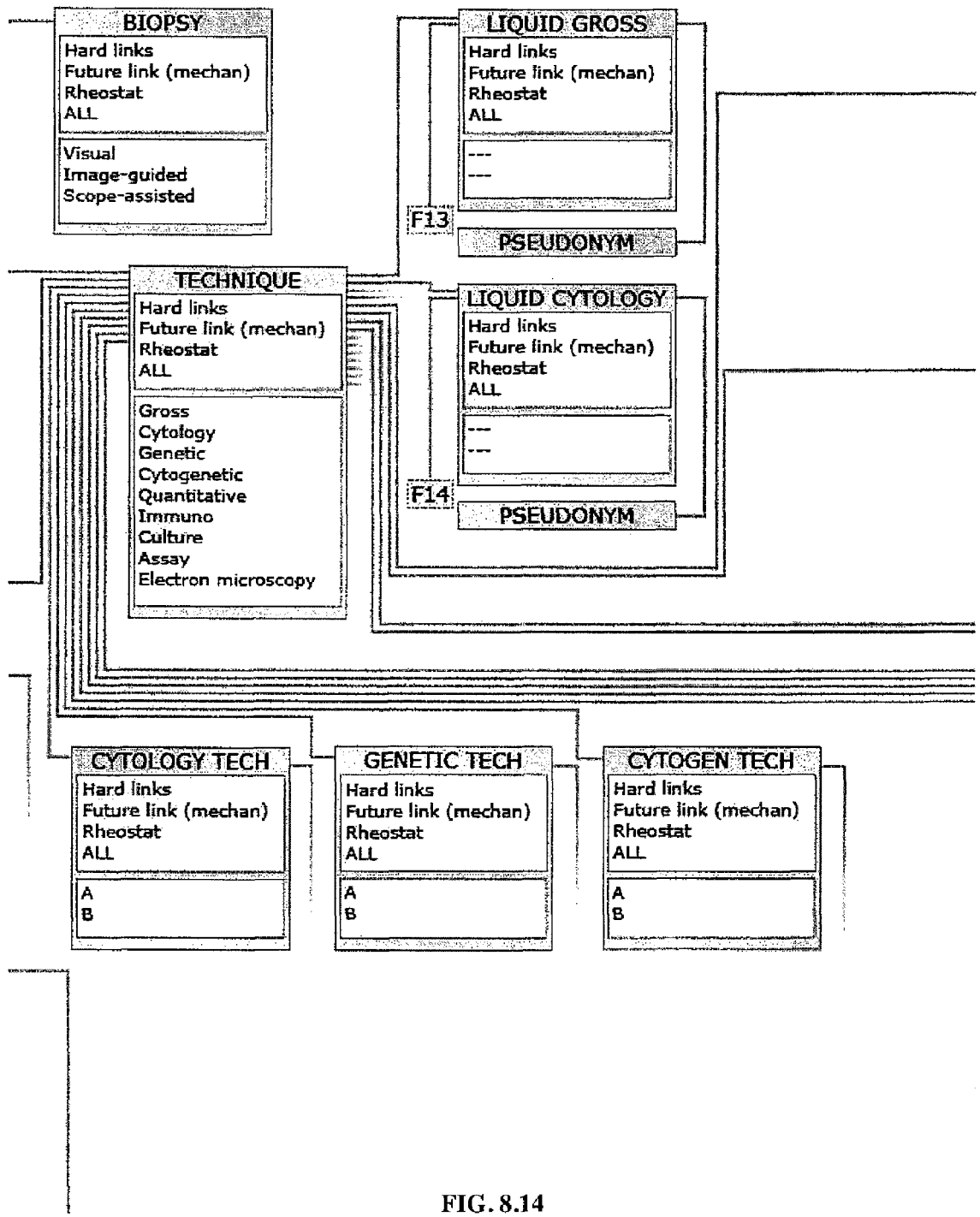
FIG. 8.14

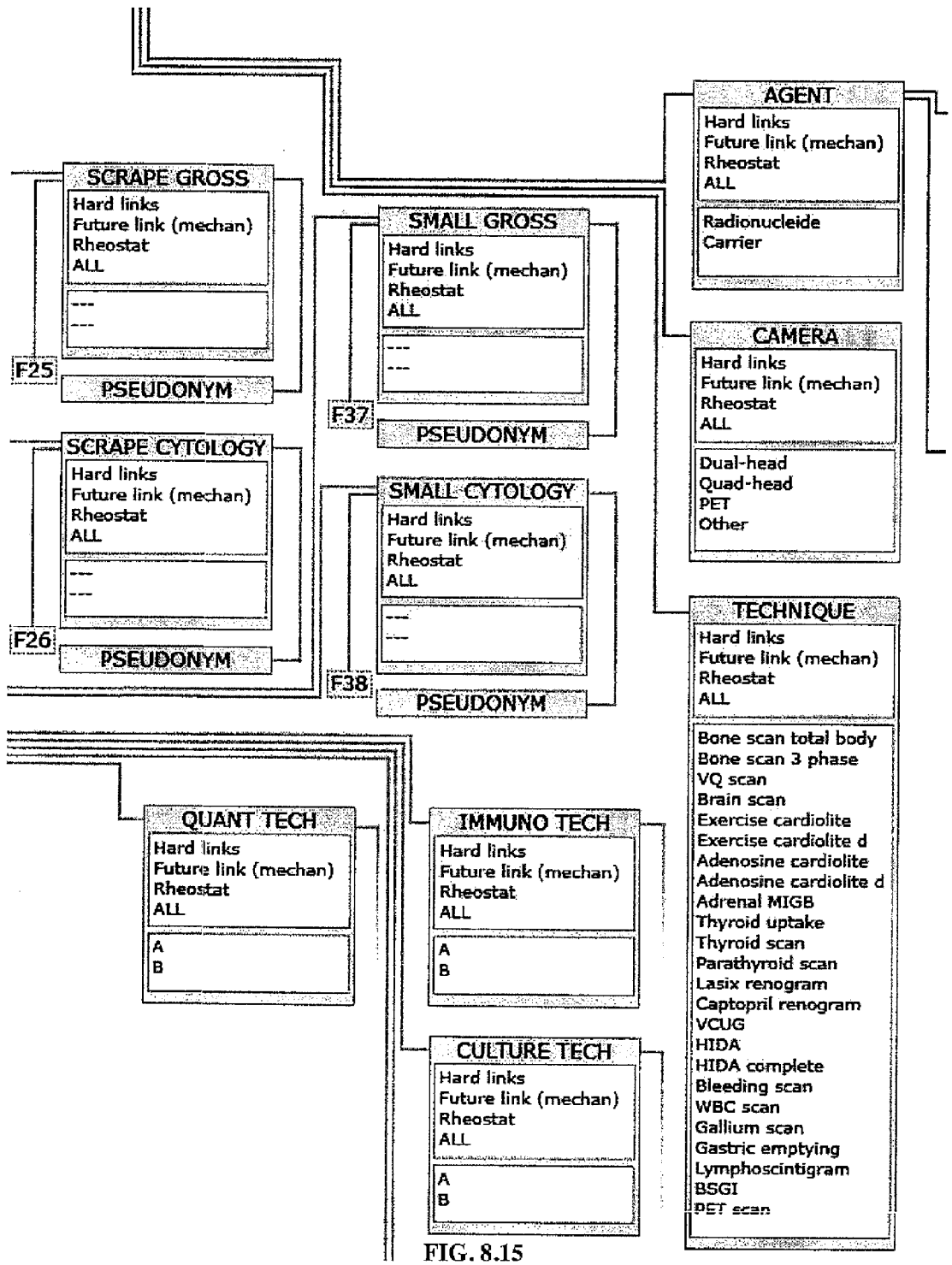
FIG. 8.15

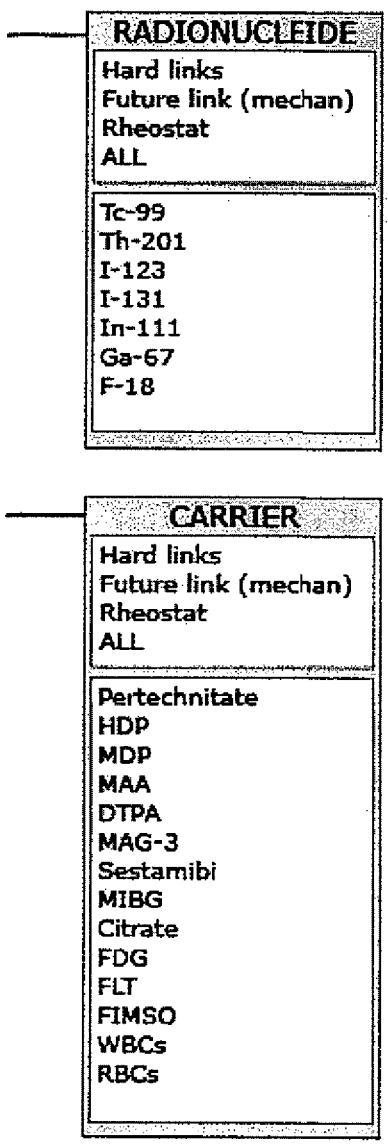
FIG. 8.16

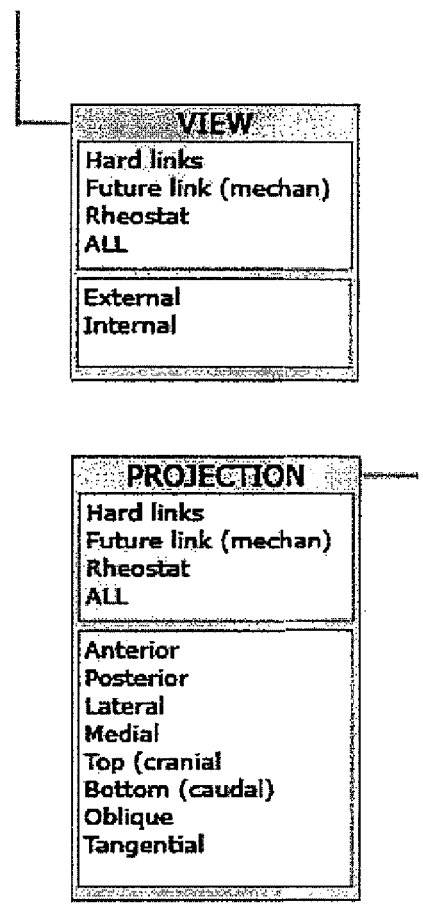
FIG. 8.17

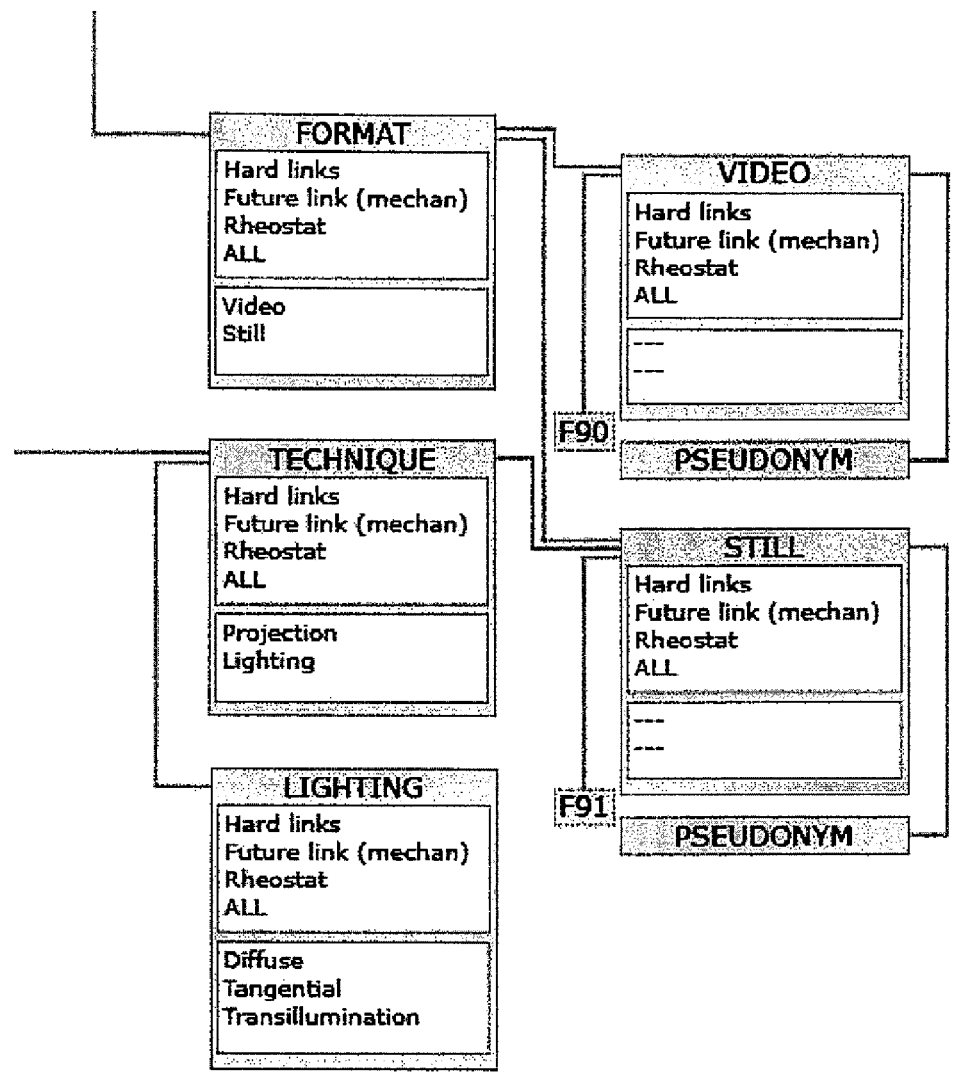
FIG. 8.18

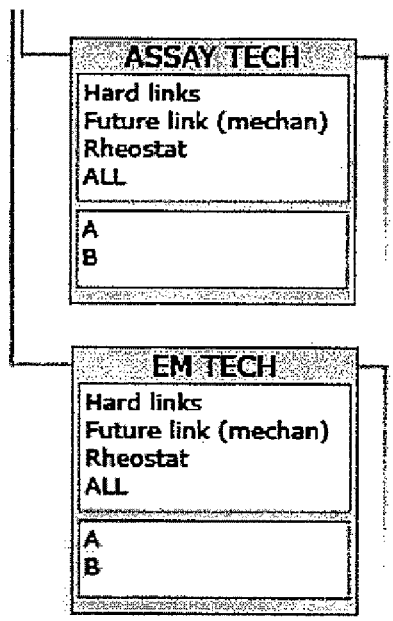
FIG. 8.19

410
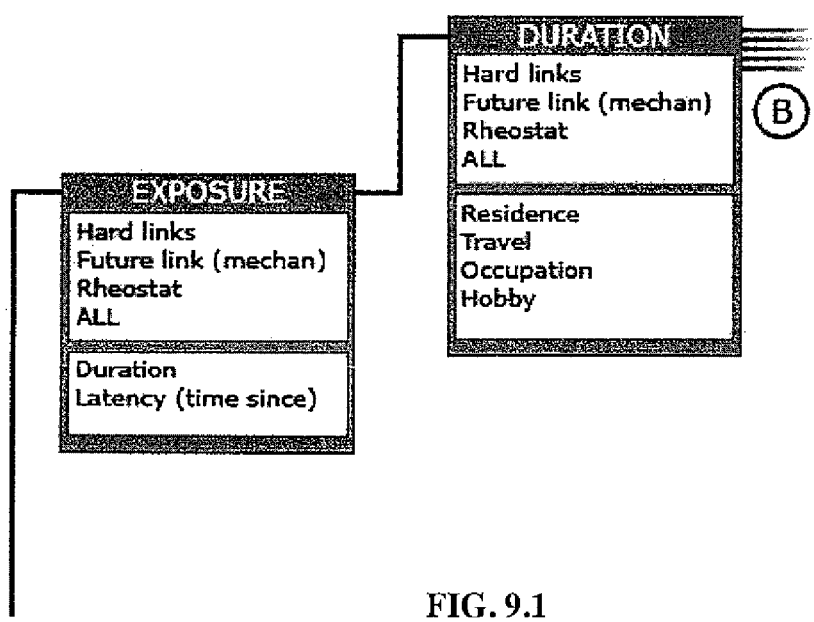
FIG. 9.1

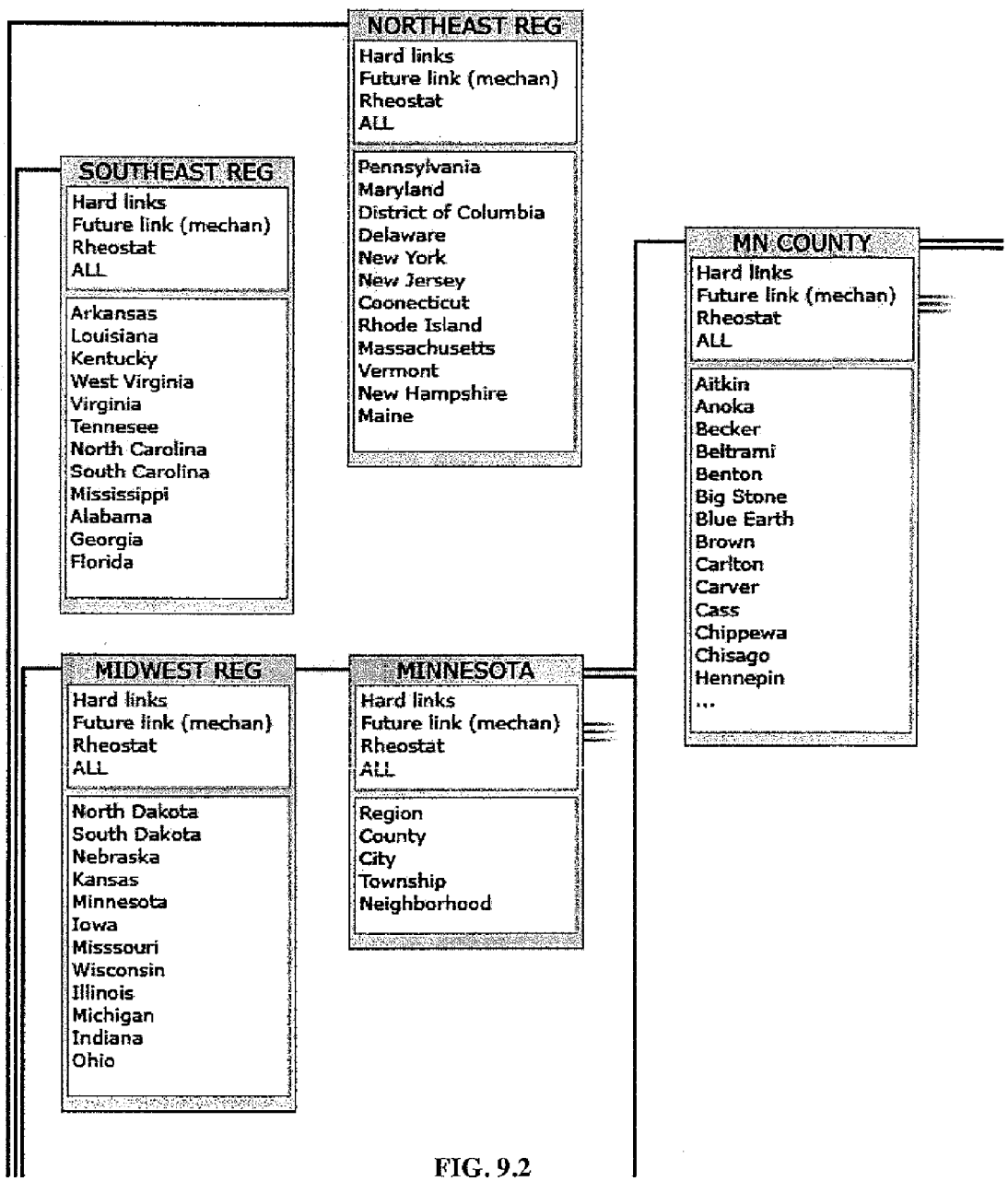
FIG. 9.2

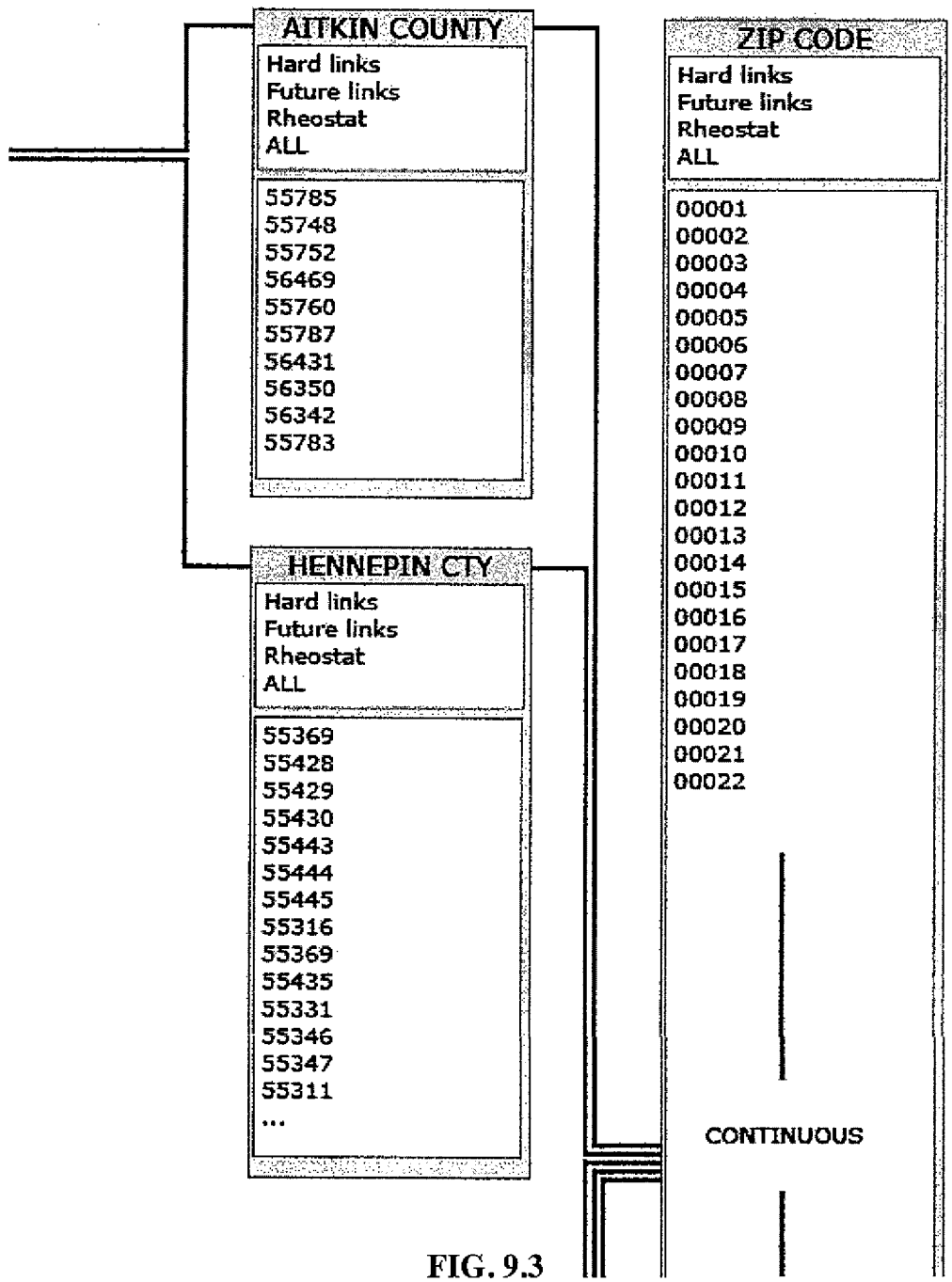
FIG. 9.3

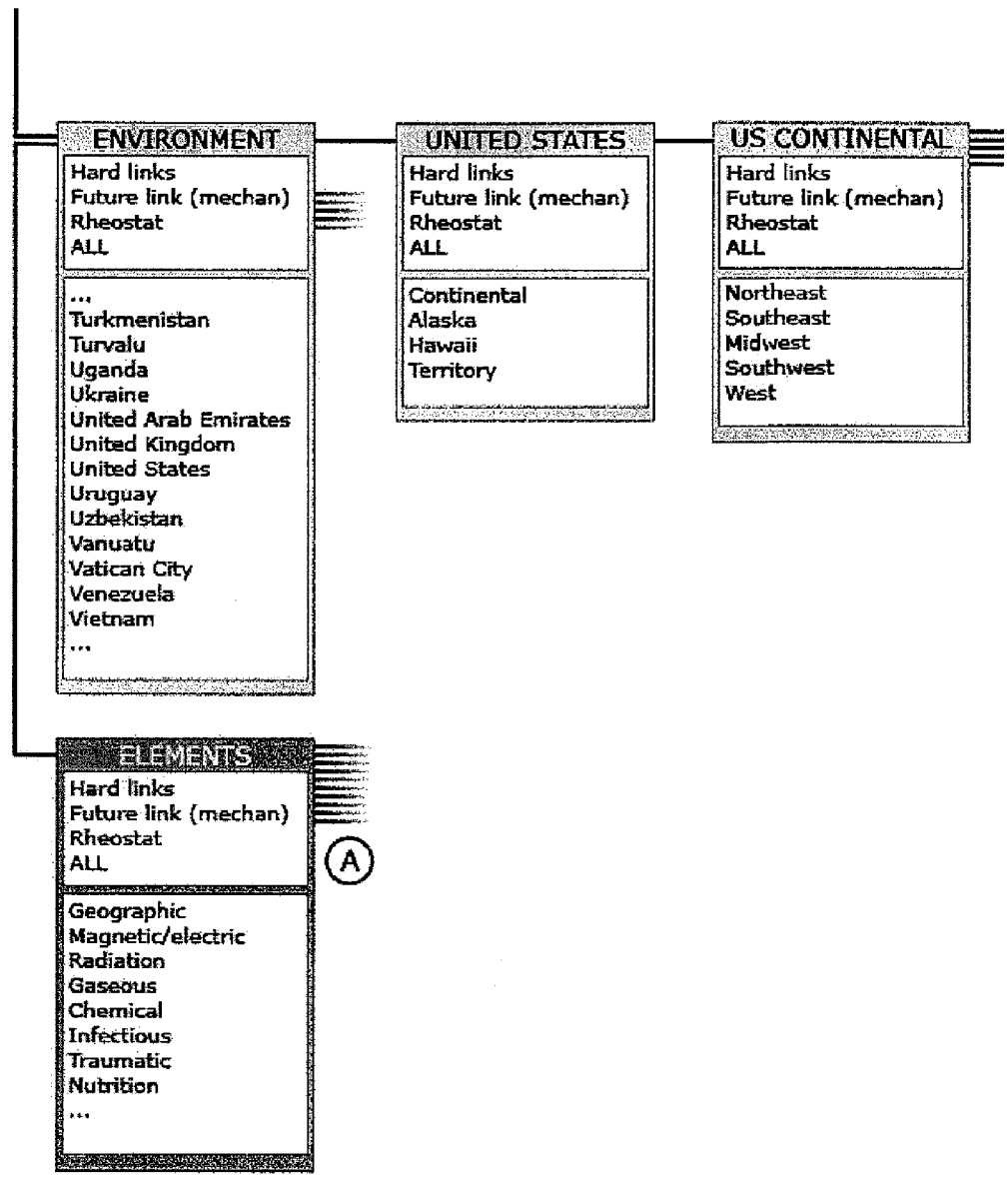
FIG. 9.4

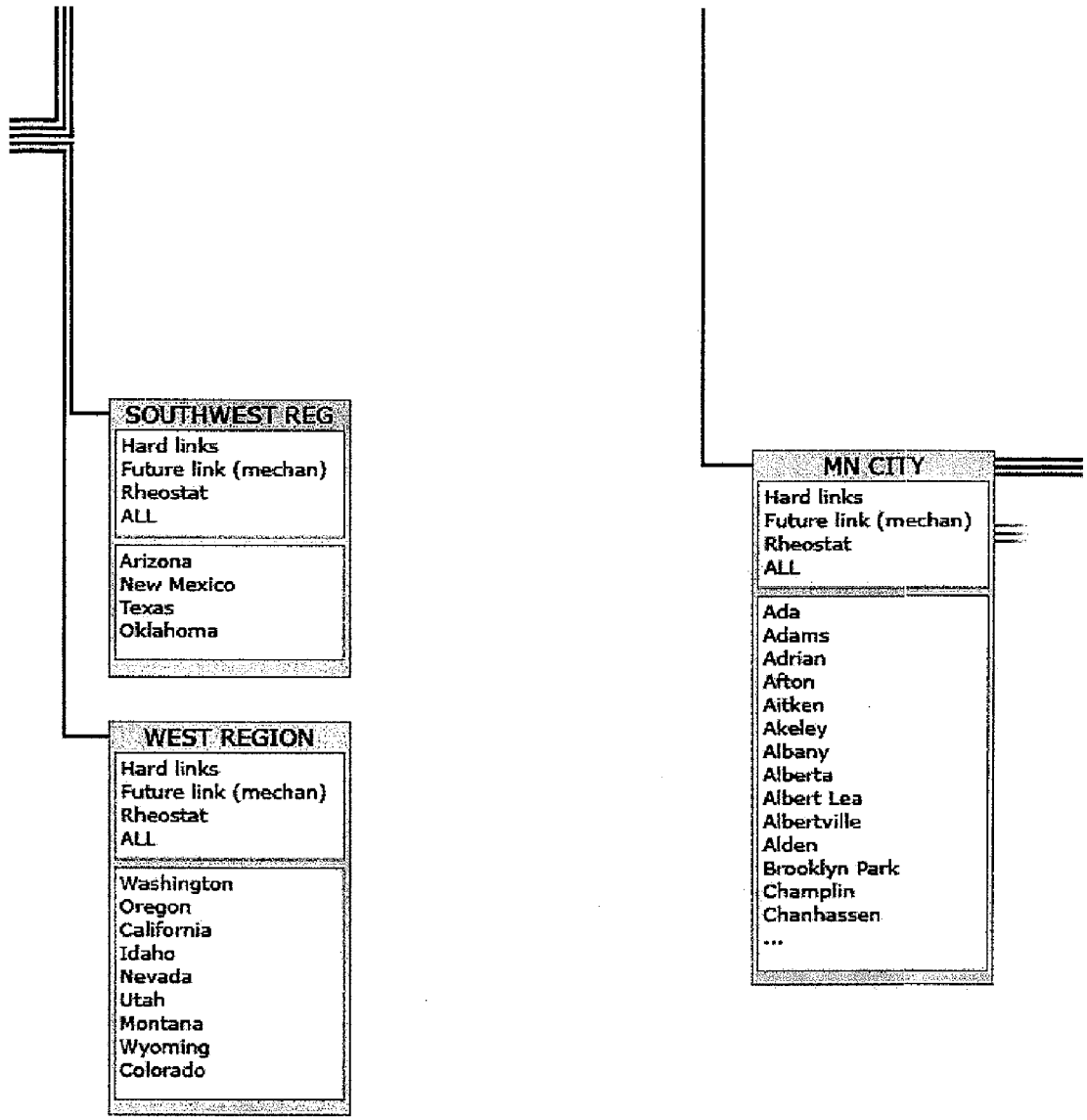
FIG. 9.5

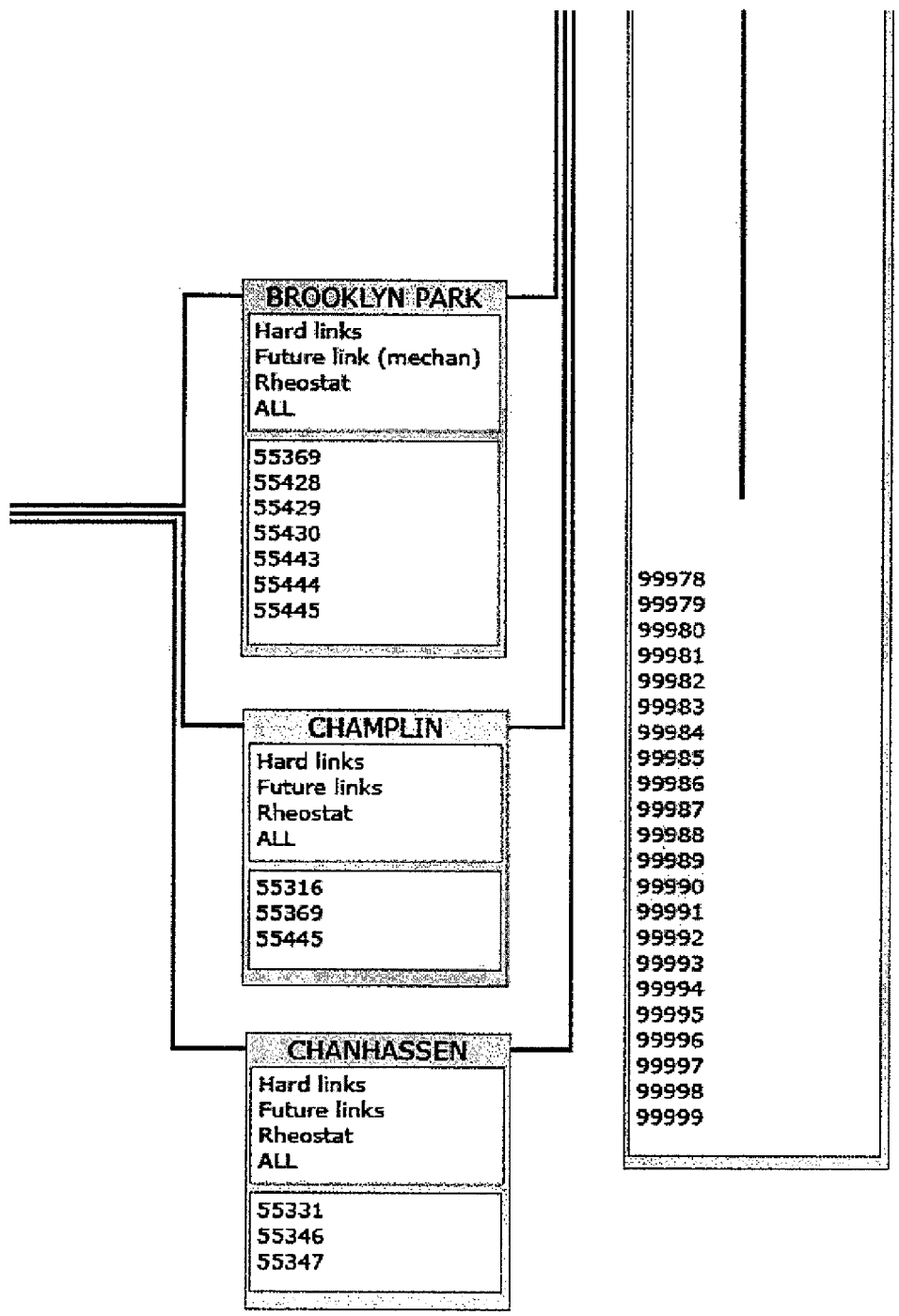
FIG. 9.6

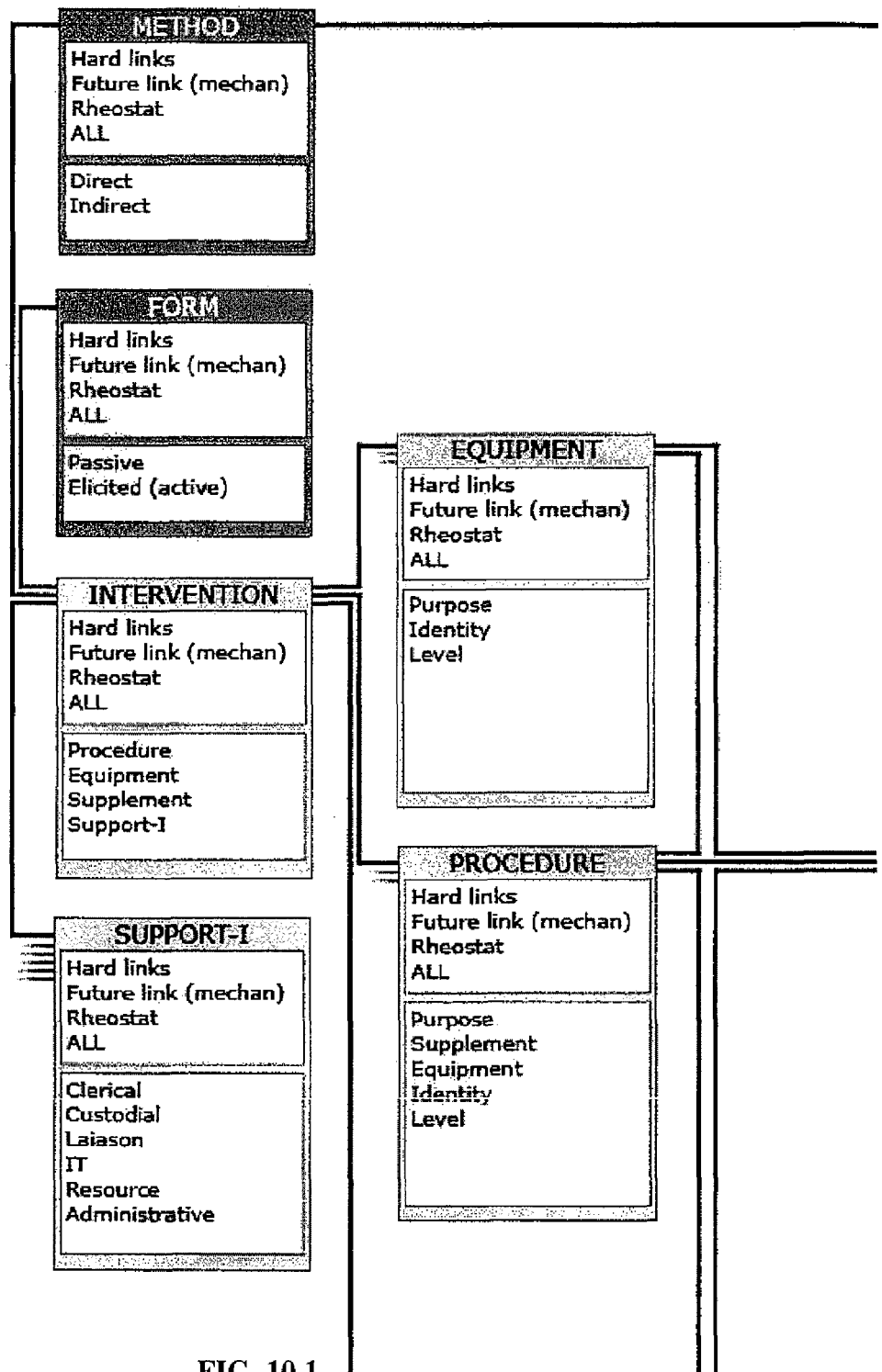
FIG. 10.1

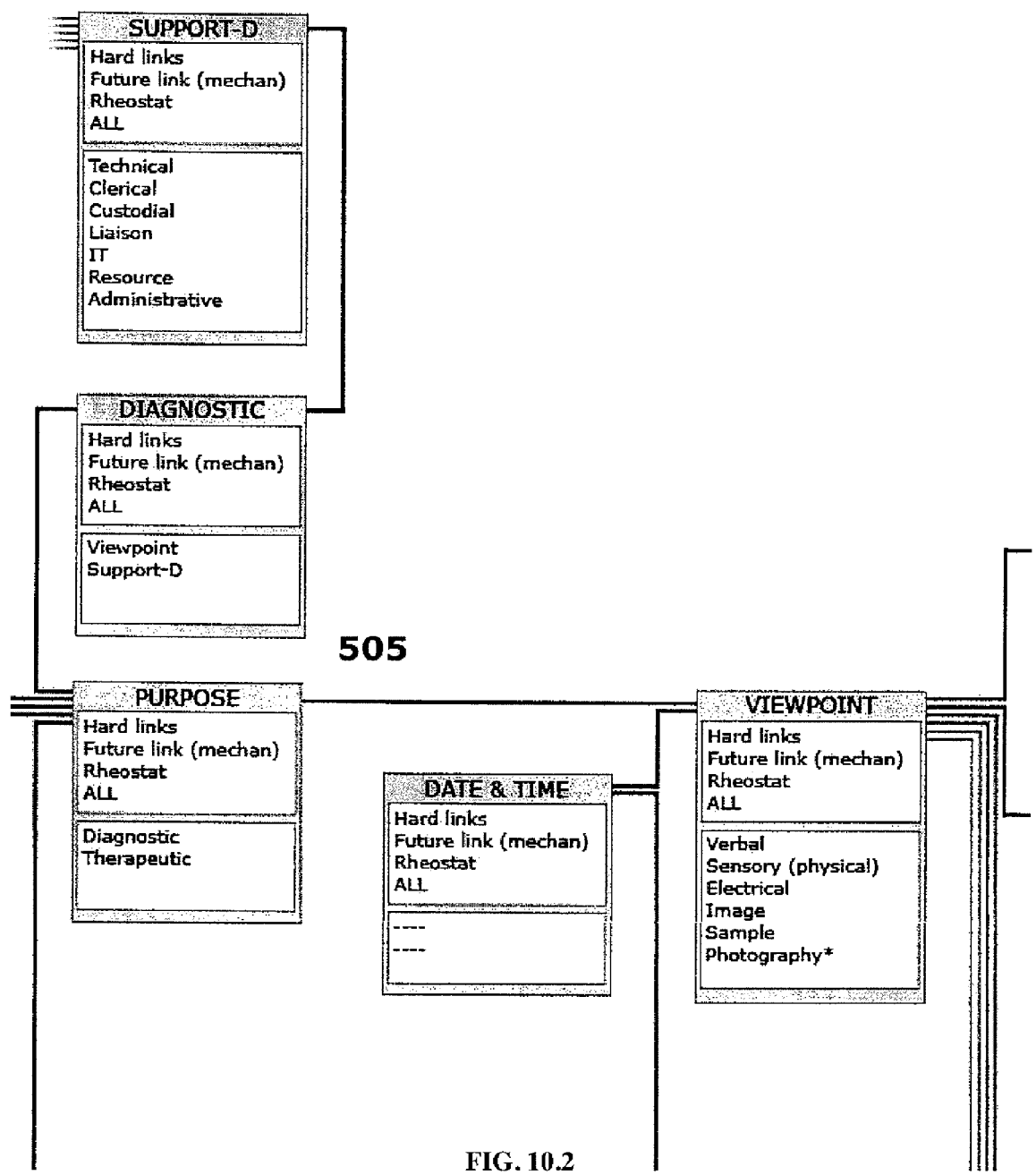
FIG. 10.2

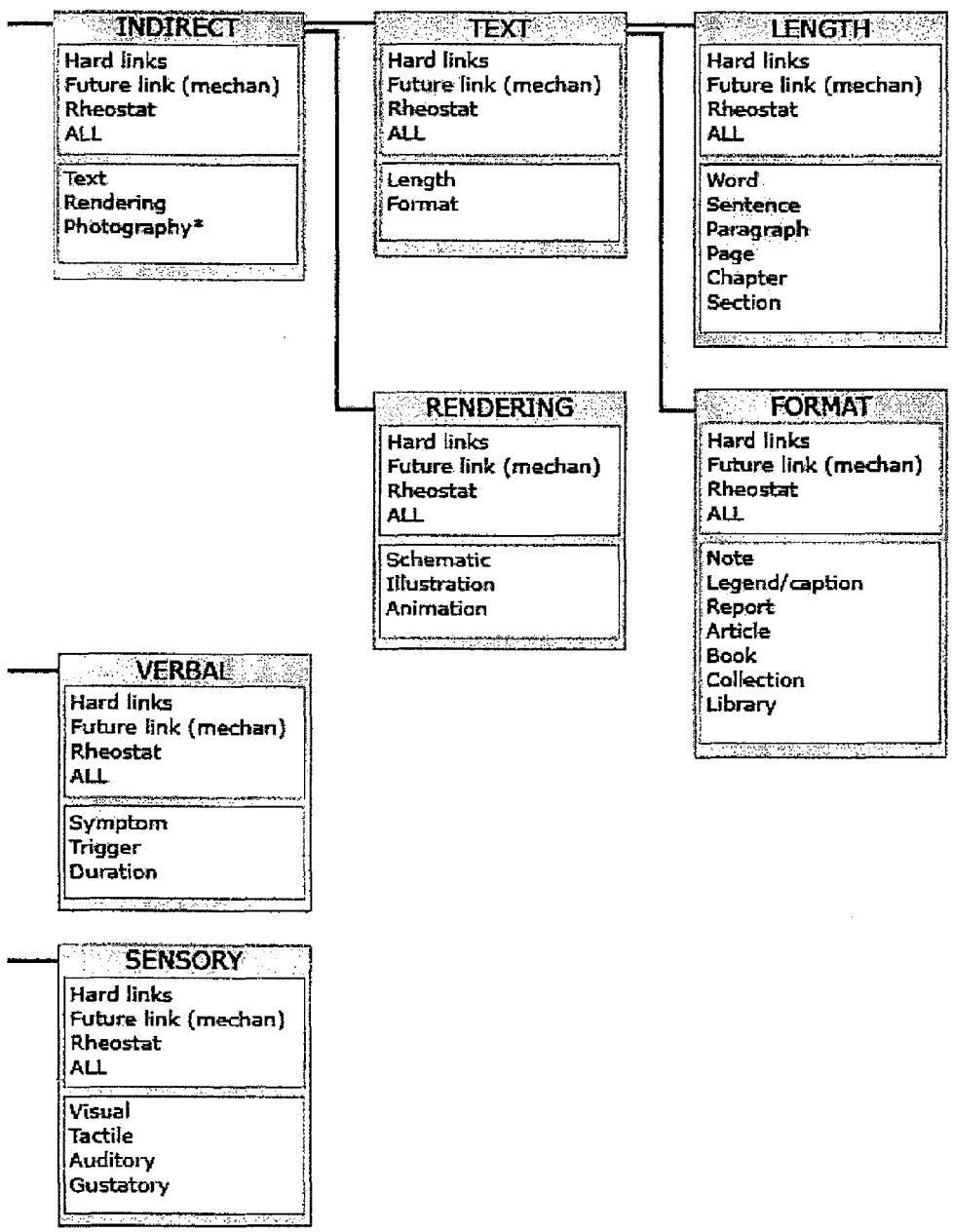
FIG. 10.3

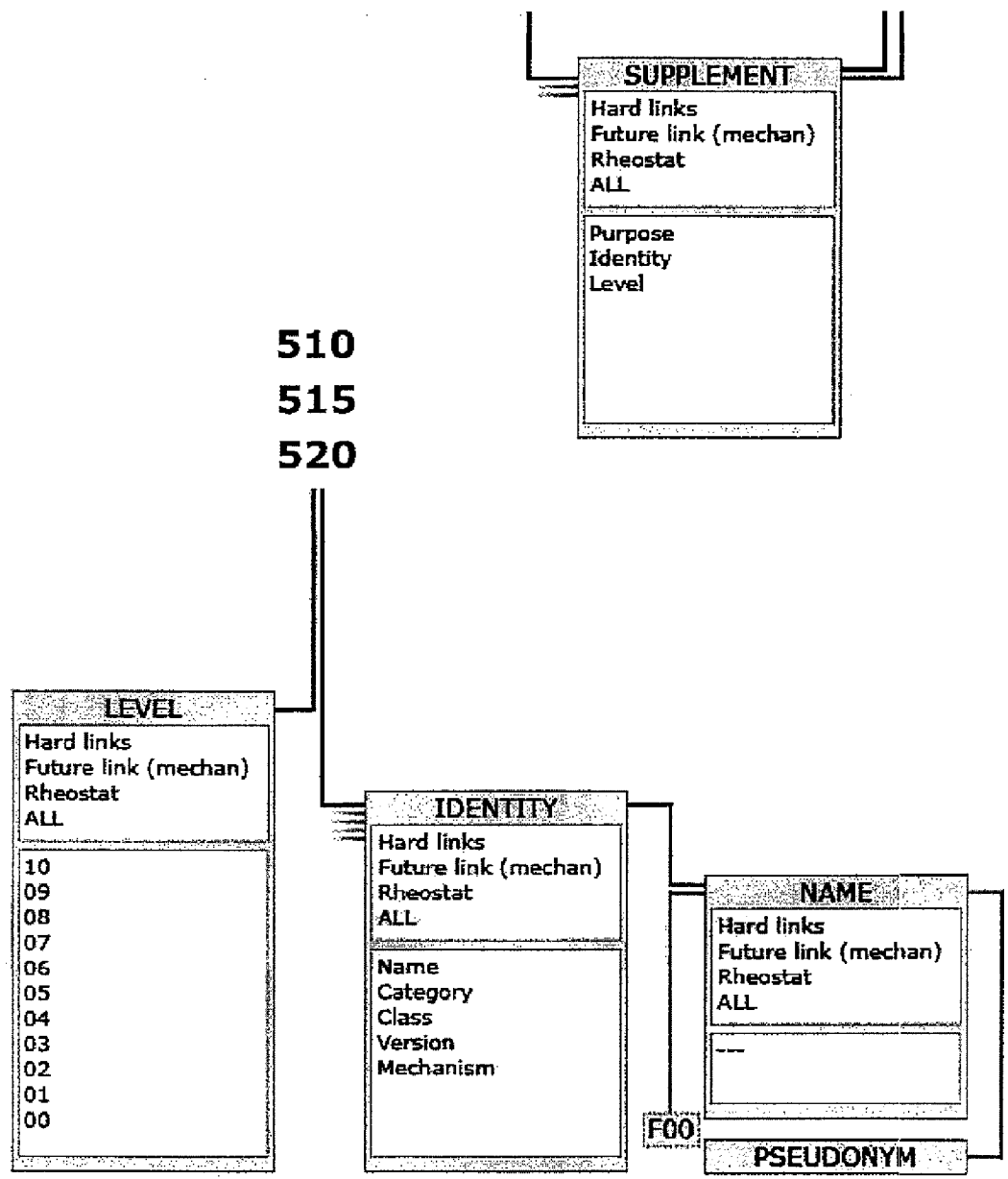
FIG. 10.4

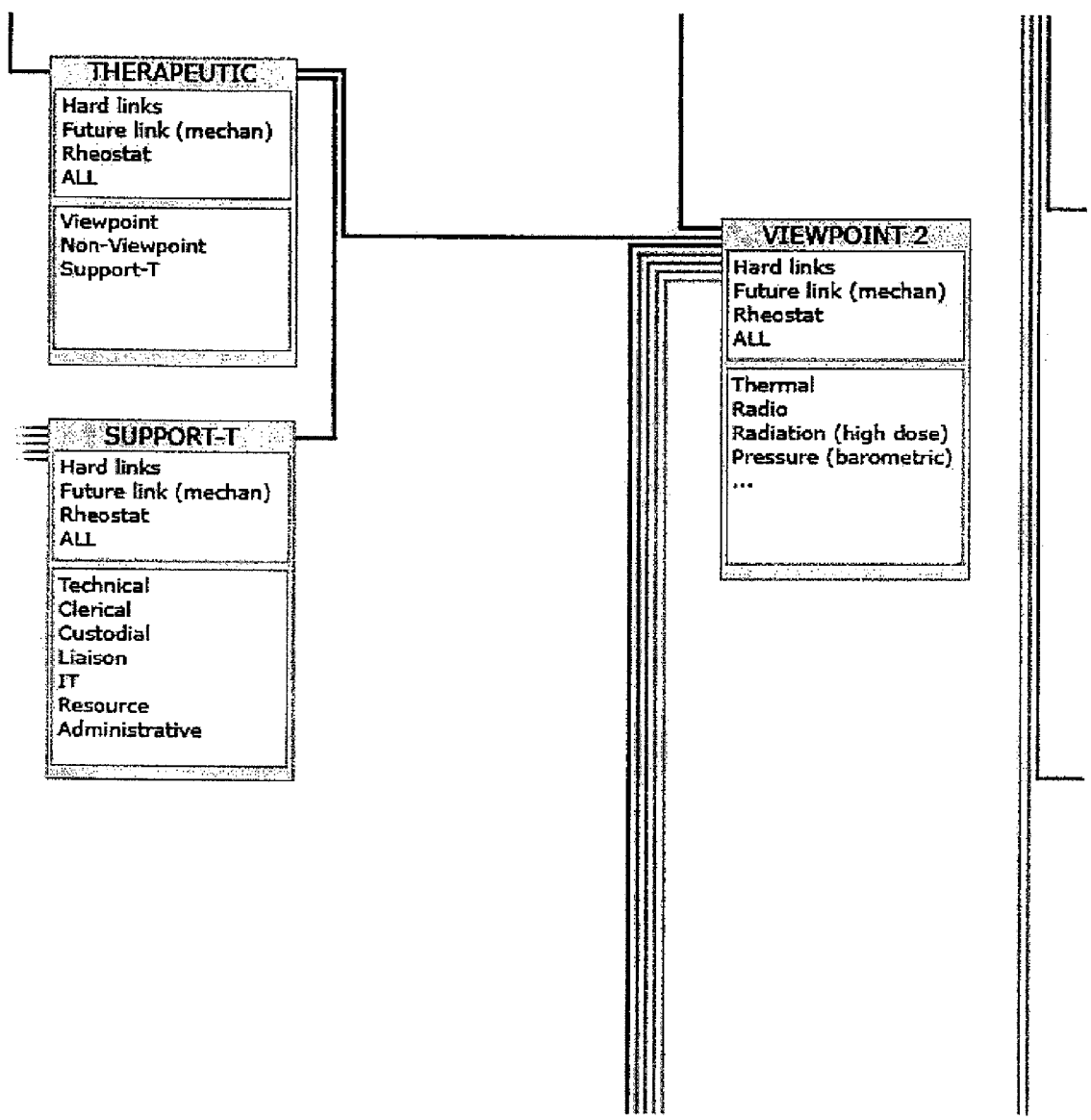
FIG. 10.5

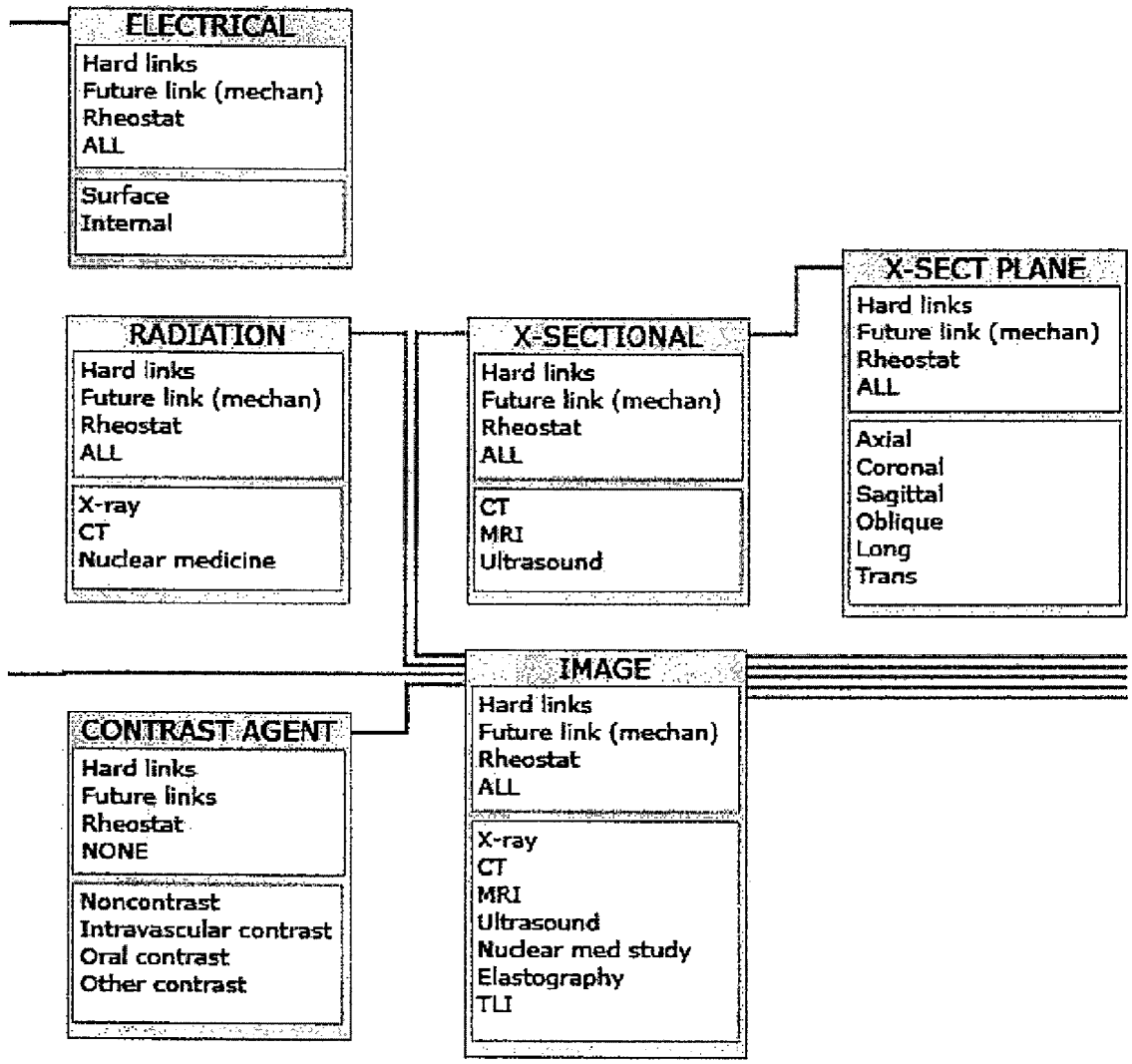
FIG. 10.6

METHOD AND SYSTEM FOR CREATING AN INDUSTRY-SPECIFIC COMPUTER DICTIONARY AND METADATA APPARATUS FOR COMPUTER MANAGEMENT APPLICATIONS USING A MULTI-LEVEL DATABASE OF TERMS AND DEFINITIONS

CROSS-REFERENCE TO RELATED APPLICATION

This application claims priority to U.S. Provisional Patent Application No. 61/440,467, filed Feb. 8, 2011, the contents of which are incorporated by reference herein.

BACKGROUND OF THE INVENTION

The present invention relates to a metadata system for data files used in medical imaging (DICOM3) that labels imaging files with data classified into five categories: identifying, patient, acquisition, relationship and image. The individual fields in the DICOM3 header are populated with data from the imaging devices, but there is no standard nomenclature for textual fields and the treatment of non-mechanical data in the header is extremely limited.

The deficiencies of the DICOM3 metadata restrict the ability of medical management systems (e.g. Picture Archiving and Communication Systems—PACS), to manipulate and display files, and collections of files, for different users and doesn't address the secondary meaningful use for the files or their intellectual content. Connectivity between management and information systems is also hampered by the lack of truly standard format and uniform nomenclature.

The invention is a stand-alone metadata apparatus that supports the DICOM3 format and not only provides the missing nomenclature, but expands the labeling system to include the entire range of potential intellectual content within a given field. The stand-alone nature of the apparatus also offers unlimited secondary meaningful use as it can be applied to related elements such as objects, people and locations within the field to create smarter, integrated management products and systems.

SUMMARY OF THE INVENTION

The invention 1000 consists of a metadata apparatus using a unique database of coded terms to describe a complex item in precise detail. For descriptive purposes, the apparatus is divided into three (3) areas—Core sections, Product Interface and Product Category.

In one embodiment, there are six Core Sections arranged in layers. From bottom-to-top, in an embodiment including six Core Sections, the sections are Form, Function, Examination, Condition, Intervention and Application. However, other embodiments in accordance with the present invention may have different numbers of Core Sections. For example, an embodiment may have five Core Sections. As used herein, a "section" is defined as the terms, tables and relationships connected to any one of the node tables in the Core (Form, Function, Examination, Condition, Intervention and Application). Each section contains a node table and many other tables listing coded terms. The node tables 100, 200, 300, 400, 500, and 600 are responsible for two primary tasks.

Summarizing the codes selected in the related section tables is the first task of each node table. The second task is to combine these codes with the code summary from the node table in the layer immediately beneath it (see FIG. 5). For example, Function 200, the node table from second deepest section, contains summary codes describing characteristics about the function of the item AND the summary codes in the Form node table 100, which describe characteristics about the form of the item. This process is repeated for each node table so that, if there are five node tables, the most superficial node table Intervention 500 contains summary codes for all tables in the intervention section, as well as summary codes for Condition 400, Examination 300, Function 200 and Form 100.

While the apparatus remains the same for all items, the specific terms, corresponding codes and some substructural relations in the database necessarily change with the item and related elements being described.

There are few if any circumstances where all of the coded terms in all five sections are selected at the same time; however, the default for each table is ALL. The decision on how to refine the selections is made at the highest levels, but is implemented largely in the Application area.

The Application area 600 is where code combinations come to life as meaningful tools for specific applications. Any element in the item's 'world' can be managed based on the definition of that element in the Application area. While the core sections, with their terms and relations represent the basic language, the Application area can be thought of as an electronic dictionary of definitions using this language. While some Product Categories make use of the entire core, most rely on the repeated use of specific definitions. These definitions are often grouped into discrete definition sets.

A Set 700 is a collection of definitions that share a common theme, or subject. Because of the core's unique organization and exhaustive terminology, themes can be anything, anybody or any place related to the item. Using the human body as the item, themes are selected to address every element in the field of health care from the patient to the devices, therapies and physical locations of service, to the people providing care, their training, and more. Examples of themes 705 for health care (i.e. item=human body) are included in FIG. 4.

While the Application area is both a conduit to the Core sections and an electronic dictionary of definitions, the Product Interface 800 is a transition area between the precise terminology below and the Product Category area above. This boundary layer is critical to the apparatus in several ways. In the subsequent discussion, the Core sections and Application areas, including Sets, will be referred to as the Core.

When used as metadata, the coded definitions are attached to individual computer files, and/or collections of files, where they describe not only the file type, but also the intellectual content of the file. Since every file can't have the entire Core to decode the definitions, the apparatus must provide a clean interface between the Core and the Product Category area where decoding takes place. The same holds true for data entry. Security features are also applied at the interface as the end products are disabled if separated from the Core. Finally, the ability to cleanly separate and reunite the Product Category area and the Core greatly increases the number of delivery options and streamlines the upgrade process.

The Product Category area 900 is where the metadata apparatus is divided into functional units based on the complex item and each of it's related elements. The strategies and techniques used to manage data can differ considerable from element to element. Dividing similar techniques into functional units not only optimizes performance, it facilitates both product development and the incorporation of new technologies. A description of each Product Category is provided with FIG. 4.

The Product area 950 is where the full utility of the metadata apparatus is realized. Developers are able to mix and match functional elements from one or more Product Categories to create finished Products. Products can be refined to address small management tasks related to a single department or a few lectures, or they can be configured to manage entire health care systems or medical schools. Finally, the management product can match the task—perfectly.

One embodiment of the present invention is a system for managing data including a database having a plurality of sections. These sections include a first section and a second section. The first section includes a first section table and a first node table, wherein the first section table includes a first set of codes, and the first node table is configured to summarize the first set of codes to create a first code summary. The second section includes a second section table and a second node table, wherein the second section table includes a second set of codes. The second node table is configured to summarize the second set of codes to create a second code summary, and to combine the second code summary with the first code summary. In one embodiment, only data included in the first code summary is included in both the first section and the second section.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 4 includes examples of these Sets and examples of specific Product Categories and Products. FIGS. 4.1-4.4 are magnified partial views of the chart, while FIG. 4 shows the whole chart formed by the partial views of FIGS. 4.1-4.4.

FIGS. 5.1-5.4 are magnified partial views of the chart, while FIG. 5 shows the whole chart formed by the partial views of FIGS. 5.1-5.4.

FIGS. 6.1-6.6 are magnified partial views of the chart, while FIG. 6 shows the whole chart formed by the partial views of FIGS. 6.1-6.6.

FIGS. 7.1-7.27 are magnified partial views of this chart, while FIG. 7 shows the whole chart formed by the partial views of FIGS. 7.1-7.27.

FIGS. 8.1-8.19 are magnified partial views of this chart, while FIG. 8 shows the whole chart formed by the partial views of FIGS. 8.1-8.19.

FIGS. 9.1-9.6 are magnified partial views of the chart, while FIG. 9 shows the whole chart formed by the partial views of FIGS. 9.1-9.6.

FIGS. 10.1-10.6 are magnified partial views of the chart, while FIG. 10 shows the whole chart formed by the partial views of FIGS. 10.1-10.6.

FIG. 11 illustrates the core architecture and basic organization of the terms in each section. The concept that collections of coded terms are organized by Product Category and that Products are created from these elements is also depicted.

DETAILED DESCRIPTION OF THE INVENTION

Figure 1:
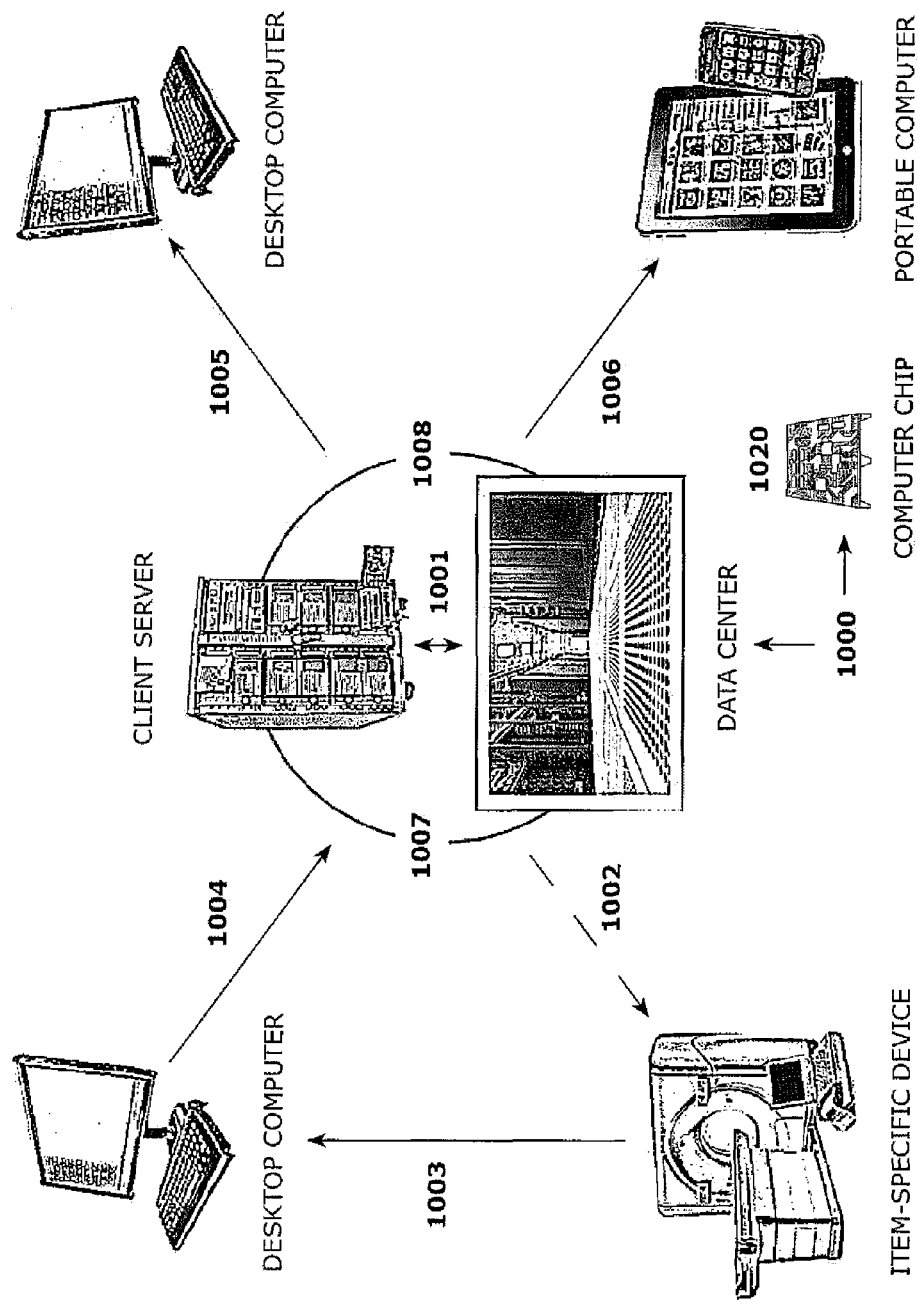
FIG. 1 is a diagram illustrating the physical location of the Apparatus. Depending on security and products constraints, the entire Apparatus may not reside on all of the hardware devices shown, all of the time.

FIG. 1 is a diagram showing physical locations of the apparatus. The apparatus is compatible with all operating systems and resides in total or in part on these computer systems. The apparatus is maintained in a data center. The entire apparatus can be exported to servers operated by end-users (clients). Defined components of the apparatus reside on item-specific devices and desktop computers to facilitate data entry and provide security. Remote access to the apparatus, and data managed by the apparatus, is provided to end users via both hard-wired and wireless networks including the internet.

The apparatus is created on desktop computers and servers in a secure environment and ported to a data center to provide anywhere access for clients 1000. Upgrades and new products are created in this secure environment and only sent to the data center for testing and implementation. The entire apparatus can be ported to client servers if needed, and the security features of the apparatus can be operated from either the data center or the client servers 1001. The data center can also serve as a backup for the client servers.

Data entering the apparatus can be divided into two classes—Client and Content. Client data consists of information and files that are restricted to the client organization and are entered and used by the organization. Content data includes information and files that are part of a content-laden product. The data entry process 1007 is described in FIG. 2.

Data from both classes communicate with the apparatus on desktop computers and servers with desktop computers. Digital data from information systems or verbal questioning, scanned documents and informative materials created on a computer are entered into products using the apparatus across both hard-wired and wireless networks 1004.

Subsets of the apparatus are created for item-specific devices 1002. Each subset is designed to work with a specific type of device so that the components of the apparatus subset match the data output of the device. Working with the device software, the subset applies the appropriate metadata to the output data. When the pre-labeled data is transferred to the desktop computer for management, this metadata is inherently recognized by the full apparatus 1003.

End-users (clients) access the apparatus, and data managed by products using the apparatus, across both hard-wired 1005 and wireless 1006 networks. The operating system employed by management products to accommodate desktop computers and portable computers may differ, but the operation of the apparatus remains the same. Portable computers include laptop computers, smart phones, computer tablets and any portable computing device that has memory and a display screen and uses software.

A security barrier prevents unauthorized access to the apparatus and data managed by products using the apparatus 1008. User names and passwords are employed, but the apparatus itself offers added protection by creating profiles for each user.

The amount of the profile that is activated is determined at the product level; however, the complete profile architecture is part of the Product Interface area and is available to all Product Categories. Profession including specialty, level of training and security clearance are all defined by the apparatus. Additional personal data such as preferences, contact information and biometry are included. The same profile is also used to prevent unauthorized data entry.

While the apparatus, or parts of it, resides in computer memory and is processed by 'general purpose' computer chips, for some applications performance and security may be enhanced by creating a computer chip specifically for the apparatus 1020. The chip-memory combination with the apparatus could then be added to the devices already described in FIG. 1.

Figure 2:
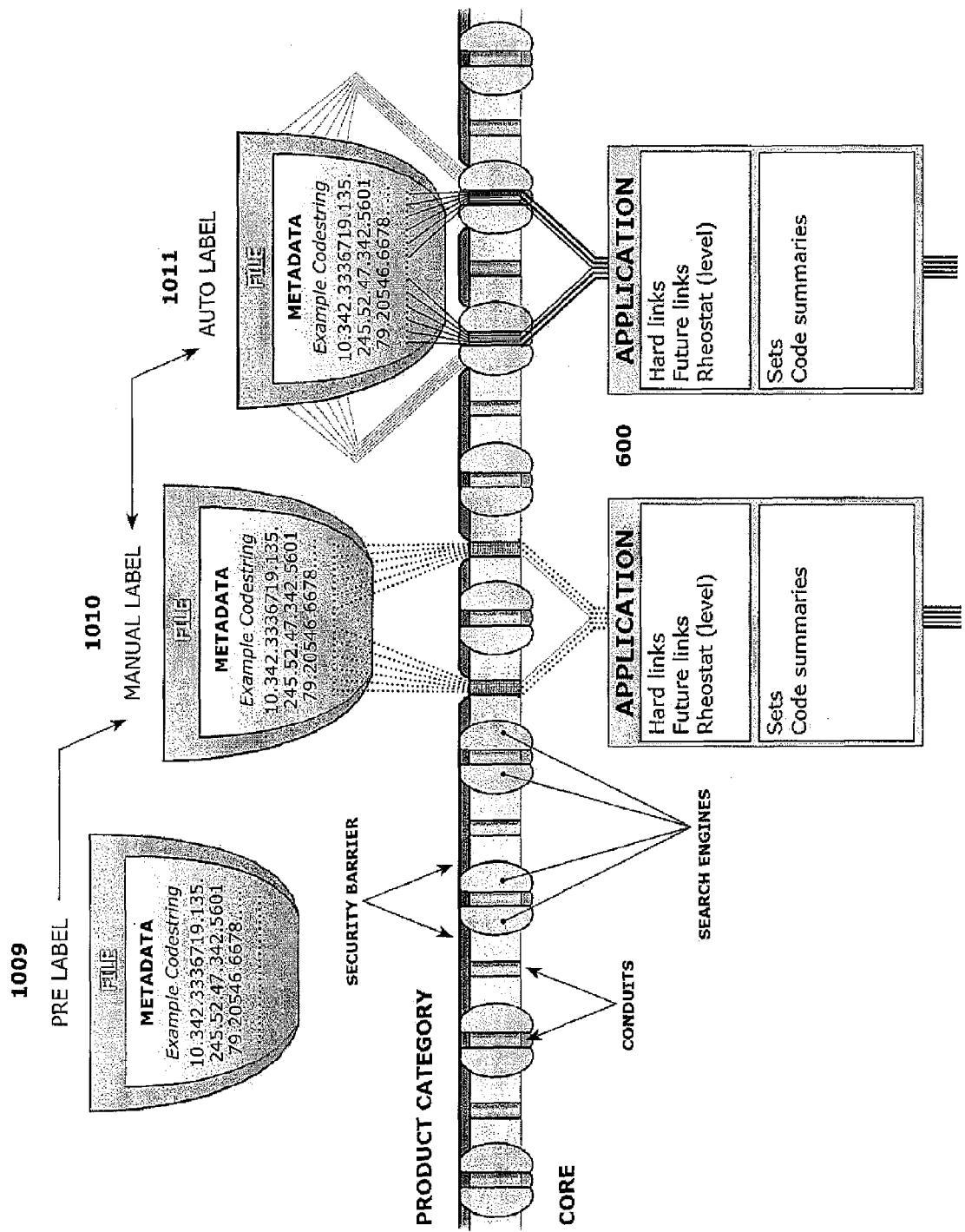
FIG. 2 is a diagram depicting the three basic methods of labeling files with coded metadata. The relationship between the Product Category, Product Interface and Application section of the Core determines which methods are used for any given Product.

FIG. 2 is a diagram representing Product Interface and Data Entry (1007). It is a schematic representing the Product Interface as a dynamic barrier controlled by the apparatus. The security barrier prevents unauthorized access to the Core. Once access is granted, via user name and password or biometrics, files can be labeled with the metadata codes. The file types and labeling strategies vary between the different Product Categories, but these strategies rely on three basic methods. Data files from 'enabled' devices are Pre-labeled, Enabled means that the device software is configured to apply appropriate codes as the data is generated. For devices generating simple data (e.g. counting or measuring), Pre-labels may be complete, but for devices generating complex data, additional labeling is often needed. Additional labels can be applied manually and/or automatically. For files that require the interpretation of complex data, manual labeling is used most often. Complex files, and simple files that don't originate from an enabled device, that do not require interpretation can be labeled automatically. Automatic labeling exploits search engine technologies to apply the appropriate metadata. Text and illustrations are examples of files that can be labeled automatically. The approach to data entry is dictated largely by the end product, as different products need more or less metadata to operate properly.

Accurate data entry is critical to the operation of every computer system and the apparatus is no different. What is different is how the apparatus addresses data entry. In short, data entry is viewed as a complex item that requires precise managerial control.

The terms in the Viewpoint section (see FIG. 8) define the types of data to be entered, and these are related to parameters that define how much human interaction the data entry requires—before, during and after it enters the apparatus. Quality control features are also a part of the Product Interface and allow the apparatus to both police itself and modify the data entry processes as needed.

Some of the principle human issues addressed in the data entry process are: who is authorized to enter data, what data are they allowed to enter, does the data need to be double-checked or validated by a second party, how is the second party enlisted in the process, how frequently should different data types be checked for accuracy (QA) and how are discrepancies addressed. In addition to manual metadata application, the apparatus also supports pre-labeling and auto-labeling.

Pre-labeling 1009 is defined as the application of metadata to data files generated by an item-specific device by that device. Pre-labeling can only occur if the device has been enabled with a subset of the apparatus that matches the output data of the device.

Figure 5:
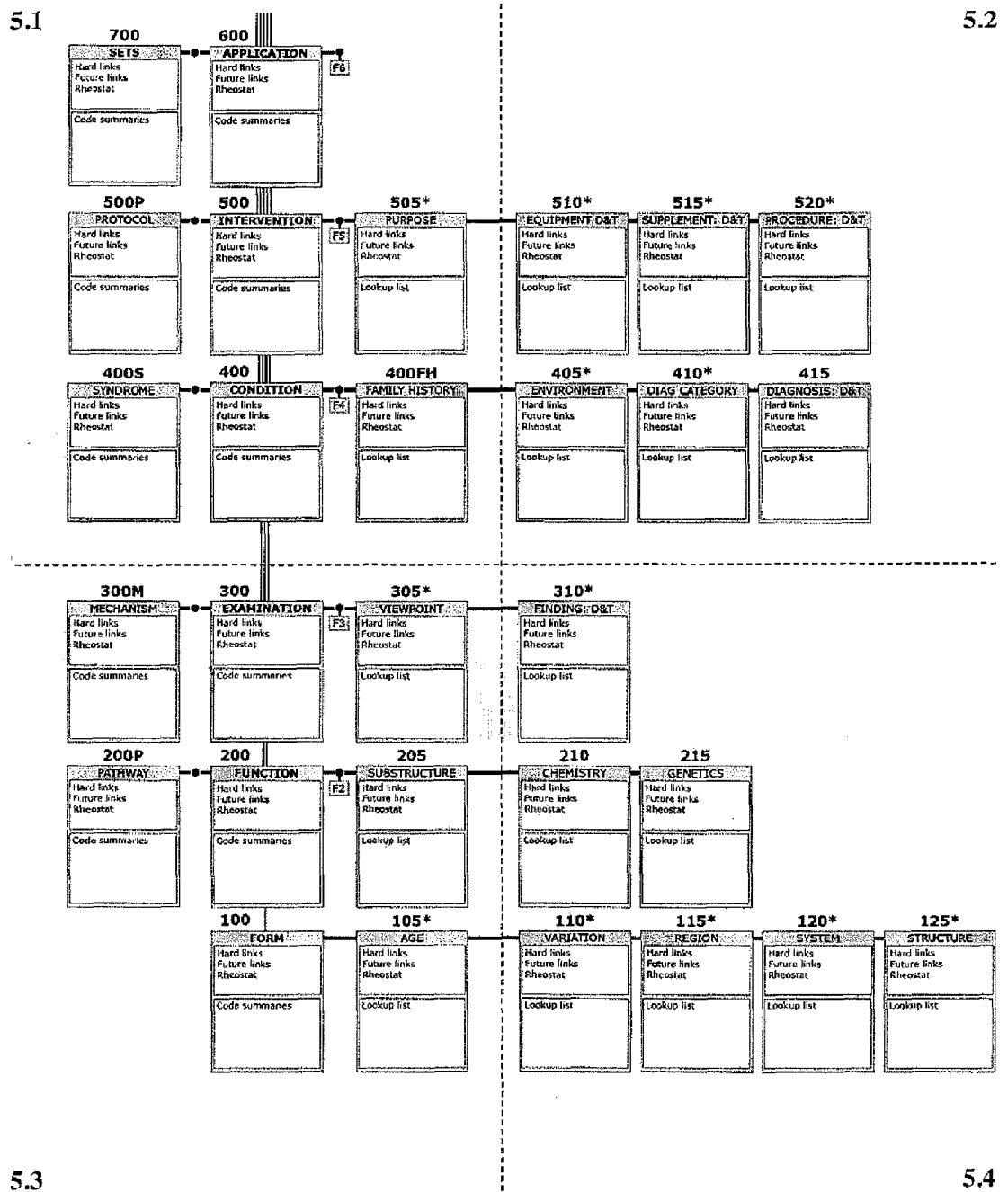
FIG. 5 is a chart depicting the Core's organizational architecture. The Apparatus derives its flexibility from the Core's unique organizational architecture. Coded terms, layered in six complementary sections employing both associative and relational techniques, provide the basis for the comprehensive code strings that can define any element in health care.
Figure 6:
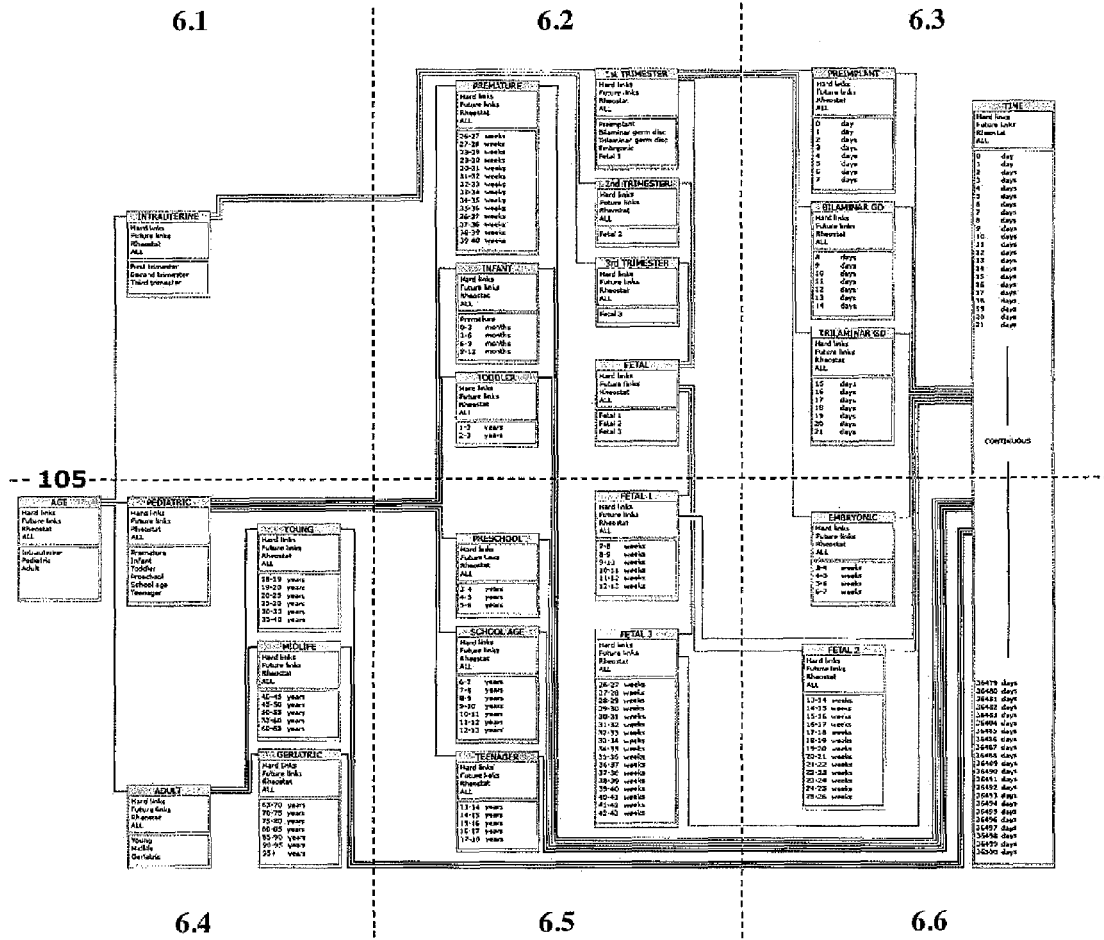
FIG. 6 is a chart showing a detailed view of the terms, tables and relationships for the Age parameter in the Core's Form section. Notice that choices for Age can vary from a single day to decades, and all of the standard age ranges used in health care are represented.
Figure 8:
FIG. 8 is a chart showing a detailed view of the terms, tables and relationships for the Finding parameter in the Core's Examination section. Findings for the six major viewpoints are represented as are methods to not only insure consistent terminology, but provide a smaller, more focused collection of descriptive terms for each element in any given viewpoint.

For example, a subset for a CT scanner includes: all of the node tables, the entire Form section except Intrauterine Age, the Image portion of Viewpoint in the Examination section, the Condition section, the Application area and the Radiographic study Set from the Work Sets, which already contains definitions for each CT study using the terms in these parts of the Core (see FIGS. 5, 6 & 8). The device manufacturer, model, software, and other mechanical data of the device are already part of the DICOM3 header.

The pre-labeling process applies metadata that is immediately useful for managing data files; however, these same files can undergo subsequent manual and/or automatic labeling. The subsequent labeling may be derived from the intellectual content of the files, which requires human interpretation and manual labeling, or come from information from another source that automatically applies metadata related to higher core sections like Condition or Intervention (e.g. other diagnoses, current medications, therapies, recent procedures, etc.).

Item-specific software programs, like item-devices, can also be enabled with subsets of the apparatus. Examples in health care include Hospital Information Systems (HIS), Radiology Information Systems (RIS), Electronic Health Record (EHR).

Auto-labeling 1011 is defined as a metadata labeling technique that does not require direct human intervention, such as incorporating search engine technologies to scan data files and apply the appropriate metadata to the same file, or other files. Currently, the source files for auto-labeling are restricted to those with text (including audio voice files converted to text with voice-recognition techniques). Despite this limitation, auto-labeling is a powerful tool for both data entry and quality control.

Text files comprise a large percentage of the research, education and management data in health care. By defining these files by type and applying metadata describing the content of the file, this enormous resource can be reshaped and presented in any number of different ways to assist those that rely on this information to provide care. Tables related to Viewpoint in the Examination section of the core define text by length and format, so if desired, metadata can be applied to each individual sentence.

Even though the sources files for auto-labeling are limited to text, the target files for the metadata can be any file type. Like all of the time-sensitive terms in the core, date and time stamps are applied to notes and reports so they too can be used as source files to auto-label the events or files on which they were based. This technique can be used to add intellectual content to a pre-labelled file by running the report for the file through an auto-labeling session and applying the metadata to the file. Depending on the product, applying text metadata to files other than the source file can have significant benefits.

For example, an operative report for a appendectomy describes the procedure and the date it was performed. It also mentions that the patient had a tumor on her right ovary so it was removed at the time of surgery. In the EHR product category, the metadata defining the removal of the appendix and the right ovary would automatically be attached to every imaging study of the abdomen and pelvis from the date of the procedure forward—without any human intervention.

For many products, at least some of the metadata application is done manually 1010. This process is controlled by the product and data entry requirements, but at least four features of the apparatus assist in accurate data entry.

First, the entire process is almost entirely menu driven with preset, universal terms and a consistent organization. Secondly, all of the menus are 'limiting', in that the selection in one menu limits the available choices in the next menu. Thirdly, the number of menus made available to the individual performing data entry is reduced by their personnel profile. The profile directs the apparatus to only those perspectives and data that match the profile. Instead of one or two perspectives for an entire product, the apparatus provides an unlimited number of data entry configurations. Full administrative access to the apparatus and all the data is reserved for very few IT personnel. A fourth feature is that the initial data entry can be considered preliminary until it is reviewed by a second individual, or subjected to a follow up auto-label session.

Figure 3:
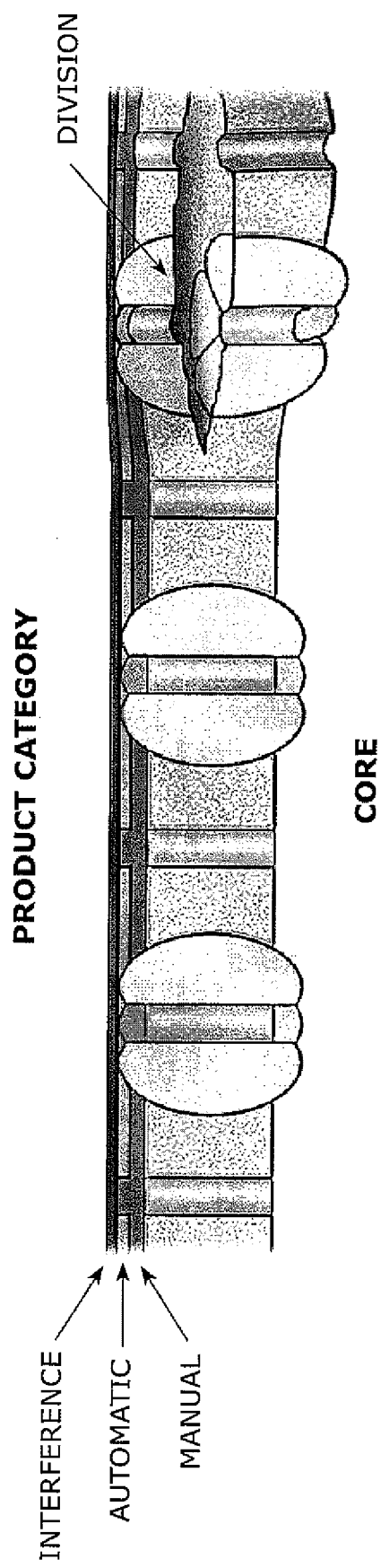
FIG. 3 depicts the elements of the Product Interface. While separating sensitive from non-sensitive information is built into all Product Categories, individual elements embedded in the Product Interface provide added security.

FIG. 3 is a diagram representing Product Interface and Security. It is a schematic of the Product Interface and layered security barrier. The Manual and Automatic layers are both designed to prevent unauthorized access. The Manual layer preferentially disables the manual processes while the Automatic layer disables the automatic processes. Each layer is independent from one another thereby allowing automatic metadata application while manual application is disabled, and vice versa. In contrast to access prevention, the Interference layer alters the code strings as they move between the Core and the file or product. Dividing the security barrier between the product and Core is another method to prevent unauthorized access.

The security features described thus far have been directed at protecting the integrity of the apparatus, and the data using the apparatus. Additional security features are found in both the Product Category and Product areas. These features are directed at both preserving the integrity of sensitive data and segregating sensitive data from non-sensitive information. Security features at both levels work together.

Figure 4:
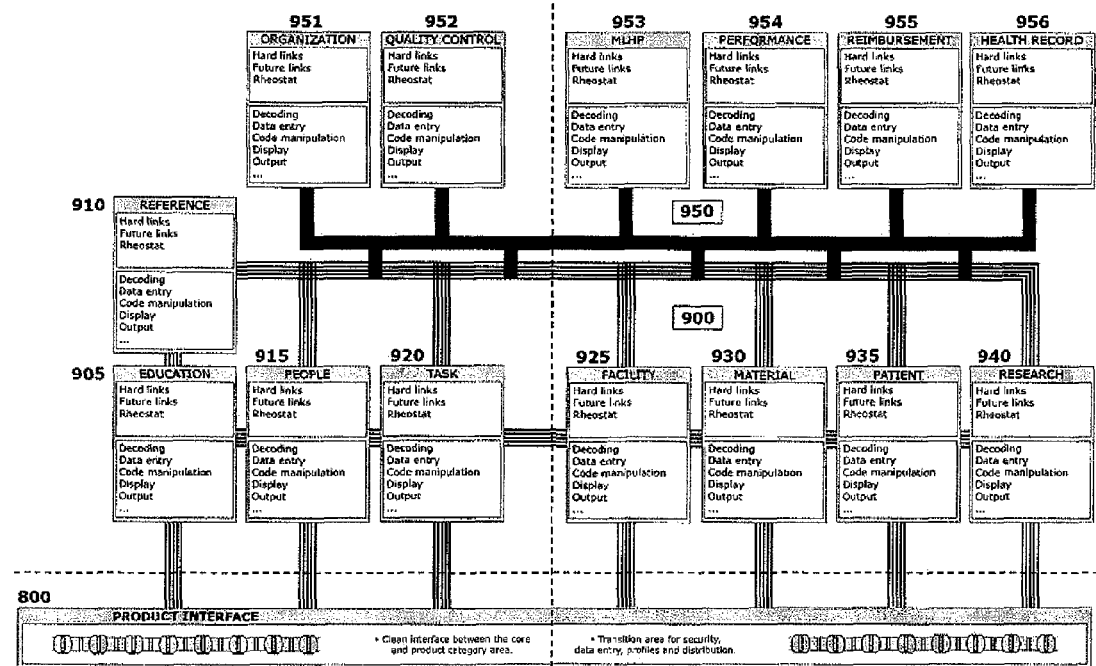
FIG. 4 is a chart showing Sets, Product Interface, Product Category and Product. The pre-defined collections of coded terms that are used frequently by Product categories are organized into defined Sets.
Figure 4:
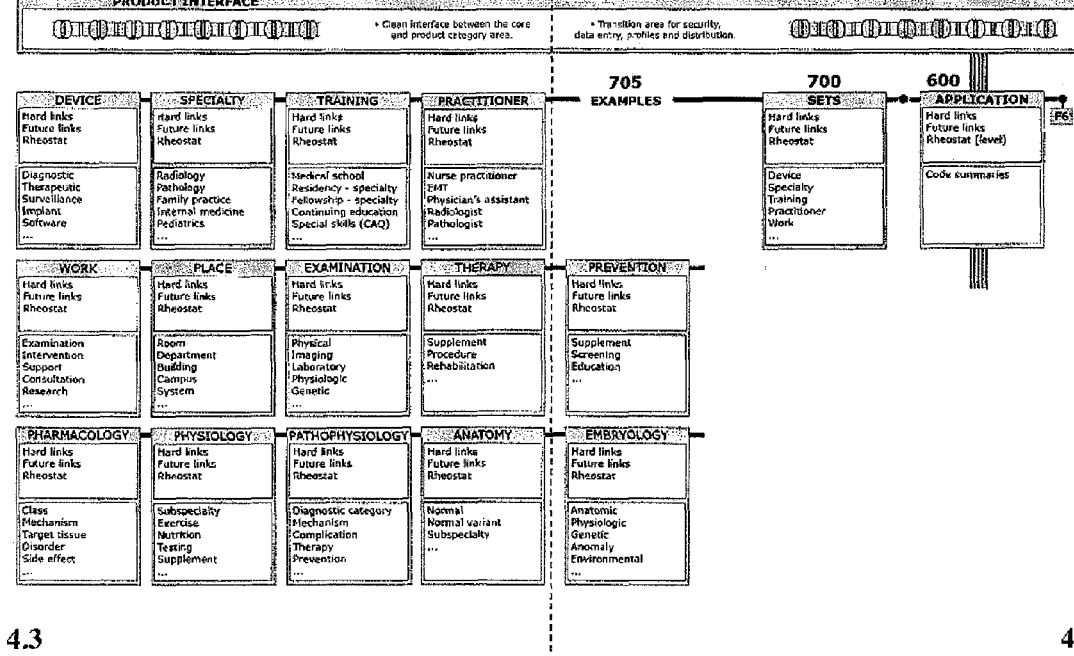

FIG. 4 is a chart representing Sets, Product Interface, Product Category and Product-Health Care. It is a schematic representation of upper level components. Sets are an important part of the Application area. A Set is collection of terms and relations that share a common theme. Sets facilitate product development and performance by condensing thousands of terms into a single code-string. The choice of themes depends on the demands of the Product Category. Some Sets focus on themes important to the practice of medicine, while others focus on those important to medical education and research. A few examples of each are shown above. The Product Category area 900 is where the specificity of the Core is married with other software techniques to manage data in specific categories. The Product Interface is the boundary between the terms and relations of the core, and the sensitive personal data managed by specific products. This interface also serves as a transition area for security, data entry (including search engine integration), personnel profiles and distribution techniques. Six representative Products are also shown 950.

The Application area 600 is both a conduit to the core sections that contain the apparatus language, and an electronic dictionary of definitions using the core language.

Definitions are divided into sets 700. Sets share a common theme and not only speed performance by streamlining often-used code strings, they are also the building blocks for more complex definitions at the Product Interface and Product Category levels.

One of the challenges in creating a universal electronic platform for health care has been the complex collection of elements that impact health care, which have evolved independently over the past 100 years. During this evolution, each of these elements created its own microcosm, complete with its own organization, disciplines and terminology. Sets break down these arbitrary barriers and define all of these elements in common terms.

The number of different Sets is virtually limitless. Developers have the ability to create new Sets to satisfy the requirements of a new product; however, they are not allowed to modify the Sets already created and any new Sets must become part of the apparatus. A few examples of Sets are provided 705.

For clarification, the list of terms in each Example table represents another table with multiple related tables. For instance, the Device table contains the term Diagnostic, which is a table related to other tables defining many different diagnostic devices—each with a detailed code-string from the core. In the Specialty table, Radiology is related to other tables defining all of the different sub-specialties in radiology. And so on.

The Product Interface 800 serves a number of important functions for the apparatus. While some of the security and data entry features were already described with FIGS. 2 & 3, the user profile deserves more attention.

Everyone who accesses the apparatus or products using the apparatus must have a user profile. The profile serves as security to prevent unauthorized access, but it also allows the apparatus to customize the user experience in ways never before possible.

A profile may contain only a few bits of information about the user, but for most health care applications, the profile is a detailed professional biography of the user. With extensive training, board exams, state licenses, hospital privileges, certificates of CME and ongoing QA processes, health care professionals have worked hard for their credentials. The apparatus provides the opportunity to have their credentials work for them.

All of these credentials and more are already defined in the apparatus Sets and are ready to apply to a user profile. In addition to the dynamic professional biography, the user profile also includes an extensive array of personal preferences. Preferences are custom-built for each Product Category, though each product may add additional preferences. Personal preferences apply to both data entry as well as end-user access. To get a feel for how this level of control might impact real world applications, let's examine the Product Categories.

The Product Category area 900 is where the metadata apparatus is divided into functional units based on the complex item and each of its related elements. The complex item for which the apparatus was created is always one of the Product Categories. The other categories are the elements related to this complex item. Research is always included as a Product Category.

In health care, where the complex item is the human body, the principle category is Patient. Related elements include the people, places and things involved in patient care. The major Product Categories for health care are therefore: Patient, Research, People, Facility, Inventory, Task, Education, Reference and Quality Control. The categories shown in FIG. 4 are a representative sample and not an exhaustive collection.

The major advantage of using categories to build products with the apparatus is that the methods used to acquire, manipulate and present data, as well as the strategies and additional techniques needed to support the data are relatively consistent within a given category. Managing People with their qualifications, documentation, skill-sets and preferences is different than managing lectures, tests, textbooks and notes in the Education category. A final product may draw exclusively from a single category, or it may select features from several different categories.

It should be noted, that while each category has a unique subject, and the techniques and strategies of the category are optimized to manage data related to the subject, these techniques and strategies are not limited to any one category. In fact, the techniques and strategies of one category are often used in another category.

Education 905 is one of the most challenging categories, as nearly everything can be considered educational in one way or another. This means that the apparatus needs to recognize and be able to effectively apply labels to every kind of data. The nature of education also places unique demands on the metadata which is not required in most categories. The strategies and techniques used in the education category are described below.

The apparatus is already capable of labeling files with metadata defining the type of data contained in the file. These terms are organized in the Viewpoint table of the Examination section 305. Verbal, Sensory (physical), Electrical, Image, Sample, Photography and Rendering, along with the related tables defining each of these terms in precise detail, and those that define text about any of these terms are all part of the standard core. The terms are there, but how are they applied to the files?

The techniques used to apply metadata to educational material will evolve as techniques to use the metadata evolve. The apparatus is designed to apply fresh metadata to each individual file, and for continuous files like books or videos, apply metadata at preset intervals (e.g. every sentence or paragraph for text; every 15-30 seconds for video). As educational products are developed and technology advances, these intervals may lengthen or narrow.

Assume that every slide in a lecture, every 30 second audio clip, and every paragraph in a textbook or notebook has been accurately defined with metadata by the apparatus. As educational tools, these files are still just data—valuable, searchable data, but still just data. The next challenge is to impart educational value to the data so it can be organized into lectures, independent study, self-testing materials, quizzes, tests, and a full curriculum.

Like many of the Product Categories, Education uses a supplementary system to apply additional metadata to the files. This system is used to label files so they can be organized into a curriculum, create questions and answers pertaining to the files and assign a level to each (1-30). The system is also responsible for organizing the files into sections—didactic, laboratory and practical.

The level pertains to the level of education, as a lecture about the anatomy of the brain for a senior high student (L-12) would not be as detailed as a lecture for a senior radiology resident (L-20). Initially, questions and answers would be created manually, but in all likelihood, this process would soon be automated. Labeling the files to create a curriculum utilizes the traditional Lecture-Reading assignment-Self-test format, though will likely expand to involve some of the novel exercises offered by the apparatus.

The retrieval and display algorithms manage both the standard apparatus metadata and the category specific metadata. This supplementary metadata system and the management algorithms work together to provide the following functionality.

Provide a multimedia learning experience that does justice to the different data types that can be displayed, played and heard. The same functionality applies to lectures, self-testing and formal testing. Published books are also supported.

Note-taking platform that can be subjected to auto-labeling, with an option to auto-link notes to pertinent segments of a lecture and segments of the required reading.

Course time line for both professor and student showing the entire curriculum, including lectures, required and suggested reading, suggested self-test exercises (if applicable), formal quizzes and tests. Remedial lectures and additional reading also added when completed.

Transparent tracking of results on formal tests with an option for automatic formatting of a lecture based on the metadata attached to the questions answered incorrectly, for both informal and formal testing. Each 'remedial' lecture viewed is automatically documented on the course time line.

Provide an academic record. At the completion of the course, the credits earned are automatically added to the student's academic record, which is a part of the user profile, with a breakdown of the course content using the apparatus metadata (1 hr. minimum).

Reference 910 is similar to Education in that every kind of data needs to be supported. Some of the functionality described above is also important here [0285, 0290]; however, the focus of Reference is on the practicing health care professional.

Health care professionals rely heavily on reference materials to perform at the highest level and stay up-to-date in their practice area. The enormous volume of information in any one area of health care has made it nearly impossible to keep up with all the new advances reported in the literature. Changes in practice guidelines, internal protocols, insurance, quality control and credentialing requirements also impact the day-to-day practice of health care professionals. This category was designed to be a comprehensive reference resource for health care professionals.

The unique features of the Reference category center around a reference library designed and updated exclusively for one specific health care professional—the one that signed in. The supplementary metadata system in this category is responsible for defining the format of the reference material, organizing the materials within each format and applying descriptive titles.

The different Formats for reference material include Notes, Protocols, Procedures, Articles and Lectures. Each of these formats is organized like a book, with the supplementary system offering the user options for the book's sections and chapters. These options are derived from the metadata attached to the material used in the book.

Entire published books are also supported in the Reference category, just as they are with Education. These books are included on the shelf with the custom reference library; however, the sections and chapters of published books cannot be altered without permission.

The user profile plays an important role in the Reference category. Through the personal attributes defined in the People and Task categories (discussed below), the individuals level of education, training, specialty, subspecialty, and responsibilities all direct the supplementary system to identify and organize reference materials.

The retrieval and display algorithms manage both the standard apparatus metadata and the category specific metadata. This supplementary metadata system and the management algorithms work together to provide the following functionality.

Provide an intuitive interface that displays the user's library and provides an appropriate multimedia environment to both review and edit existing library books, as well as create new books.

Security and partitioning strategy that allows sensitive and non-sensitive data to coexist with minimal if any manual effort needed to view each kind of data.

Allow at least limited internet access. The open internet is separated/buffered from the apparatus; however, the metadata from any reference format can be used to search the internet. Automatic search options are also available. Search options are based on the user profile.

Method for incorporating materials from internet searches into the appropriate reference format for that user. For automatic searches, the applicable reference formats are automatically updated.

People 915 is one of four categories that share many common elements (People, Task, Facility and Material). Instead of using the apparatus to apply metadata to computer files, the apparatus generates a file to label. For People, this file becomes the personal inventory of an individual in the health care profession. The other three categories can also be viewed as detailed inventories of health care Tasks, Facilities and Materials.

Using the apparatus to define people, places and things in health care, as well as the tasks performed by each, creates a very powerful management tool.

For the individual, the personal inventory is a complete history of their academic achievements, level of training, skill sets, and interests relevant to health care—all in one place, precisely defined and protected. Their interaction with the apparatus, and products that use the apparatus, is immediately enhanced as their inventory is a key component of their user profile. Data entry and data access including interface layouts, educational and reference materials are all automatically configured for them, as are the health-related computer products they use every day (to be discussed later).

As a management tool, having detailed, consistent data on each individual eliminates inefficiencies and allows the products that manage people to do more—much, much more. Some of management scenarios include: Practice management, Hospital management, Quality Control, Continuing Medical Education (CME) and managing both Hospital Privileges and State Licenses (MLHP).

The supplementary metadata system in this category is responsible for defining the format of the skill-sets and contact information, organizing the materials within each format and providing a framework for the academic record and supportive documentation. The system must also incorporate date-time stamps and accommodate both positive and negative feedback from the Task category. Definitions for support personnel are also created (e.g. maintenance, secretarial, volunteers, etc.).

The retrieval and display algorithms manage both the standard apparatus metadata and the category specific metadata. This supplementary metadata system and the management algorithms work together to provide the following functionality.

Provide an intuitive interface that effectively displays summary information and a method to drill down on specific data elements. The interface should also be constructed to rearrange elements to best serve the perspective of the user accessing the apparatus based on their user profile. The summary section must also include space for a photograph and a short biography, both of which are also part of the user profile.

In Task 920 the apparatus creates a file for every task that can be performed in health care, and defines that task with the metadata. These definitions make extensive use of Sets like Device, Work, Therapy and Examination. The files (tasks) are organized by the diagnostic category to which they apply.

There are three major reasons why a category should be devoted exclusively to Tasks. The first reason is that tasks are the link between the health care system and the patient. Unless he performs the surgery, a surgeon is just a very educated consultant. The second reason is that the subjective term Quality has so many definitions, and the definitions not only depend on what is being defined, but when. Health care is fickle. The final reason is that it couldn't happen any other way. So many tasks can be performed by any number of trained professionals in any number of different facilities, or parts of a facility, so adding tasks to the People, Facility, Material and Patient categories just wouldn't work.

The supplementary metadata system in this category is responsible for defining Tasks, organizing them by People, Facility, Material and Patient, and assigning quality values. Complications are also related to each task. The system must also incorporate date-time stamps and accommodate both positive and negative quality values. A method to incorporate written descriptions, quality guidelines and tutorials for each Task, or class of related Tasks, is also required.

The retrieval and display algorithms manage both the standard apparatus metadata and the category specific metadata. This supplementary metadata system and the management algorithms work together to provide the following functionality.

Provide an intuitive interface that effectively displays summary information and a method to drill down on specific data elements. The interface should also be constructed to rearrange elements to best serve the perspective of the user accessing the apparatus based on their user profile.

Generate appropriate survey materials for patients and health care professionals that can be entered into the apparatus, or products using the apparatus. Appropriate technical readouts from devices and logistical surveys also need to be defined and created.

Facility 925 shares features with People, but instead of defining an individual, the apparatus creates a file for a facility and defines it with metadata. By defining a facility, and each part of a facility, with precise metadata about the procedures, therapies and disorders that facility is able to accommodate, the management of the facility is greatly enhanced. When matched with the metadata definitions from the People, Task and Material categories, the ability to objectively evaluate and manage a facility is greatly enhanced.

Examining the utility and efficiency of facilities is also an important part of creating a more cost-effective health care system. At some point, low risk, high traffic patient interactions need to be matched with an appropriate facility layout, just as high risk, low traffic interactions require a different layout. Utilizing existing space and creating new spaces to better serve patient care both benefit from the precise definitions used to define facilities. This is but one of the many possible research applications for the apparatus.

The supplementary metadata system in this category is responsible for defining the format of facility parameters so as to satisfy the established certification requirements applied to facilities, organizing the parameters and providing a framework for record keeping and supportive documentation consistent with those currently used for facility management. The system must also incorporate date-time stamps.

Some of the parameters used to define a facility are Title (Hospital, clinic, urgent care, imaging center, surgery center, etc.), Departments and Designation (specialty programs such as level I trauma, transplant, teaching, etc.). Facilities that are part of a larger system, and those that have more than one physical location are grouped into Systems.

The retrieval and display algorithms manage both the standard apparatus metadata and the category specific metadata. This supplementary metadata system and the management algorithms work together to provide the following functionality.

Provide an intuitive interface that effectively displays summary information and a method to drill down on specific data elements. The interface should also be constructed to rearrange elements to best serve the perspective of the user accessing the apparatus based on their user profile. The summary section must also include space for a photograph and a short biography.

In Material 930 the apparatus creates a file for every device, medicine, and piece of equipment used in health care, and defines that material with the metadata. These definitions make extensive use of Sets like Device, Therapy, Prevention and Examination.

Some of the materials used in health care have already been defined in the core (e.g. devices and supplements such as drugs, vitamins, IV solutions). Defining the rest of the equipment used by a facility to provide care such as computers, software, scalpels, catheters, slides, beds, bandages and cups is critical to facility management and reimbursement schedules.

The supplementary metadata system in this category is responsible for defining Materials not yet defined by the core, organizing them and creating a perishability scale that can be applied to the materials. The system must also incorporate date-time stamps and accommodate both positive and negative quality values. A method to incorporate written descriptions, a photograph and vendor lists including pricing, delivery times and contact information is also required.

The retrieval and display algorithms manage both the standard apparatus metadata and the category specific metadata. This supplementary metadata system and the management algorithms work together to provide the following functionality.

Provide an intuitive interface that effectively displays summary information and a method to drill down on specific data elements. The interface should also be constructed to rearrange elements to best serve the perspective of the user accessing the apparatus based on their user profile.

Generate appropriate inventory and ordering materials including schedules for delivery, distribution, installation and training (where applicable).

Patient 935 is a hybrid category. Like People and Facility, the apparatus creates a file for an individual patient. Unlike any of the previous categories, the apparatus then creates a continuous time line and uses the metadata attached to elements interacting with the patient to define the patient.

Historically, one of the biggest challenges in delivering effective care to every patient has been the shear size of their paper medical record and gaps in the record caused by any number of factors (physician changes, patient moving, inappropriate storage, etc.). Early efforts to create electronic records have followed the same arbitrary divisions that were necessary in the paper age (lab results, x-ray reports, progress notes, clinic visits, vital signs, hospitalizations, medications, etc.). It may be electronic, but it's no better.

The apparatus strips away these arbitrary divisions and focuses on the metadata defining the elements interacting with the patient. While the final form of the health record is determined at the Product level, the ability to combine disparate tests, therapies and procedures by their common elements and present this data to the end user in a form designed exclusively for their professional perspective will completely revolutionize health care.

The supplementary metadata system in this category is responsible for creating a time line, defining elements that impact the patient, including those undertaken by the patient themselves, and organizing the metadata relative to the time line. The system must also incorporate date-time stamps and accommodate both positive and negative quality values. A method to incorporate written and audio notes, by both the patient and any other health care professional, is also required.

The retrieval and display algorithms manage both the standard apparatus metadata and the category specific metadata. This supplementary metadata system and the management algorithms work together to provide the following functionality.

Provide an intuitive interface that effectively displays summary information and a method to drill down on specific data elements. The interface should also be constructed to rearrange elements to best serve the perspective of the user accessing the apparatus based on their user profile.

Calendar display for past and future patient events. Examples of patient events include clinic visits, immunizations, medication start, stop and dose changes, hospitalizations, diagnoses, surgeries, therapies, etc. Auto-reminder features for future events are also included.

Support a multimedia experience that does justice to the different data types that can be displayed, played and heard, similar to that used in Education. Voice-recognition technologies are supported.

Note-taking platform that can be subjected to auto-labeling based on the record elements reviewed at the time the notes were generated.

Consultation interface to and from other health care professionals from within a patient's record.

Overview interface designed for the health care professional including their patient list, a professional calendar, auto-alert features for critical results on tests with auto forwarding to on-call practitioner when not scheduled to work, and a consultation module. Overview interface also includes options for reviewing lab, pharmacology and radiology data for those professional who prefer to work as they did with paper records.

Research 940 is a category designed to examine the core and supplementary metadata to identify and study relationships within and between elements defined by the metadata. The research may focus on a single medicine to determine its efficacy and what factors improve and reduce its effectiveness, or it may be focused on techniques to reduce overcrowding in the emergency room. Whatever the research subject, the apparatus is a ready-made laboratory.

The supplementary metadata system in this category is responsible for recording search parameters, organizing the results of the search and displaying the results as graphs, tables or animations. The system must also incorporate date-time stamps and accommodate both positive and negative quality values. Patient data must be anonymized, and the same process can be applied to other elements as needed. A method to incorporate written and audio notes is also required.

The retrieval and display algorithms manage both the standard apparatus metadata and the category specific metadata. This supplementary metadata system and the management algorithms work together to provide the following functionality.

Provide an intuitive interface that effectively displays summary information and a method to drill down on specific data elements. The interface should also be constructed to rearrange elements to best serve the perspective of the user accessing the apparatus based on their user profile.

Accommodate outside products for statistical analysis of the search results, and allow the export of anonymized data along with the analysis for publication.

Products 950 using the apparatus are not restricted to any one Product Category. They may focus on elements within one category, use elements of all 8 categories or utilize another, as yet undefined, category. The six sample products all incorporate elements from several categories. As with the Product Categories, supplementary metadata and software techniques are used to create the finished Product.

A product to manage a radiology organization is discussed in the detailed specifications section beginning on page 24.

FIG. 5 is a chart representing the Core—Health Care. It is a Schematic representation of lower level components. The apparatus core is divided into six basic sections. From the bottom up, Form contains terms to define every structural element of the Item from conception through life. Function adds terms to define the unique substructural elements, chemistry and/or electrical properties and the different functional pathways of the Item. Examination addresses the tests used to examine the Item, and catalogues the findings on these tests in both normal and abnormal states. Condition relates the findings on these tests to specific abnormal conditions including common associations of conditions and/or findings (syndromes). Intervention defines people, places and things used to maintain health and treat pathologic conditions. Application is the area where code combinations are used to define People, Places and Sets needed by a Product Category. For the rest of this discussion, the Item is the human body. For the body, Variation becomes Gender, Substructure becomes Histology and Chemistry becomes Biochemistry.

FIG. 5 is a schematic representation and does not illustrate the true relationships between tables in any given section. Examples of the actual relationships are included later in this document (FIGS. 6-10).

Figure 5A:
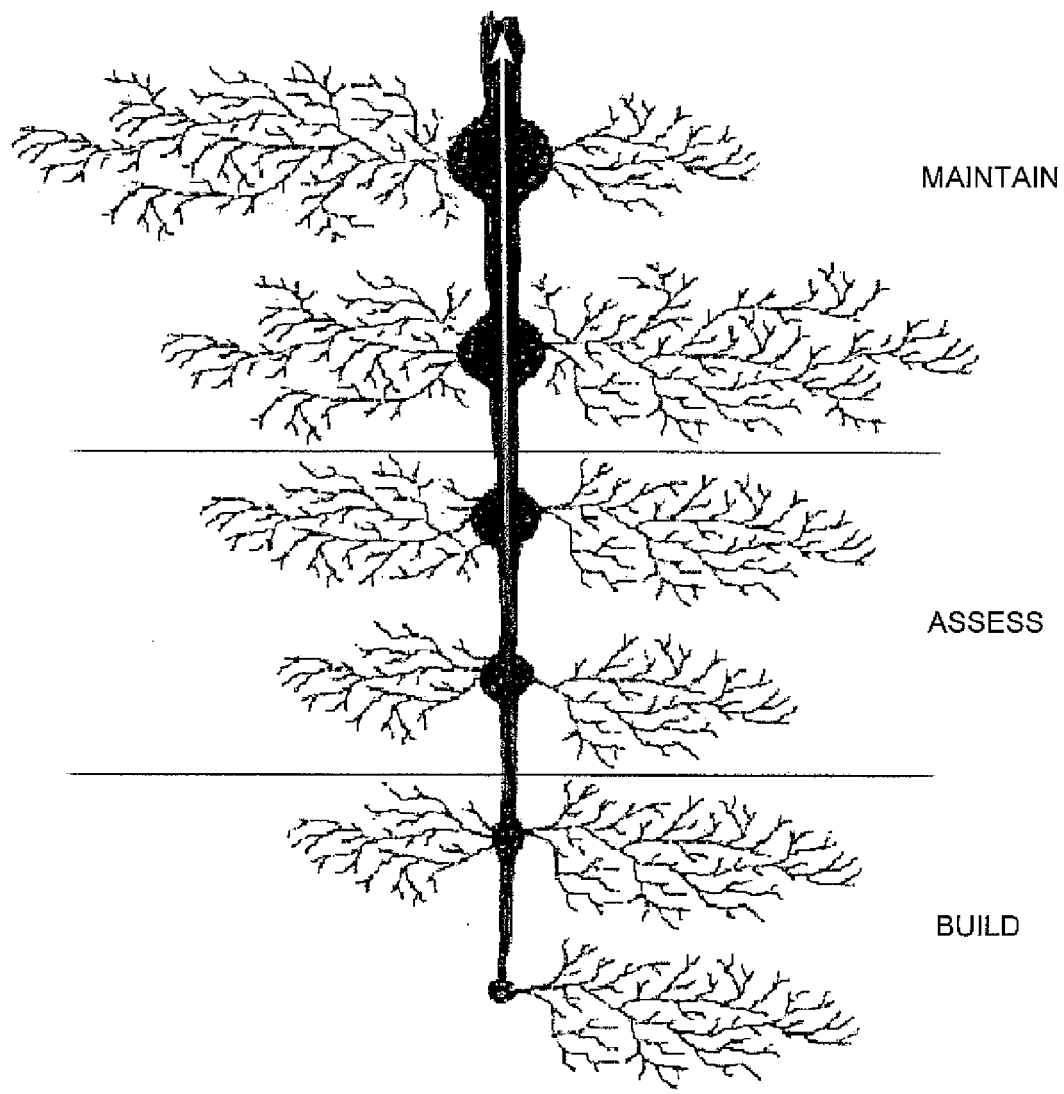
FIG. 5A is a diagram depicting Core sections as a root system.

The core sections depicted in FIG. 5 can be thought of as a tap root system with a tap root, or trunk, and branches on the left and right (see FIG. 5A). The trunk is composed of node tables linking the different sections to one another (100, 200, 300, 400, 500 and 600).

Node tables summarize the codes selected in the section tables and combine these codes with the code summary from the node table in the layer immediately beneath it. The node tables at the top are therefore larger (contain more codes) than those at the bottom.

The right-sided branches represent related tables of terms describing different attributes of the complex item. Each term is listed once.

The left-sided branches represent defined collections of right-sided branch terms. These collections are generally from the same level, though they can use definitions from deeper levels. These collections share a common theme (Function:Pathway, Examination:Mechanism, Condition: Syndrome Intervention:Protocol, Application:People & Place).

The terminology and relations needed to define the components of the left-sided branch can be thought of as a small right-sided branch positioned between left-sided collections and the node.

The node tables and mechanism can accommodate new left-sided branches (collections) and expanded right-sided branches when needed.

The 6 core sections can be thought of as 3 dual layers created to satisfy 3 simple objectives. From bottom-to-top, these objectives are Build, Assess and Maintain.

The core architecture was also designed to satisfy several important principles that should be kept in mind while reviewing the descriptions of FIGS. 5-10. These guiding principles are as follows.

1. A successful electronic platform for any industry must focus on the management of the industry elements.

2. The management apparatus must accommodate every element in the industry.

3. Every element must be defined in the same terms.

4. The terminology used for these definitions must reflect the intended applications and should only be as basic as to provide an accurate definition in the context of the industry. For example, when defining form, there's no reason to define parts of the form at the molecular level if the industry has no use for this definition or can't routinely examine structures at the molecular level. The same principle holds true for age. If the form changes slowly, there's no reason to define it at every second or minute.

5. The apparatus must expand to accommodate both new technologies that affect the industry and new demands placed on the management apparatus.

6. The apparatus must be responsive and not adversely affect the performance of management duties.

One of the performance features built into the apparatus is the extensive use of codes. Every term and table in the core is assigned a numbered code. As selections are made in each section, the codes corresponding to the selected terms and related tables are strung together and condensed in the node table of that section. These code strings become the subject of the terms and tables in the next section. When selections in this next section are made and condensed in its node table, both code strings become the subject of the next section. This process is repeated until the entire collection of code strings is packaged in the Application area.

The terms in FIG. 5 are generic and can be applied to any complex item. For the rest of this discussion, the complex item is the human body.

Keep in mind that FIG. 5 is a schematic representation. The parameters in each section are used to define specific attributes of the body, but their relations with other section parameters are not depicted here. Examples of relationships between parameters are provided in FIGS. 6-9.

Form 100 is where it all starts. The terms used to define form are separated from those used to define function, though both work together to define anatomy and physiology down to the biochemistry level. Form can be considered a snapshot of the body at a given time, while Function adds the juice to make it work.

The Form section has been designed to catalog all of the structures in the human body. Structure 125* is therefore the most basic terminology in the Form section.

The decision to select Structure as the base terminology in the Form section, instead of proceeding to the substructural levels (cellular, chemical and atomic) is based on two industry facts. The first is that methods to evaluate the body's form don't routinely examine parts smaller than structures. The second is that substructural parts are addressed more accurately with methods that evaluate function, and these methods do routinely evaluate parts at the cellular, chemical and atomic levels. For health care, the interface between structure and substructure is where the resolving power of imaging systems meets the low power magnification of histology.

Form is not simply a list of structures. Form also addresses the organization or arrangement of these structures. The Form section provides both the terms and organizational framework to accurately describe the body's form.

The basic organizational framework is provided by the Region 115* and System 120* tables. Region refers to the region of the body (head, face, neck, chest, etc.) while System refers to physiologic system (Nervous, respiratory, cardiac, etc.). Terms in these two tables are matched one-by-one to create multiple Region:System pairs. For every 'legitimate' Region:System pair, where legitimate means the body region contains structures in the paired system, the appropriate structures are cataloged. The specific approach to cataloging structures within this framework is described with FIG. 7.

Physiologic systems are extremely important to the operation of the human body, to health care professionals and to the apparatus, as many anomalies affect structures in only one system, or part of a system. By using Region:System pairs conventional physiologic systems are incorporated directly into the nomenclature, instead of relating systems to individual structures separately.

The form of the human body changes over time so a snapshot is of limited value if the age is not recorded. Age 105* is therefore an important consideration when defining the body's form.

Gender 110* also affects some parts of the body's form, particularly structures in the genitourinary system. These gender-specific variations in form are also more pronounced at certain ages.

The final table in the Form section is the Form table itself. Form 100 is a node table which connects all of the terms and table relations in the section with the Function node table in the next section.

The Function section 200 is the first of several functional layers applied to the Form of the human body. Function refers to the histology and biochemistry that empower structures with the ability to function. A muscle is a steak if the nerves don't fire and release their neurotransmitters to cause the muscle fibers to ratchet.

In the Function node table, the Histology of cells 205 and the Biochemistry within and between cells 210 are available to all of the structures in the Form section. A simple cell type that exists in many areas of the body can be matched to the exact structures in which it resides—anywhere or nearly everywhere in the human body. In contrast, a unique cell type or a cell with a unique biochemistry can be matched to the one structure where it exists.

By layering Function on Form, each of these cellular and biochemical elements can be defined once and yet have a widespread and very specific influence. This layered specificity is further amplified in higher sections.

Genetics 215 is also part of the Function section and includes everything from racial profiling to a specific mutation on a single chromosome. Genetics affect function. As genetic research continues, the apparatus is already prepared to record and tracking the effects of genetics on form and function.

Pathway 200P is the deepest left-sided branch in the core, and the first to be described. Unlike the right-sided branches, the terms in Pathway are not unique. Pathway is an area where collection of terms from the right-sided branches are defined. Like the Set described in FIG. 4, the terms and relations in a pathway collections are unified by a common theme.

These pathway themes not only provide an important functional layer to physiology, they're also easy to create and edit when research identifies new pathways or offers new evidence that an old pathway needs modification. By placing Pathway above the Form section, pathways can also include structures, histology and biochemistry within a physiologic system and between systems.

An example of a pathway within a physiologic system is the visual pathway. Photons of the appropriate wavelength interact with the rods and cones of the retina which generates a physiologic signal that is propagated along the visual pathway to the occipital cortex. The pathway includes the retina, optic nerve, optic chiasm, optic tract, lateral geniculate body, optic radiation and the occipital cortex. Furthermore, the lateral half of the retina uses the pathway on the same side of the brain, while the medial half crosses to the other side at the optic chiasm before proceeding to the opposite lateral geniculate body, optic radiation and occipital cortex.

Examples of pathways that involve more than one physiologic system are widespread and include nearly any part of the endocrine system and many elements of the nervous system. Structures in the endocrine system releases substances into the bloodstream that travel throughout the body to exert their effects. Some have an effect on a specific system, or structure in that system, while others affect many systems including the blood vessels themselves. The sensory, motor and autonomic parts of the nervous system also interact with other systems. Pathways provide a method to define these relationships.

The terminology and relations needed to define the components of Pathway are contained in a small right-sided branch which is actually located between Pathway and the node table Function [F2].

The lowest two core sections provide an incredibly accurate method to define the human body, but up until this point, these definitions are essentially theoretical. By itself, knowing how things work has little value. The next section provides the tools to move these definitions into the light of day.

The Examination 300 section is dedicated to both the techniques to examine the parts and pathways defined in the Form and Function sections, and the findings elicited by these examinations.

The examination techniques are organized by Viewpoint 305*. The Viewpoint table and related terms cover every possible technique for examining the body parts defined in the lower sections. Designed to accommodate every specialty in health care, the basic viewpoints include: verbal, sensory or physical contact, electrical, imaging, sampling, photography and rendering or drawing. All of the possible examination techniques are defined in tables related to these six viewpoints. A provision for text describing these techniques is also included. FIG. 8 addresses these techniques in more detail.

Because examinations can be thought of as snapshots of the body at a given time, using any number of different cameras, the date and time of each examination is recorded. And since each examination generates one or more findings, each finding is also date-time stamped. Date-time stamps are particularly important when using the apparatus for research or to define a patient.

A Finding 310* is defined as the result of a test or examination. A single examination can yield only one or dozens of findings. Findings can be normal or abnormal; however, that differentiation is left for the Condition section. Analogous to Structure in the Form section, Finding is the most basic element in the Examination section.

Unlike a Structure, a Finding is not usually limited to one or two terms and is frequently subjective. The same finding may also be described inconsistently or differently by authors and health care professionals. These challenges are addressed in the design of the Examination section.

The first approach is to partition findings by Viewpoint. Each Viewpoint narrows the number of possible terms used a Finding, as clinical terms such as 'cough', 'dizziness', and 'shortness of breath' are never used to describe a CT examination or an EKG.

The terminology used to describe different findings is also partitioned. Focused terminology modules are related to each technique in each Viewpoint to insure that the terminology matches the technique. The terminology modules are also related to one another to facilitate auto-labeling.

The issue of inconstant terminology is also addressed by relating each finding to a pseudonym look-up table. These look-up tables are dynamic and continue to collect terms as findings are added to the database. Examples of pseudonyms for 'increased' relative to T2 signal on an MRI scan include 'brighten' and 'lighten'.

Subjective findings, which are the most common findings, are graded objectively using the rheostat function. Examples of subjective findings include describing the intensity of enhancement on an MRI, the amount of stain taken up by a structure on a pathology slide, or the degree to which an organ or structure is enlarged or shrunken. This objective grading system is then related to subjective descriptors such as mild, moderate, severe and extreme.

A final safeguard to insure that the subjective terminology for Finding is entered properly, is the Preliminary status which is applied to the Finding(s) during the data entry process. A second observer, who is intimately familiar with the apparatus, must review new Findings and make sure they are entered properly. If the relations in the core need adjusting to accommodate a new or unusual term for Finding, this can be accomplished BEFORE the Finding is finalized.

As a left-sided branch, Mechanism 300M is organized much like the Pathway area. The primary function of Mechanism is to provide an area to create collections of findings based on a common mechanism of action. These mechanisms are dependent on both the Viewpoint and the particular Finding and basically answer the question—why does a technique exhibit a particular Finding?

The techniques in the Examination section vary tremendously in both sensitivity and specificity. A number of different techniques can be used to examine the same structure or collection of structures, while other techniques are only used to examine a specific attribute of a specific structure. Still others are very general and only reveal limited information about the entire body or large parts of the body. Regardless, these techniques, and the findings offered by each, are how we assess the body and diagnose disorders that affect the body. The apparatus is tailor-made for this application.

The terminology and relations needed to define the components of Mechanism are contained in a small right-sided branch which is actually located between Mechanism and the node table Examination [F3].

The Condition section 400 is where the findings in the Examination section are assembled to define a specific Diagnosis. Diagnosis 415 is similar to the most basic elements in the Form and Examination sections (Structure and Finding respectively).

Two tables in the Condition section interact with the findings to define a Diagnosis. These are Family History and Environment.

Family History 400FH is an historical record of all known diagnoses in relatives of the body. This table is a hybrid in that it is organized like a left-sided branch but can be used to help define a Diagnosis. It's also related directly to the Genetics table in the Function section so that both tables update one another when new data is added. Both the Family History and Genetics tables make extensive use of the rheostat functions to assess the body's risk for specific disorders based on both the data in the literature, and eventually the data in the apparatus itself.

Environment 405 can also impact the diagnostic outcome for a collection of findings. Many different environmental elements can affect both how the body functions at a given time, and it's risk of developing certain disorders. These elements include geography, magnetic/electric, radiation, gaseous, chemical, infectious, traumatic and nutritional.

Each of these environmental elements is defined in specific terms and related to the physical location of the body. In the initial version of the apparatus, the physical location of the body is defined by country, and in the US this is broken down by zip code. Future versions may incorporate GPS coordinates if more specific locations and shorter times affect the utility of the apparatus for specific applications. The initial geographic beak down for the US is detailed in FIG. 9.

The Environment and Diagnostic Category tables are then combined to create the framework for Diagnosis. Diagnostic Category 410 is a table of 16 terms created to compartmentalize every possible Diagnosis (see FIG. 9). Some of the categories share the same mechanism of action (Infectious), while others describe diagnoses in normal conditions (normal, normal variants, and pregnancy). Still others describe conditions related to development, both before and after birth (congenital, developmental). As with any categorical scheme with four dimensions, a diagnosis may reside within two or three categories [e.g. a medication (iatrogenic) causes a side effect (inflammatory) that results in a hormone deficiency (metabolic)].

The terminology challenges addressed in the Examination section, while not as severe, also apply to Diagnosis. Instead of many Focus modules, a single module is used to insure the terminology used for Diagnosis is consistent. Pseudonym look-up tables are again part of the apparatus.

The terms used for Diagnosis are frequently used for billing purposes. The ICD-10 codes for billing are mapped to the Diagnosis terms in the apparatus for products that use the apparatus to manage reimbursement. Because each Diagnosis in the apparatus has far more specific information about the patient, their condition and tests, the apparatus may well supplant the ICD code structure in the future.

A general definition of the word 'syndrome' is a complex set of concurrent things. In health care, these 'concurrent things' are generally pathologic disorders; however, in the apparatus, these 'things' can be anything defined by the core.

Syndrome 400S is the third left-sided branch and is organized like Mechanism and Pathway in the deeper sections. Examples of collections organized in the Syndrome area are found in every Diagnostic Category, including Normal. Any collection of definitions in and below the Condition section, including mechanisms and pathways, that can be unified by a common theme is defined in Syndrome.

For pathologic disorders, there are many named syndromes and a number of generic syndromes that haven't been named (e.g. viral syndrome). An example of a named pathologic syndrome is Kassabach-Merrit Syndrome which is the combination of a hemangioendothelioma (Diagnosis) and thrombocytopenia (Finding). As with Diagnosis and Finding, a Pseudonym table is provided for each syndrome.

The terminology and relations needed to define the components of Syndrome are contained in a small right-sided branch which is actually located between Syndrome and the node table Condition [F4].

The fifth core section is Intervention 500. As the name implies, this section is dedicated to detailing all of the external actions that can be directed at the human body, as defined by the deeper sections, to maintain health and treat pathologic conditions. Because this section describes different items directed at the human body, the organizational framework is necessarily different; however, maintenance requires frequent assessment so many of the techniques used in the Examination section are also employed here.

Instead of selecting a parameter as the most basic element, the Intervention section is designed to catalog the interventional techniques in health care. The apparatus divides interventional techniques into equipment, supplements and procedures. Because these three elements are constantly shifting, the organizational framework also provides the option to flag, inactivate and block any element for any number of different reasons.

Equipment 510 is defined as every piece of inanimate material used in health care from needles, syringes and band-aids to prosthetic joints and radiation generators used in cancer therapy. Computers and software are also considered equipment. Supplement 515 is defined as any non-equipment material introduced into the body and includes vitamins, IV solutions and all medications regardless of its mode of entry (i.e. oral, transdermal, IV, IM and trans rectal). Procedure 520 is defined as any 'purposeful interaction' with the body. Procedures include listening to a patient describe their current illness, dispensing supplements, and performing a CT-guided biopsy or a heart transplant.

Interventions are purposeful. The Purpose table 505 assigns purpose to each piece of equipment, supplement and procedure used to interact with the body and it's condition. The two main purposes are Diagnostic and Therapeutic, meaning each interventional element is diagnostic, therapeutic or both.

The Viewpoint and related tables from the Examination section are also used here to define diagnostic procedures, equipment and supplements. The same architecture used to catalog findings is used in reverse to define the elements used to generate them.

Therapeutic procedures, equipment and supplements are also found in every Viewpoint; however, unlike diagnostic elements, a small minority of therapeutic elements can't be defined by the diagnostic Viewpoints. For these elements, a second Viewpoint table is used (Viewpoint 2). The two Viewpoint tables function as a single entity when defining diagnostic and therapeutic procedures, equipment and supplements.

A Method table, like that used in the Examination section to define text about the items described in the section, is also included in Intervention.

The temporal relationship between the examinations, interventions and Diagnosis is also defined in the four upper level sections, including Intervention. These relationships are regulated by Date:Time stamps applied to critical tables that provide the temporal data for different management endeavors.

Relations between stamps are also monitored and set to trigger specific actions including adjusting shifts in 'event-specific' terminology. Examinations and interventions performed before a diagnosis is made go by different names than those performed during or after the Diagnosis is established (e.g. Diagnostic: screening, work-up, surveillance; Therapeutic: prevention, therapy, rehabilitation, maintenance).

Protocol 500P is the fourth left-sided branch and is organized like those in the deeper sections. A protocol is defined as a detailed plan. Protocols are everywhere in health care, and they can be diagnostic, therapeutic or both. Protocols also frequently include elements from both the Examination and Condition sections. An example of a clinical protocol would be the ordered procession of diagnostic examinations and therapeutic interventions initiated by the clinical symptom of Chest pain.

Protocols also apply to all Support interventions such as preparing Equipment and Supplements for a Procedure, verifying a physician's order for a narcotic prescription, maintaining and testing medical devices and managing different parts of the electronic health record.

The terminology and relations needed to define the components of Protocol are contained in a small right-sided branch which is actually located between Protocol and the node table Intervention [F5].

Application 600 is the sixth and highest core section. Unlike the five deeper sections, Application does not have right-side branches. The only unique terms and architecture in the Application area are in the Focus tables used to define Sets [F6].

Each of the left-sided branches in the Core has Focus tables to organize the terms used for the collections, but [F6] holds the distinction of being the one that organizes the electronic dictionary and creates the most complete definitions using the core language.

Place is one of these definitions. The terms to define individual rooms by the activities they can or do support is an important tool for creating an accurate facility profile. Departments are then built room-by-room, and facilities built department-by-department. Designations such as level I trauma, transplant or cancer center are also applied as are research and education. This detail is extremely important for facility management when people, tasks and materials are added in the Product Category area.

Like Facility, People aren't defined until the Product Category area; however, all of the professional components of the user profile are created in [F6] including Training, Specialty and Practitioner definitions.

FIG. 6 is a chart representing terms and relations for AGE 110—Health Care. The terms describing the Age of the human body are based on physiologic and clinical definitions. The age of the body is an important factor in assessing not only what types of conditions may affect the body, but also what impact they may have on the future development and life of the body. Some conditions preferentially affect young bodies while others affect older ones. The age of the body also determines who is involved in care and where that care is provided. Diagnostic methods, prevention and therapies also depend on the body's age.

The Join tables and Join terminology are not part of this figure. The codes assigned to each table and term are also not included.

The Age of the body 105 is mapped against a time-line of days. Conversion tables convert days to weeks, months and years. From this continuous time line, progressively larger age ranges are defined until there are only three categories—Adult, Pediatric and Intrauterine.

The age ranges for each category and subcategory have been selected to define important stages in the development, assessment and maintenance of the body.

For applications that examine the body in the context of a patient, the patient's age is calculated by subtracting the date of birth from the date of service. Service refers to any contact between the elements defined by the apparatus and the patient. Patient age is then used by the apparatus to focus pertinent features. Age is a part of the Patient profile.

The principle strategy used to focus the apparatus is to define the body's Form for every Age. Once each age-dependent Form is defined, all of the definitions in the upper level sections can be directed specifically to one or more Forms. The other elements used to define Form are Gender, Region, System and Structure.

Figure 7:
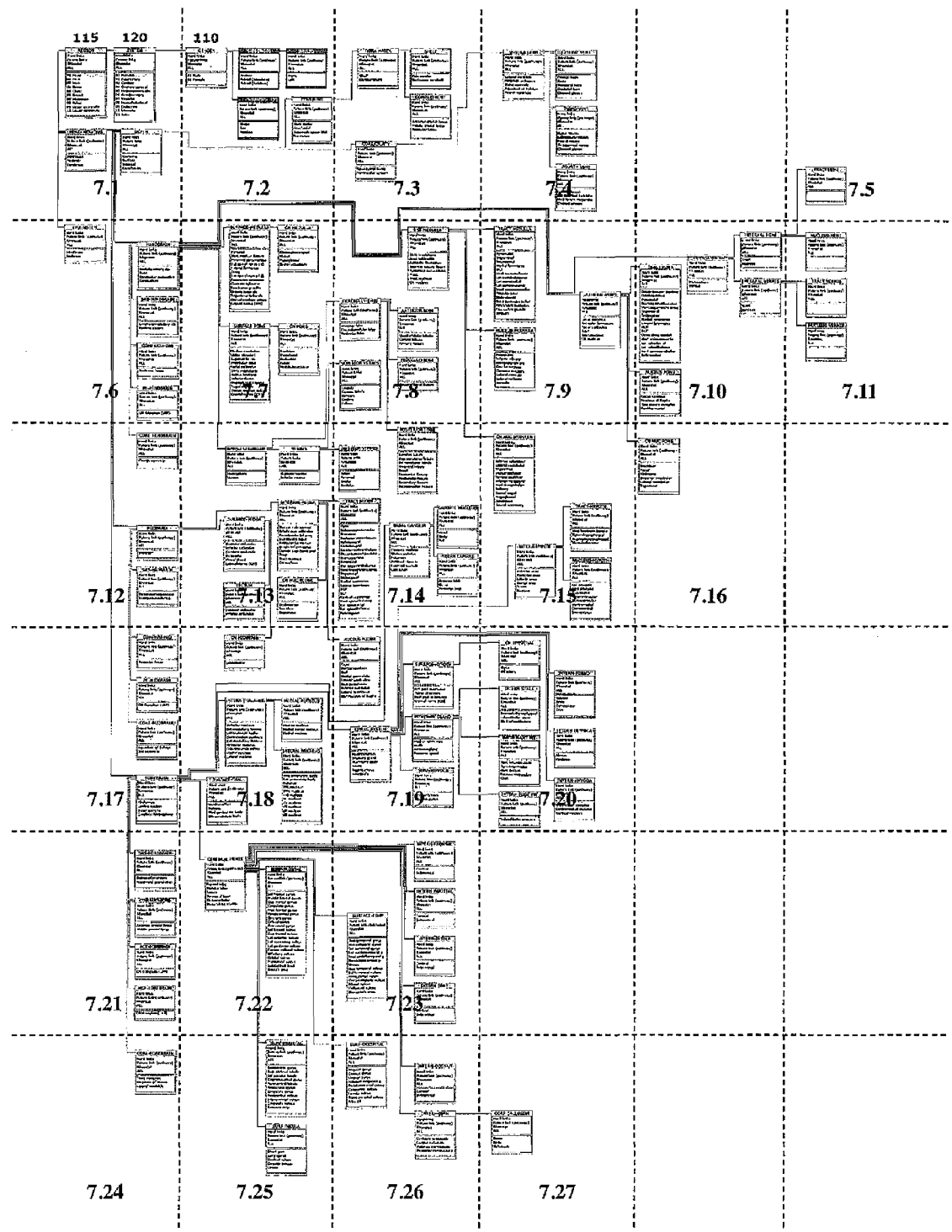
FIG. 7 is a chart showing a detailed view of the terms, tables and relationships for the Structure parameter in the Core's Form section, where Region=Head, and System=Nervous. Schematics for other Region:System pairs are also integrated with the Age parameter in the Core's Form section, and though these are not shown here, the organizational terminology and approach shown in FIG. 7 are consistent for all Region:System pairs.

FIG. 7 is a chart representing terms and relations for STRUCTURE 125—Health Care. The terms for the Structures of the human body are based on their location, physiologic system and how they might be evaluated using the various Viewpoints in the Examination layer (see FIG. 8). The terms in the Region and System tables are paired one-by-one and each time structures from the system are found in the anatomic region, an inventory of structures is generated. The organizational scheme for each inventory depends on the—anatomy, physiologic system and viewpoints used to examine the structures, but the approach is consistent for each inventory (e.g. solid organs: covering, surface, internal and core/cavity). Because structures in the genitourinary system differ between men and women in some regions, the inventory accommodates both.

The Join tables and Join terminology are not part of this figure. The codes assigned to each table and term are also not included except for the Region, System and Gender tables.

The body is divided into ten (10) different regions. These divisions are based on both the apparatus design and functional definitions used in health care today. These regions 115 are: head, face, neck, spine, chest, breast, abdomen, pelvis, upper extremity and lower extremity.

There are also eleven (11) physiologic systems in the body. Some systems are confined to one or two regions, while others are found in every region. The systems 120 are: nervous, respiratory, cardiac, gastrointestinal, hepatobiliary-pancreatic, genitourinary, vascular, musculoskeletal, endocrine, immune and skin.

Structures are found in both regions and systems and are the basic unit in the Form section. The following 3-phase approach is used to inventory all of the structures in the human body.

In the first phase, terms in the Region and System tables are paired one-by-one to create Region-System pairs. Each time structures from the system are found in the anatomic region of the pair, an inventory of structures is generated. This process is repeated until all of the Region-System pairs have been addressed. The initial inventory is for 'ALL' adults in the 30-35 year age group.

In the second phase, the structures unique to each Gender 110 are added. These additions are generally in the Breast and Pelvis regions for the Genitourinary system.

In the third and final phase, the inventory is expanded to accommodate every age range. Starting with the 30-35 years age group, the inventory is examined with respect to each of the 100 age groups to insure that the appropriate terms and organization are present. With regard to Form, most of the additions are in the Pediatric and Intrauterine Age groups and are generally restricted to adding new summary tables to accommodate developmental changes.

FIG. 7 illustrates the organization and terms of the initial inventory for the Region-System pair 'Head-Nervous'. In addition to the specific terms in this Region-System pair, several organizational features shown here are repeated throughout the inventory.

The universal tables 'Sidedness' and 'Mapping' (shown in dark gray) are used with every Region-System pair.

Sidedness defines structures as midline or paired. Paired structures can also be absolute, where the structures exist on opposite sides of the longitudinal axis drawn through the center of the body, or relative. Relative refers to structures that exist to the right or left of midline, but still have relative right and left designations. The liver is one example. In the normal condition, the liver resides to the right of midline, but has right and left lobes. The medial segment of the left lobe is frequently to the right of midline (i.e. absolute right; relative left).

Mapping defines structures by their Shape, Size and Position. Size is defined in mm and is related to conversion tables for cms, inches and feet. Since Size is defined in all three planes, tables to convert distance to volume are also included. Position is related to tables that define the structure by coordinates. These coordinates are mapped against an age-matched standard. The coordinates and Shape definitions both exploit 3D modeling algorithms to define the Surface of each structure in space. Once these mapping strategies are integrated with the apparatus, Proximity tables will be added to define more precise physical relationships between structures.

The divisional terms in the Region-System table itself are the most general in the inventory.

The Depth approach is used for every Region-System pair in the inventory. Covering, Surface, Internal and Core/cavity can be applied to structures in every system. These designations are also consistent with the diagnostic and therapeutic techniques in the higher sections. For 3D modeling, Surface and Core/cavity are both considered surface definitions.

Structures repeated in two or more different tables are actually listed once in another table and related to the different tables. These other tables are not depicted for space reasons.

Several organizational features in the Form section are also used to organize terms in Histology and Biochemistry in the Function section (not shown here).

FIG. 8 is a chart representing terms and relations for FINDING 310—Health Care. The terms for Finding are dependent on the Form and Function of the structure(s) and the technique used to examine this Form and Function. In the apparatus, these techniques are addressed in the Viewpoint table. Six basic viewpoints are used to generate findings, each with its own unique organization and techniques. Focused terminology modules have also been created for each Viewpoint to insure that the descriptive terminology for a Finding, Viewpoint and technique match. In this figure, a Finding is represented by [---], and a Focus module is represented by FO1. The Focus modules are related to one another to facilitate auto-labeling (not shown). An example of a Focus module is shown for MRI-F10, Findings from each Viewpoint can be passive (spontaneous) or elicited by a device or observer, and the Viewpoint form and method tables provide this distinction. Text, renderings and photographs about findings are also options. Findings are assigned a preliminary status when they're first entered. After review and confirmation by a second observer, a Finding is finalized. The findings for Sample are abbreviated in this figure because of space constraints.

The Join tables and Join terminology are not part of this figure. The codes assigned to each table and term are also not included.

A Finding is defined as 'any piece of information about the condition of the human body available to a health care professional'. This definition includes—Signs, Symptoms and the specific findings on every test that can be performed on the human body. By definition, a Finding is independent of both the ability of the health care professional to recognize it and their ability to understand its implications.

The apparatus is designed to segregate findings from all subjective and objective measures of its value. All value is applied to a Finding in the Condition section. This approach is necessary as a normal Finding at one age may be abnormal at another age, or in another circumstance; however, this segregation also allows findings to be examined independently. The ability to monitor findings in different circumstances is a powerful tool to uncover previously unknown relationships. Artifacts and incidental findings that had been of little value may prove to be important diagnostic or therapeutic clues.

Each table in the apparatus is constructed with links to one or more rheostats. Rheostat is a general term that describes a collection of tables working together to quantitatively modulate terms in another table (or tables).

Rheostats are used in a variety of ways throughout the apparatus and are frequently placed between elements in two different sections. All rheostats use a scale (numeric or percentage) and can be connected to any table, or collection of tables, by activating the rheostat for those tables. Examples of rheostat functions include defining the intensity of a positive Finding (1-10) and defining the frequency in which a Finding is present in a Diagnosis or a Diagnosis is part of a Syndrome (%).

The Existence tables in FIG. 8 are an example of a rheostat. Every table related to Viewpoint can be quantified by the Rheostat I scale. New rheostats can also be added at any time to satisfy the needs of upper level sections, including product Categories and Products.

Findings are purely Diagnostic.

The six viewpoints in the Viewpoint table 305 contain all of the different methods currently used to examine the human body. As each Viewpoint is applied to the Structures, Histology and Biochemistry defined in the Form and Function sections, specific findings are generated.

Each Viewpoint has its own unique organizational structure which was created to accommodate the Diagnostic techniques in the Viewpoint. The basic divisions are illustrated in this figure, but because each Viewpoint is applied to everything in Form and Function, a complete list of all Findings is beyond the scope of this document. Three of the key organizational features in FIG. 8 are as follows.

Findings are focused. Instead of a single very large list of findings, the apparatus sequentially segregates findings by Form, Function and Viewpoint to create a very specific, short list of terms.

The terminology used for findings is also segregated. These focused collections of terms are called Focus modules. Focus modules are created for each technique of each Viewpoint to insure specific, consistent terminology that matches the technique and Viewpoint. [F10] is an example of a Focus module for MRI.

Pseudonym tables are attached to each Finding table. The actual Pseudonym tables are grouped together to facilitate management and updating, but the collection of tables is related to each Finding table through 'Hard Links'. Pseudonym tables are also used throughout the apparatus.

While many examinations that address Form are passive, examinations that assess function frequently require some form of stimulation. The Elicited (Active) term in the Form table adds this important element. Elicited examinations range from asking verbal questions during a physical examination, to striking the patellar tendon with a reflex hammer to observe the response, to exercising the heart to observe the EKG or radionucleide distribution on an imaging exam to adding a chemical or supplement to the blood and then sampling the blood to see if the appropriate chemicals are produced by the body.

With few exceptions, the apparatus is designed so that the metadata for Finding, Form and Function can be applied directly to computer files for each technique in all six viewpoints. The Method table is introduced to provide a method to apply the exact same metadata to Text, Rendering and Photographic files that describe the specific Viewpoint files.

The Indirect option in the Method table is a critical apparatus feature for three main reasons. The first reason is that Text makes up a large percentage of all the data in health care, and without the ability to label text, the apparatus wouldn't satisfy guiding principle #2 on page 18 which is 'The management apparatus must accommodate every element in the industry.' Secondly, from a management perspective, it's important to distinguish between an encounter and the Text about an encounter. The people, places and things needed for an encounter are different and more complex than those needed to record it. The third reason is that strategies to divide, label and rearrange Text lend themselves better to automatic processes and are slightly different from-than those used elsewhere in the apparatus. The two main organizational parameters for text are Length and Format.

Rendering includes Schematic, Illustration and Animation. Schematic addresses all graphic representations of Text such as graphs, tables and flowcharts. Illustration and Animation are self-explanatory.

Photography* serves double-duty as both a Direct and Indirect method, though it's almost exclusively an Indirect method employed to document techniques in other viewpoints. The Direct application comes from special lighting techniques used during the exposure that provide added value to the photograph as a diagnostic tool. Tangential lighting for surface and skin disorders and trans illumination for masses are two examples.

The metadata of educational and reference materials almost exclusively employs the Indirect methods of Text, Rendering and Photography.

Figure 9:
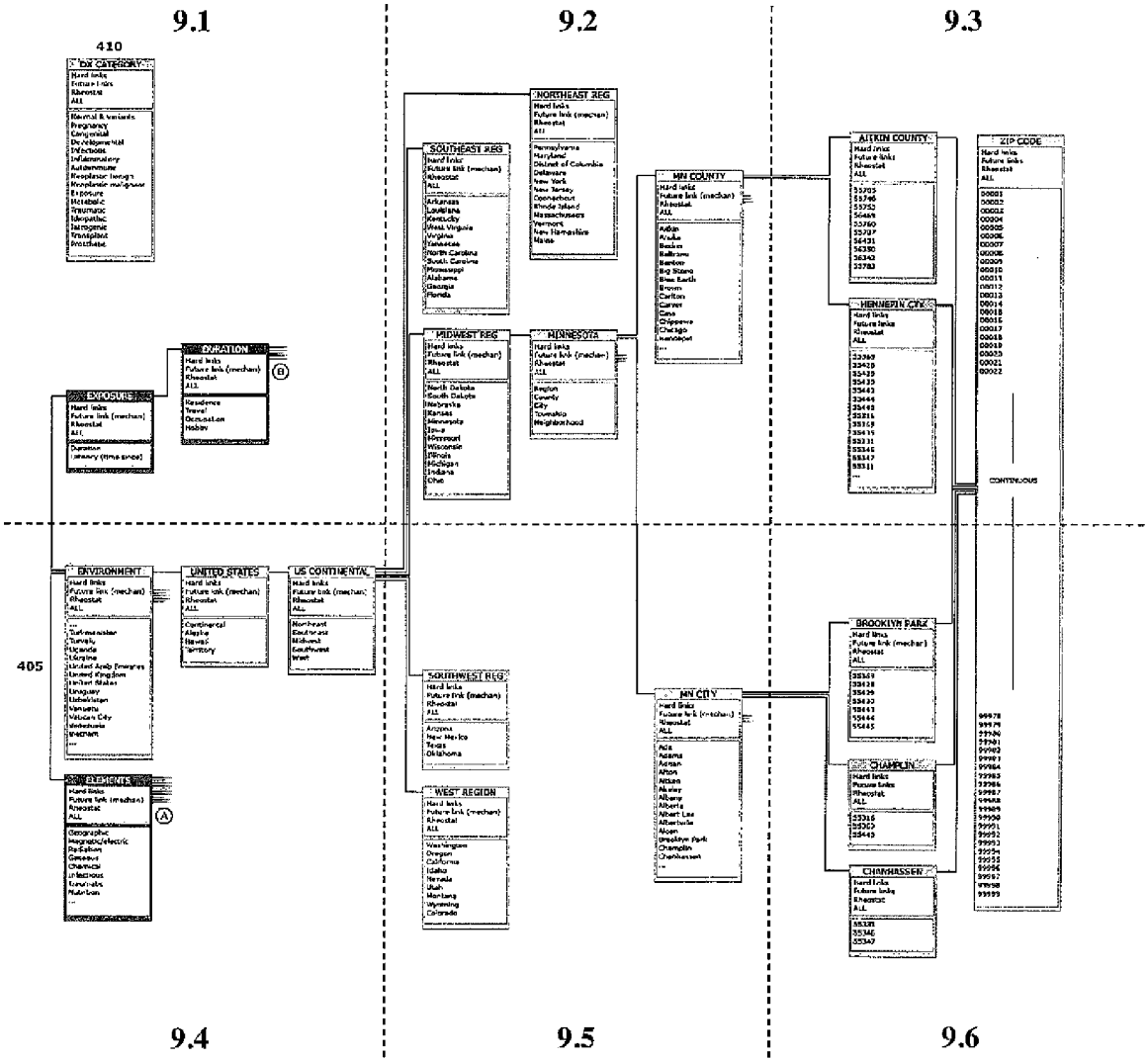
FIG. 9 is a chart showing a detailed view of the terms, tables and relationships for the Environment and Diagnostic Category parameters in the Core's Condition section. The Environment parameter not only adds important terminology regarding a body's exposure at home, work or travel, it also 'globalizes' the Apparatus so that the Apparatus is equally effective anywhere in the world.

FIG. 9 is a chart representing architecture for terms and relations ENVIRONMENT 405 & DIAGNOSTIC CATEGORY 410—Health Care. The terms for the Environment impacting the human body are based on standard geographic locations. In the US, zip codes are used to define these locations. Postal codes, tribal boundaries and even GPS coordinates may be used to define locations around the world. Once defined, these definitions are used to create categories, subcategories and sub subcategories to describe both environmental areas and different sized populations. The environmental elements that could impact the body are then related to these locations, as are the time spent in the location and the latency of this exposure relative to the date when the body is examined. Each environmental element is defined in detail. Time spent in each location is also divided into categories such as residence, travel, occupation and hobby. Diagnostic Category is a simple table used to catalog Diagnoses. The definitions for Environment are abbreviated in this figure because of space constraints.

The Join tables and Join terminology are not part of this figure. The codes assigned to each table and term are also not included.

The terms in the Elements table are only a partial list, and each term is related to tables describing the Element in detail (A). Terms in the tables for Geographic include temperature, humidity, elevation and terrain, as well as indigenous animals and plants. Tables for the other Elements are generally reserved for hazardous materials, though depending on the demands of the final Product, these tables can be expanded to include nearly anything.

Many of the terms in the Elements table are related to their counterparts in Diagnostic Category.

The Duration of exposure is related to a continuous time line in hours. Conversion tables translate time into hours, days, weeks, months and years. Additional tables describing different professions and hobbies are related to Occupation and Hobby (B).

Diagnostic Category 410 is used as a guide to catalog specific diagnoses in the Condition section. Using the findings generated in Examination, the Condition section combines these findings with Environment and Diagnostic Category to establish a differential Diagnosis—or list of possible diagnoses. These initial Diagnoses are general and may reside in many different categories. With more information, a final Diagnosis is established. Because a final Diagnosis includes the cause, the Diagnosis can be narrowed to one category, though two or even three Diagnostic categories are common.

Figure 10:
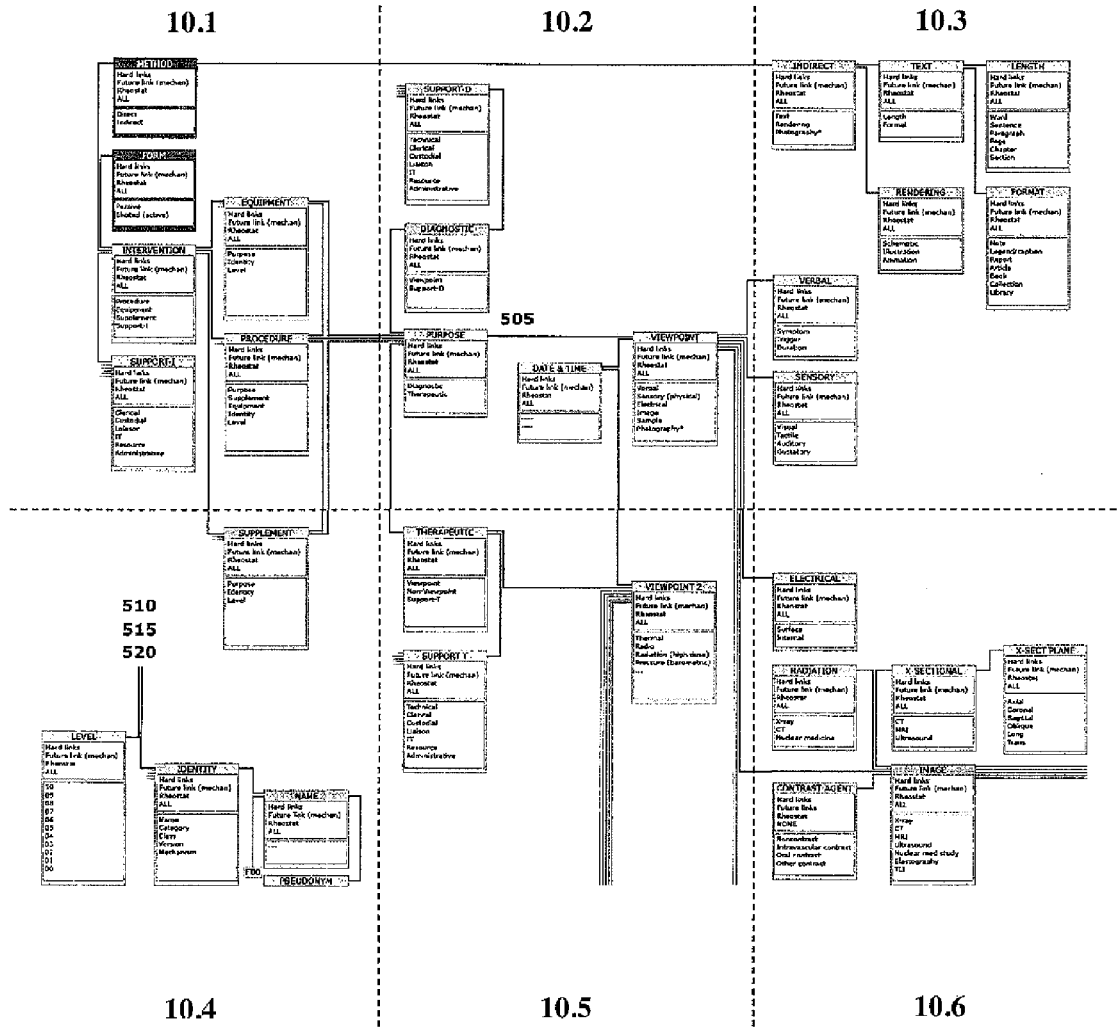
FIG. 10 is a chart showing a detailed view of the terms, tables and relationships for the Intervention section of the Core. Intervention addresses the inanimate elements used to maintain health and treat conditions affecting the human body which are categorized by both the Viewpoints used in the Examination section, and a supplementary table of procedural viewpoints (Viewpoint 2).

FIG. 10 is a chart representing architecture for terms and relations in INTERVENTION 500—Health Care. The terms for the inanimate elements involved in maintaining the health and treating conditions that affect the human body fall into three categories—Equipment, Supplement and Procedure. Each of these elements is defined not only by its identity (name and other element parameters), but also by its specific interactions with the body as defined in lower sections. Notice that supplements and equipment can be defined independently or as part of a Procedure. Procedure is also independent. All three elements can also be Diagnostic, Therapeutic or both. Elements that are involved but don't interact directly with the body are considered Support. Every item from Equipment, Supplement and Procedure that does interact with the body is classified by either Viewpoint, which is organized the same as Viewpoint in the Examination section, or Viewpoint 2. Viewpoint 2 lists all therapeutic views not included in Viewpoint. Date-Time stamps and a method to label text, renderings and photographs about interventions are also included. The definitions for Intervention are abbreviated in this figure because of space constraints.

The Join tables and Join terminology are not part of this figure. The codes assigned to each table and term are also not included.

Equipment, Supplement and Procedure are the elements defined in the Intervention section.

Viewpoint is an important organizational feature of Intervention, though the relations defined in the Examination section are used in reverse. Instead of defining progressively more specific diagnostic techniques and findings, these techniques and viewpoints are used to help define the Equipment, Supplements and Procedures involved in performing the diagnostic workup, and in most cases, the Therapeutic interventions.

Because defining the element is the focus of the section, the Pseudonym table and Focus module are related to the element and are absent from the Viewpoint tables. In addition to Name, elements are also defined by Category, Class, Version and Mechanism. The tables for each of these attributes follows established conventions (not included).

The Viewpoint 2 tables contains additional techniques to define therapies not already addressed in the Viewpoint table.

New Diagnostic techniques are added to Viewpoint as they are developed. New therapeutic techniques are added to Viewpoint 2 if they can't be defined in Viewpoint.

Examples of common interventions and their defining Viewpoints are:

Verbal: Advice and recommendations.

Sensory: Surgery, invasive procedures (IVs, catheters, etc.) and physical manipulations.

Electrical: ECT, electrocautery and defibrillation.

Image: Fluoroscopic, ultrasound and CT-guided procedures.

Sample: IV solutions, vitamins and pharmaceuticals.

The Method table and relations are also part of this section and accommodate Text, Rendering and Photography of Interventional elements.

Figure 11:
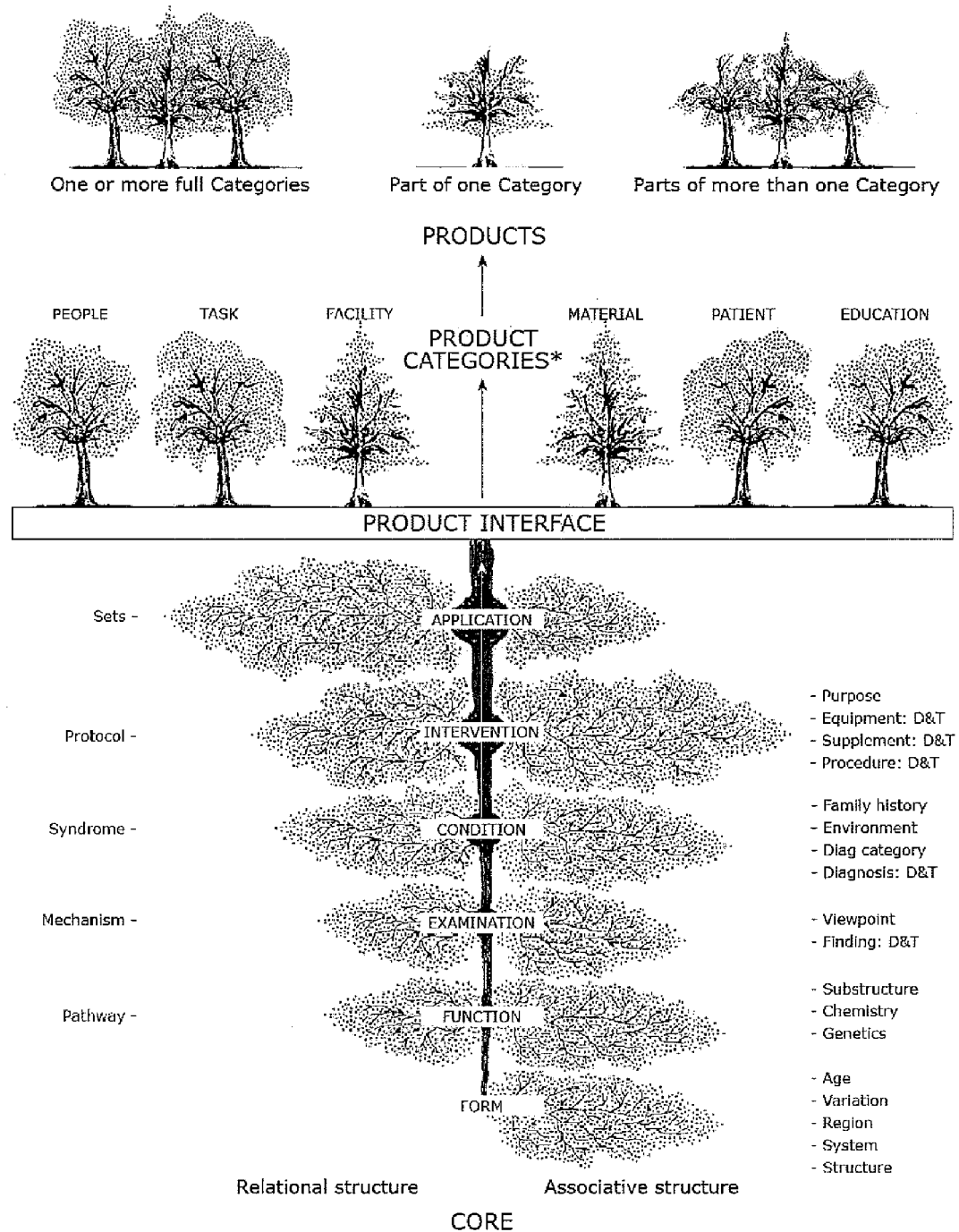
FIG. 11 is a diagram depicting an Apparatus overview.

FIG. 11 is a diagram representing an Apparatus overview. It is an illustration depicting the various components of the apparatus and how coded terms are organized and how terms in the lowest levels of the Core are combined with higher level terms to be used as Sets and be organized into Product Categories. FIG. 11 is a high-level overview of the metadata apparatus and illustrates the relationship between the Core, Product Interface, Product Categories and individual management Products. Notice that while the number of Product Categories is quite small (6-8), the number of different products is unlimited and all of them use the same Core metadata. The organizational scheme of the Core was designed for one purpose, and one purpose only—to deliver comprehensive digital terminology to the management products so computers can do what they do best. It does this by combining unique terms (i.e. terms represented only once), and their related terms, with terms in the same or lower sections to build deep, granular definitions. No more vague subjective definitions, because every term in the Application section Sets and Product Category has a precise definition already attached. The term and all of the metadata in its definition are then available to the management software.

Detailed Specifications

Product

The apparatus was created to provide a comprehensive electronic platform for management products in a specific discipline, where the discipline is determined by the complex item defined by the apparatus. The complex item, and therefore the discipline, can be virtually anything including machines (e.g. planes, trains, automobiles or space vehicles), computer systems, government and health care. In this document, the human body is the complex item and the discipline is health care. The following specifications describe a Product for the management of an ORGANIZATION in the medical specialty of diagnostic radiology (AKA medical imaging).

Diagnostic radiology is responsible for nearly all of the imaging studies and image-guided therapies in medicine. It is also the most progressive medical specialty in terms of adopting an electronic platform so a large portion of the work in diagnostic radiology is already digital and performed on computers. Radiology was also selected as it has a significant presence in nearly all other medical specialties.

Figure 4A:
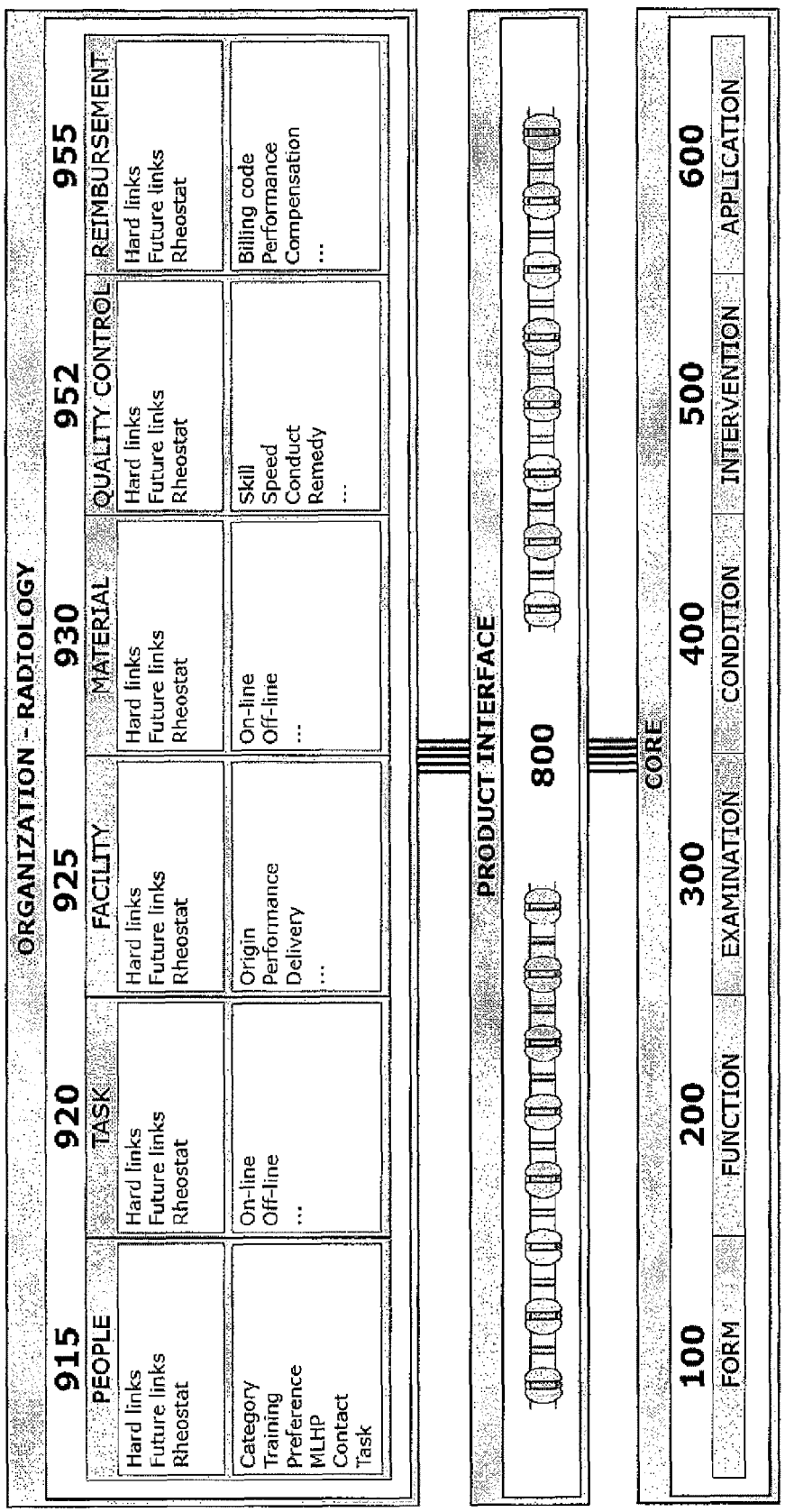
FIG. 4A is a diagram depicting a Product in accordance with the present invention.

The Product is composed of elements from four product categories and two products (see FIG. 4A).

The People in a radiology organization are defined on several levels. The first level parallels the architecture in the Intervention section and others rely heavily on pre-defined Sets. These definitions are then combined with additional descriptive data to create a single profile for each individual.

Initially, People are divided into two general categories—Interventional and Support-I. Support-I is the designation for People who work in the organization to support the overall operation and have responsibilities other than those defined as Interventional. Support-I People include custodial, housekeeping, courier, IT, cafeteria and gift-shop employees, etc. In contrast, the Interventional category includes People who interact, or intervene, with the patient directly and/or with the equipment, supplements or procedures that ultimately interact with the patient or patient data.

For most radiology organizations, the Support-I category has very few individuals. Most of the individuals fall into the Interventional category.

People in the Interventional category are further defined by their level of training. Sets are created for training programs and at each level of training, the appropriate set is added to the individual's profile. These Sets include full training programs as well as individual CME, CAQ and special skills courses. Date:Time stamps are also applied to each program, course and qualification exam.

Work preferences are then added to the profile. Preferences include not only the type of work the individual prefers (subset of qualifications), but also how much they'd like (volume) and when they'd like it (specific days and hours). These elements are available to several built-in scheduling modules—one for each type of Practitioner. For on-line work, how the individual would like it presented is also part of the profile.

Work preferences are also used to direct on-line work and to schedule patients (off-line work).

In radiology, work is performed by radiologists who are physicians trained to interpret imaging studies and perform image-guided procedures. As physicians, each radiologist is required to have a license to practice medicine in the state and, for hospital-based work, have privileges at the hospital. Licenses are granted based on training level and quality control compliance, while Privileges add documentation for specific skill-sets. Medical licenses and hospital privileges are both part of the radiologist profile (MLHP).

Another component of the profile is the individual's contact information. Name, address, phone numbers, e-mail addresses, date of birth, title, professional organizations and any other information the organization requires (spouse's and children's' names and birth dates, hobbies, etc.).

The final and most dynamic profile element is the assignment of tasks. While all of the components of an individual's profile change periodically, Task assignment can change from day-to-day. Tasks are used extensively for both Scheduling and Quality Control.

A Task is one element of a job description, or in other words, each position in the organization is defined by any number of tasks. Each individual Task is defined in the Application area as part of a Work Set. In addition to the Work definition, each Task is also related to quality parameters including Date:Time stamps and Conduct measures. Tasks can either be on-line or off-line.

On-line tasks vary between personnel in a radiology organization, and some tasks can be performed by more than one Practitioner. Technologists, and technology students, are responsible for performing the imaging studies, labeling the series and studies appropriately, updating the clinical history and communicating adverse reactions. Patient scheduling is usually done by the receptionist, but scheduling may also be performed by a technologist, especially for special procedures. Interpreting imaging studies, however, is the exclusive domain of the radiologist.

Studies are presented-to a radiologist in a work list Each radiographic study has already been defined by the core in the Work Set. The radiologist has also been defined in their profile. The work list is therefore the end result of a matching exercise.

From the radiologist profile, qualifications, preferences, medical license, hospital privilege and task are matched with each study including its work definition, facility and state of origin. The total number of radiologists working at a given time and the 'total number of studies to be read' per unit time are then factored into the equation to generate a work list for each radiologist. The average time a study stays on the work list and the off-line responsibilities of the radiologist are also used to balance the work lists and make sure that all of the on-line tasks are completed in a timely fashion.

The 'total number of studies to be read' is based on historical data from the facilities served by the organization. Formulas to more accurately predict work volume take number of ordering practitioners, mobile service schedules, month and day of the week into account.

Off-line tasks for radiologists include all image-guided procedures, in addition to general conduct compliance. Qualifications to perform each procedure are included in the radiologist profile. Since procedures are also part of the Work Set defined by the core, radiologists and procedures are again matched. The only difference between scheduling procedures and generating a work list is that the radiologist has to be in a specific location to perform the procedure.

So far, we've defined tasks and the people who perform them, but we haven't addressed where the tasks are performed. Facility defines the 'where'.

The Facility table creates a profile for each Facility involved in the practice of a radiology organization. The five Facility designations are: Origin, Performance, Interpretation, Delivery and Support. The first four designations refer to the study life cycle from the Practitioner order to the delivery of the final report. Support refers to facilities and organizations outside the life cycle of a study and include accounting, billing, IT, marketing, legal, etc.

Facilities are built using the modular definitions for Place in Sets. In addition to office and hospital-based locations, Facility also has definitions for home and mobile work.

In addition to defining a Facility by the kind of tasks it can accommodate, and the skill-sets of the people performing and interpreting them, other people need to be defined to close the loop. In radiology, these definitions are largely confined to delivery preferences and contact information, including core definitions for specialty. Facility Date:Time stamps are applied to the study at each stage of the life cycle.

Facility is also an important parameter for the scheduling features for both on-line and off-line tasks.

Pre-fetching is an important feature of on-line PACS systems, so knowing where and when a radiologist is working helps deliver their work before they arrive. The scheduling features for off-line tasks that require a radiologist in attendance match the physical location of both the radiologist and the task.

On-line and off-line tasks require Material. As in the Intervention section, Material is defined as Equipment and Supplement. The Equipment for on-line tasks ranges from a computer and connectivity to every piece of computer hardware and software in a radiology department or imaging center. Material for off-line tasks includes basic office equipment, contrast agents, and an assortment of catheters, needles, and monitoring devices. Facility Date:Time stamps are also applied to materials at each stage of the life cycle for inventory purposes.

As stand-alone products, Quality Control and Reimbursement for radiology are both applied across the previously described components of the Organization (product categories).

In the apparatus, Quality Control (QC) has a head start because not only is every study and every individual already defined by the core, but a high percentage of tasks are on-line. To promote efficient implementation, QC features are integrated with the PACS and RIS. For on-line tasks, the standard QC criteria offered by the guiding physician organizations are used in conjunction with custom features designed to minimize future errors. If an error is the action, the response to the error is the reaction. Some of these Reactions are listed below.

The Quality Control data can be accessed by different individuals in the Organization including a QC Officer, practice manager and individuals directly involved in an occurrence. As with the apparatus as a whole, access to QC data can be summarized and reported.

For radiology, Quality Control divides errors into five categories corresponding to the Facility designations—Origin, Performance, Interpretation, Delivery and Support.

Errors at the Origin are process errors and include ordering the incorrect study, providing incomplete or inaccurate clinical data, and omitting important demographic data needed by related systems (HIS, RIS, billing, etc.). The Reaction is track the user at the Origin Facility who enters the data, provide feedback summaries to the Facility at prescribed intervals (weekly, quarterly), log the errors internally to aid in the development of educational materials, and issue internal alerts when error frequency reaches established thresholds. Internal reports including this data and data on software pulled from the Facility profile are also generated.

Errors in Performance include anything related to the performance of the study from performing the wrong exam, mislabeling right and left, and improper technique to errors in labeling and delays forwarding the study for interpretation. Most of the Performance errors are process errors and are directed at technologists, but for interventional procedures, the same measures are used to assess radiologists. For technologists, the Reaction is very similar to that described above for Origin. The Reaction for radiologists is the similar to that described below for Interpretation.

Errors during Interpretation focus on the radiologist. The apparatus is designed to catalog errors of interpretation and process. Process errors include failing to notify practitioners of critical findings, and prolonged delays in either reading a study or signing the report and are addressed in a manner similar to process errors in Origin and Performance. Errors of interpretation are handled differently.

As with the process errors already described, Quality Control provides a secure environment for a select group of individuals to monitor and address errors. These errors may be entered individually via connections to other electronic systems, or manually by the practice manager or QC Officer. On-line peer review sessions are also included.

For errors of interpretation, the core definitions provide an added level of control as the metadata attached to each study is used to create a detailed profile of elements that may be responsible for the error or errors for an individual. Not only does this metadata help identify subtle trends, it can also be used to identify specific areas for remedial education if needed. Since the educational materials are also defined with the same metadata, matching remedial education to errors is automatic.

Peer review sessions are an important adjunct to the QC process. During these sessions, electronic questionnaires are configured to pop-up when a new study has a similar reference study, the report is included and the reading radiologist on the reference is someone other than the current reader. Pop-ups can be configured to trigger with any combination of Core parameters, at any frequency and at either regular or random intervals.

The questionnaires simply asks the new reader if they agree with the report for the reference study. 'No' answers require the reader to make a few more clicks before signing off and returning to read. 'Yes' answers offer a place to leave a positive comment (if warranted) before signing off. Peer review sessions are also managed by the QA officer and/or practice manager.

The QC features available to these select individuals include constructing peer review sessions for all or selected subsets of the radiologists in the organization, creating focused review sessions for a single radiologist who recently expanded their profile by attending a new course or additional training (mentoring), or monitoring one who has had a higher number of errors in certain areas (over reading).

Errors in Delivery and Support are process errors like those described previously. Delivery deals specifically with providing final reports to the appropriate parties while Support addresses errors related to facilities and organizations outside the life cycle of a study including accounting, billing, IT, marketing, legal, etc.

Reimbursement, like Quality Control, is another stand-alone product that's incorporated into the Organization product. The two major topics for Reimbursement are Billing and Compensation.

Billing refers to the all of the processes involved in submitting a bill for service, where the payment is delivered to the organization as a whole.

In radiology, the various health care payors use fee schedules and payment codes to determine how much they'll pay for a procedure or examination. The apparatus maps each of these codes to the corresponding procedure and examination already defined by the core in Sets. As work is performed, and reports generated, the apparatus tracks the corresponding billing codes. These codes can then be exported to a third-party billing company or used internally to bill for services rendered.

The Reimbursement product was designed to use existing codes and fee schedules as well as explore new methods to quantify the value of these services—both in terms overall reimbursement and internal compensation because the metadata defining the work is so-much more detailed than the billing codes, and the value of each examination and procedure is so much easier to quantify (time and experience needed to perform, impact on health care, risk, etc.), this feature of the product has a distinct advantage over other methods.

This approach also applies to dividing the collected proceeds among the individuals doing the work.

The current method of assigning wRVUs (work relative value units) is on the right track, but when wRVUs are mapped against the core metadata, they become even more accurate and useful. WRVUs are also part of the radiologist scheduling system and can be used to modify the volume and content of a radiologist work list based upon predetermined thresholds.

The Reimbursement component of the Organization product is also flexible enough to comply with pay-for-performance criteria—whatever they may be.

In closing, the reporting features of the Organization product can utilize any or all of the definitions, profiles and components of the apparatus described in this document.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system for generating and storing a plurality of definitions, comprising:
a) a first multi-level database located on a server, wherein the first multi-level database is associative, said server comprising a core, wherein a first part of the core comprises the first multi-level database, said first multi-level database comprising a plurality of terms, wherein each term of the plurality of terms is included in the first multi-level database once and only once, said plurality of terms comprising a plurality of first-level terms having a first common theme and a plurality of second-level terms having a second common theme, said first multi-level database further comprising a plurality of numeric first-level term codes and a plurality of numeric second-level term codes, wherein each first-level term is assigned a numeric first-level term code of the plurality of numeric first-level term codes, and each second-level term is assigned a numeric second-level term code of the plurality of numeric second-level term codes, wherein the first multi-level database is divided into a plurality of sections including a first section and a second section, said first section comprising a plurality of first-level tables, a plurality of numeric first-level table codes, and a first node table, wherein each first-level table is assigned a numeric first-level table code of the plurality of numeric first-level table codes, and the plurality of first-level terms and the plurality of numeric first-level term codes are located in the plurality of first-level tables, and
wherein a plurality of first code strings are formed in the first node table, wherein each first code string is formed by joining together at least one numeric first-level term code from a first-level table of the plurality of first-level tables, at least one numeric first-level table code, and first-level code language describing the location and relations of said first-level table, said second section comprising a plurality of second-level tables, a plurality of numeric second-level table codes, and a second node table, wherein each second-level table of the plurality of second-level tables is assigned a numeric second-level table code of the plurality of numeric second-level table codes, and the plurality of second-level terms and the plurality of numeric second-level term codes are located in the plurality of second-level tables, wherein the first section communicates with the second section through the first node table and the second node table, and
wherein a plurality of second code strings and a plurality of combined code strings are formed in the second node table, wherein each second code string is formed by joining together at least one numeric second-level term code from a second-level table of the plurality of second-level tables, at least one numeric second-level table code, and second-level code language describing the location and relations of said second-level table, and wherein each combined code string is formed by joining a second code string to a first code string of the plurality of first code strings from the first node table;
b) a second multi-level database connected to the first multi-level database, wherein the second multi-level database is relational, and wherein a second part of the core comprises the second multi-level database, said second multi-level database comprising a plurality of defined words and phrases and the plurality of definitions, wherein each definition is a final code string formed in a final node table of the first multi-level database, and wherein each defined word and phrase of the plurality of defined words and phrases is joined with a definition of the plurality of definitions, wherein the plurality of defined words and phrases and the plurality of definitions function as an industry-specific electronic dictionary, and wherein the second multi-level database is configured to allow the plurality of defined words and phrases and the plurality of definitions to be arranged into a plurality of sets based on a plurality of common attributes or applications, wherein a common attribute or application of the plurality of common attributes or applications is a device, a specialty, a practitioner, work, a place, examination, therapy, prevention, a practitioner, training, or a discipline of study or research;
c) a multi-functional interface layer on the server, wherein the multi-functional interface layer is connected to the core, wherein said multi-functional interface layer is configured to provide a security feature to prevent unauthorized access to the core and to create and store detailed profiles for users, wherein data entry and quality assurance processes interface with the core during development and maintenance, wherein the plurality of numeric first-level term codes are translated into first-level terms, the plurality of numeric second-level term codes are translated into second-level terms, and the plurality of definitions are translated into defined words and phrases when necessary, and wherein the plurality of defined words and phrases and the plurality of definitions are organized and presented to the less secure environment outside the multi-functional interface layer for data files either generated by outside software programs or presented to outside software programs from an outside source;

d) a processor located on the server, wherein said processor is adapted to manage the plurality of terms, the plurality of defined words and phrases, and the plurality of definitions in the core and multi-functional interface layer by retrieving, organizing, displaying and analyzing desired data; and e) one or more computing devices in communication with the server.

2. The system of claim 1, wherein the final node table is located in a final section of the plurality of sections, said final section comprising a plurality of final-level terms having a final common theme, wherein said final common theme is Application, and wherein the number of sections in the plurality of sections, and a common theme of each section in the first multi-level database, depends on a complex item upon which an industry to which the electronic dictionary pertains is based, wherein for a health care industry the complex item is the human body and six sections, including the final section, are needed to adequately describe all elements of the health care industry, and wherein, from lowest to highest, the first common theme of the first section is Form, the second common theme of the second section is Function, a third common theme of a third section is Examination, a fourth common theme of a fourth section is Condition, and a fifth common theme of a fifth section is Intervention.

3. The system of claim 1, wherein each first-level term of the plurality of first-level terms of the first multi-level database pertains to an attribute of a form of a complex item upon which an industry to which the electronic dictionary pertains is based, and the first common theme of the plurality of first-level terms is form, wherein the attribute of the form is a name, a size, a shape, a relative location, a region, or a system of one or more structures or components, and wherein the complex item is of any gender or similar variation, at any age or stage in development;

wherein each second-level term of the plurality of second-level terms of the first multi-level database pertains to an attribute of a function of the complex item at a microscopic level, at a macroscopic level, or at both a microscopic and a macroscopic level, and wherein the second common theme of the plurality of second-level terms is function;

wherein the plurality of terms of the first multi-level database further comprises a plurality of third-level terms, wherein each third-level term of the plurality of third-level terms pertains to an attribute of an examination technique performed on the complex item, wherein the plurality of third-level terms are organized by viewpoint and include verbal terms, sensory or physical terms, electrical terms, imaging terms, sampling terms, photography terms and rendering terms; and wherein the final code string formed in the final node table is formed by joining together a combined code string of the plurality of combined code strings and at least one additional code string, said at least one additional code string comprising a numeric additional code assigned to an additional term, wherein the additional term pertains to an additional attribute describing a state of the complex item or a factor that interacts with the complex item, and the additional attribute is a finding on an examination technique, a normal condition, an abnormal condition, a diagnostic category for a known disorder, a diagnostic category for an unnamed disorder, a family history, a genetic composition, a geographic location, a geographic exposure, a supplement to maintain health or treat disorders, equipment to maintain health or treat disorders, or a procedure to maintain health or treat disorders.

4. The system of claim 1, wherein the electronic dictionary pertains to the health care industry, and wherein each first-level term of the plurality of first-level terms pertains to an attribute of a form of a human body, and the first common theme of the plurality of first-level terms is form, wherein the attribute of the form of the human body is a name, a size, a shape, a relative location, an anatomic region, or a physiologic system of one or more structures or components, and wherein the human body may be a body of either sex at any age;

wherein each second-level term of the plurality of second-level terms of the first multi-level database pertains to an attribute of a function of the human body at a microscopic level, at a macroscopic level, or at both a microscopic and a macroscopic level, and wherein the second common theme of the plurality of second-level terms is function;

wherein the plurality of terms of the first multi-level database further comprises a plurality of third-level terms, wherein each third-level term of the plurality of third-level terms pertains to an attribute of an examination technique performed on the human body, wherein the plurality of third-level terms are organized by viewpoint and include verbal terms, sensory or physical terms, electrical terms, imaging terms, sampling terms, photography terms and rendering terms; and wherein the final code string formed in the final node table is formed by joining together a combined code string of the plurality of combined code strings and at least one additional code string, said additional code string comprising a numeric additional code assigned to an additional term, wherein the additional term pertains to an additional attribute describing a state of the human body or a factor that interacts with the body, and the additional attribute is a finding on an examination technique, a normal condition, an abnormal condition, a diagnostic category for a known disorder, a diagnostic category for an unnamed disorder, a family history, a genetic composition, a geographic location, a geographic exposure, a supplement to maintain health or treat disorders, equipment to maintain health or treat disorders, or a procedure to maintain health or treat disorders.

5. The system of claim 1, wherein a set of the plurality of sets resides in an external device that generates computer data files used in an industry to which the electronic dictionary pertains.

6. The system of claim 1, wherein each first-level table of the plurality of first-level tables is related to a rheostat table, said rheostat table comprising a plurality of rheostat terms used to adjust a relative value of a numeric first-level term code of the plurality of numeric first-level term codes, wherein said numeric first-level term code is selected for a specific numeric definition, wherein the rheostat table comprises a numeric term for scale or a numeric term for percentage.

7. The system of claim 1, wherein said processor is adapted to provide security functions at the multi-functional interface layer between a plurality of electronic files from outside sources and the plurality of terms, the plurality of defined words and phrases, and the plurality of definitions in the core.

8. The system of claim 1, wherein said processor is adapted to segregate sensitive data from non-sensitive data.

9. The system of claim 1, wherein the electronic dictionary pertains to the health care industry, and the electronic dictionary provides definitions for a plurality of structures in a human body, wherein the plurality of structures are defined by their anatomic region, physiologic system, absolute size, absolute shape and relative position in the human body at all ages of the human body, and by the plurality of findings on all examination techniques for a structure of the plurality of structures in all normal states and all abnormal conditions.

10. The system of claim 1, wherein the electronic dictionary pertains to the health care industry, and the electronic dictionary provides definitions for a plurality of conditions that affect a human body, wherein the plurality of conditions are defined by a plurality of findings from examination techniques for a plurality of viewpoints on a function of the human body, a form of the human body, or both the form of the human body and the function of the human body.

11. The system of claim 1, further comprising an electronic device, wherein the electronic dictionary pertains to the health care industry, and the electronic device is a medical imaging device, a laboratory analysis device, or a patient surveillance device.

12. A method of generating and storing a plurality of definitions to be applied to a plurality of electronic files as metadata, by execution of computer readable program code by at least one processor of at least one computer system, comprising:
    providing a multi-level database comprising a plurality of terms, wherein each term of the plurality of terms is included in the multi-level database once and only once, said plurality of terms comprising a plurality of first-level terms having a first common theme and a plurality of second-level terms having a second common theme, said multi-level database further comprising a plurality of numeric first-level term codes and a plurality of numeric second-level term codes, wherein each first-level term is assigned a numeric first-level term code of the plurality of numeric first-level term codes, and each second-level term is assigned a numeric second-level term code of the plurality of numeric second-level term codes, wherein the multi-level database is divided into a plurality of sections including a first section and a second section, said first section comprising a plurality of first-level tables, a plurality of numeric first-level table codes, and a first node table, wherein each first-level table is assigned a numeric first-level table code of the plurality of numeric first-level table codes, and the plurality of first-level terms and the plurality of numeric first-level term codes are located in the plurality of first-level tables, said second section comprising a plurality of second-level tables, a plurality of numeric second-level table codes, and a second node table, wherein each second-level table of the plurality of second-level tables is assigned a numeric second-level table code of the plurality of numeric second-level table codes, and the plurality of second-level terms and the plurality of numeric second-level term codes are located in the plurality of second-level tables, wherein the first section communicates with the second section through the first node table and the second node table;
    forming a first code string in the first node table, by joining together at least one numeric first-level term code from a first-level table of the plurality of first-level tables, at least one numeric first-level table code, and first-level code language describing the location and relations of said first-level table, using at least one of the processors;
    forming a second code string in the second node table, by joining together at least one numeric second-level term code from a second-level table of the plurality of second-level tables, at least one numeric second-level table code, and second-level code language describing the location and relations of said second-level table, using at least one of the processors;
    forming a combined code string in the second node table, by joining together the first code string and the second code string, using at least one of the processors;
    creating a plurality of definitions, each definition comprising a final code string, wherein each final code string is formed in a final node table of the multi-level database, using at least one of the processors; and
    joining each definition of the plurality of definitions with a defined word and phrase of a plurality of defined words and phrases, using at least one of the processors, wherein the plurality of definitions and the plurality of defined words and phrases function as an industry-specific electronic dictionary.

13. The method of claim 12, wherein each final code string is formed by joining together the combined code string and at least one additional code string, using at least one of the processors, said additional code string comprising a numeric additional code assigned to an additional term, wherein the additional term pertains to an additional attribute describing a state of a complex item or a factor that interacts with the complex item, and the additional attribute is a finding on an examination technique, a normal condition, an abnormal condition, a diagnostic category for a known disorder, a diagnostic category for an unnamed disorder, a family history, a genetic composition, a geographic location, a geographic exposure, a supplement to maintain health or treat disorders, equipment to maintain health or treat disorders, or a procedure to maintain health or treat disorders;
    wherein each first-level term of the plurality of first-level terms pertains to an attribute of a form of the complex item, and the first common theme of the plurality of first-level terms is form, wherein the attribute of the form is a name, a size, a shape, a relative location, a region, or a system of one or more structures or components, and wherein the complex item is of any gender or similar variation, at any age or stage in development; and
    wherein each second-level term of the plurality of second-level terms pertains to an attribute of a function of the complex item at a microscopic level, at a macroscopic level, or at both a microscopic and a macroscopic level, and wherein the second common theme of the plurality of second-level terms is function.

14. The method of claim 12, wherein the final node table is located in a final section of the plurality of sections, said final section comprising a plurality of final-level terms having a final common theme, wherein said final common theme is Application, and wherein the number of sections in the plurality of sections, and a common theme of each section in the multi-level database, depends on a complex item upon which an industry to which the electronic dictionary pertains is based, wherein for a health care industry the complex item is the human body and six sections, including the final section, are needed to adequately describe all elements of the health care industry, and wherein, from lowest to highest, the first common theme of the first section is Form, the second common theme of the second section is Function, a third common theme of a third section is Examination, a fourth common theme of a fourth section is Condition, and a fifth common theme of a fifth section is Intervention.

15. The method of claim 12, further comprising applying one or more definitions of the plurality of definitions to each electronic file of the plurality of electronic files as metadata.

16. The method of claim 12, wherein the plurality of electronic files comprises a device electronic file, said device electronic file comprising data generated by an electronic device, and wherein for a health care industry the electronic device is a medical imaging device, a laboratory analysis device, or a patient surveillance device.

17. The method of claim 12, wherein the plurality of electronic files includes health care data, further comprising segregating sensitive data of the health care data from non-sensitive data of the health care data, using at least one of the processors.

18. The method of claim 12, wherein the plurality of electronic files includes health care data, further comprising allowing secure access to the health care data by providing a controllable interference layer between the plurality of electronic files and the plurality of terms, using at least one of the processors.

19. The method of claim 12, wherein the plurality of electronic files includes health care data, further comprising identifying desired data of the health care data by searching the metadata for desired terms of the plurality of terms, using at least one of the processors.

20. The method of claim 19, further comprising retrieving, organizing, and displaying the desired data, using at least one of the processors.

21. The method of claim 19, further comprising performing analytic exercises on the desired data, using at least one of the processors.

* * * * *